(12) United States Patent
Varol

(10) Patent No.: US 12,661,180 B2
(45) Date of Patent: *Jun. 23, 2026

(54) SYSTEM WITH VIBRATION DEVICE AND COOLING FLUID FOR INTERSTITIAL LASER THERAPY

(71) Applicant: MEDLOGICAL INNOVATIONS PTY LTD, Kingswood (AU)

(72) Inventor: Celalettin Varol, Hunters Hill (AU)

(73) Assignee: MEDLOGICAL INNOVATIONS PTY LTD, New South Wales (AU)

( * ) Notice: Subject to any disclaimer, the term of this patent is extended or adjusted under 35 U.S.C. 154(b) by 301 days.

This patent is subject to a terminal disclaimer.

(21) Appl. No.: 18/475,170

(22) Filed: Sep. 26, 2023

(65) Prior Publication Data

US 2024/0008923 A1     Jan. 11, 2024

Related U.S. Application Data

(63) Continuation-in-part of application No. 17/629,073, filed as application No. PCT/AU2019/051039 on Sep. 26, 2019, now Pat. No. 12,193,735.

(30) Foreign Application Priority Data

Jul. 24, 2019    (AU) ................................. 2019902617

(51) Int. Cl.
| | |
|---|---|
| *A61B 5/00* | (2006.01) |
| *A61B 18/22* | (2006.01) |
| *A61B 18/00* | (2006.01) |

(52) U.S. Cl.
CPC ..... *A61B 18/22* (2013.01); *A61B 2018/00011* (2013.01); *A61B 2018/00577* (2013.01);
(Continued)

(58) Field of Classification Search
CPC .......... A61B 18/22; A61B 2018/00011; A61B 2018/00577; A61B 2018/2238;
(Continued)

(56) References Cited

U.S. PATENT DOCUMENTS

| | | |
|---|---|---|
| 4,718,417 A | 1/1988 | Kittrell et al. |
| 5,647,851 A | 7/1997 | Pokras |

(Continued)

FOREIGN PATENT DOCUMENTS

| | | |
|---|---|---|
| EP | 3058888 A1 | 8/2016 |
| FR | 3021520 A1 | 12/2015 |

(Continued)

OTHER PUBLICATIONS

Applicant: Medlogical Innovations Pty Ltd; "System with Cooling Fluid for Interstitial Laser Therapy"; PCT International Application No. PCT/AU2019/051039 filed Sep. 26, 2019; PCT International Search Report dated Dec. 11, 2019; 4 pgs.

(Continued)

*Primary Examiner* — Scott M. Getzow

(74) *Attorney, Agent, or Firm* — Tarolli, Sundheim, Covell & Tummino LLP

(57)     ABSTRACT

Disclosed is a system provided with a vibration device and cooling fluid for interstitial laser therapy. Use of the vibration device to vibrate at least part of the system releases and assists in the transfer of gas bubbles (e.g. steam) produced during treatment use, thus stabilising the temperature at or near a treatment site. The system for interstitial laser therapy includes an optical waveguide having an optical output end and an associated optical diffuser, an irrigation tube, an outer tube (e.g. cannula) and a vibration device. The irrigation tube directs cooling fluid to flow out of a distal end of the irrigation tube which directs cooling fluid to flow inside of and/or outside of the optical diffuser. The vibration device is (Continued)

used to vibrate the irrigation tube, the optical diffuser and/or the outer tube.

24 Claims, 29 Drawing Sheets

(52) U.S. Cl.
CPC ................ *A61B 2018/2238* (2013.01); *A61B 2018/2261* (2013.01); *A61B 2217/007* (2013.01)

(58) Field of Classification Search
CPC ...... A61B 2018/2261; A61B 2217/007; A61B 2018/00023; A61B 2018/00029; A61B 2018/0019; A61B 2018/00446; A61B 2018/00529; A61B 2018/00547; A61B 2018/00642; A61B 2018/00702; A61B 2018/00744; A61B 2018/00785; A61B 2018/00797; A61B 2018/00821; A61B 2018/2005; A61B 2218/002
See application file for complete search history.

(56) References Cited

U.S. PATENT DOCUMENTS

| | | | |
|---|---|---|---|
| 5,754,717 | A | 5/1998 | Esch |
| 5,758,663 | A | 6/1998 | Wilk et al. |
| 6,056,745 | A | 5/2000 | Panescu et al. |
| 6,522,806 | B1 | 2/2003 | James, IV et al. |
| 8,986,298 | B2 | 3/2015 | Lee |
| 10,631,930 | B1 | 4/2020 | Miyagawa et al. |
| 11,672,557 | B2 | 6/2023 | Khouri et al. |
| 2001/0056278 | A1 | 12/2001 | Nield et al. |
| 2003/0023236 | A1 | 1/2003 | Gowda et al. |
| 2004/0044336 | A1 | 3/2004 | Shafirstein et al. |
| 2005/0113815 | A1 | 5/2005 | Ritchie et al. |
| 2005/0131399 | A1 | 6/2005 | Loeb et al. |
| 2005/0135749 | A1 | 6/2005 | Nield et al. |
| 2005/0137587 | A1 | 6/2005 | Nield et al. |
| 2008/0086160 | A1 | 4/2008 | Mastri et al. |
| 2009/0005768 | A1 | 1/2009 | Sharareh et al. |
| 2009/0005771 | A1 | 1/2009 | Lieber et al. |
| 2009/0005773 | A1 | 1/2009 | Beeckler et al. |
| 2009/0131931 | A1 | 5/2009 | Lee et al. |
| 2009/0240242 | A1 | 9/2009 | Neuberger |
| 2010/0217360 | A1 | 8/2010 | Henriksson et al. |
| 2011/0105824 | A1 | 5/2011 | Krespi |
| 2011/0295261 | A1 | 12/2011 | Germain |
| 2011/0295262 | A1 | 12/2011 | Germain et al. |
| 2011/0301584 | A1 | 12/2011 | Beck et al. |
| 2012/0022510 | A1 | 1/2012 | Welches et al. |
| 2013/0261615 | A1 | 10/2013 | Kramer et al. |
| 2013/0261621 | A1 | 10/2013 | Kramer et al. |
| 2014/0088488 | A1 | 3/2014 | Loeb |
| 2014/0243808 | A1 | 8/2014 | Molnar-Hammond et al. |
| 2015/0057648 | A1 | 2/2015 | Swift et al. |
| 2016/0022358 | A1 | 1/2016 | Sharareh et al. |
| 2016/0206374 | A1 | 7/2016 | Tyc et al. |
| 2017/0014186 | A1 | 1/2017 | Chen et al. |
| 2017/0014202 | A1 | 1/2017 | Ransbury et al. |
| 2017/0209677 | A1 | 7/2017 | Kang et al. |
| 2017/0311880 | A1 | 11/2017 | Jacobsen et al. |
| 2018/0341074 | A1 | 11/2018 | Yu et al. |
| 2019/0029756 | A1 | 1/2019 | Natarajan et al. |
| 2019/0321100 | A1 | 10/2019 | Masotti et al. |
| 2019/0321101 | A1 | 10/2019 | Masotti et al. |
| 2019/0321102 | A1 | 10/2019 | Masotti et al. |
| 2019/0357978 | A1 | 11/2019 | Dymling et al. |
| 2020/0323589 | A1 | 10/2020 | Varol |
| 2022/0273366 | A1 | 9/2022 | Varol |

FOREIGN PATENT DOCUMENTS

| | | |
|---|---|---|
| WO | 2009124301 A1 | 10/2009 |
| WO | 2018112261 A1 | 6/2018 |
| WO | 2018170549 A1 | 9/2018 |
| WO | 2022105848 A1 | 5/2022 |
| WO | 2022147472 A1 | 7/2022 |
| WO | 2022211010 A1 | 10/2022 |

OTHER PUBLICATIONS

European Search Report for Application No. 18770419.2-112/ 3600107 PCT/AU20118050262 dated Jul. 24, 2020.
Singapore Search Report for Application No. 11201907525Y dated Dec. 21, 2020.
Singapore Written Opinion for Application No. 11201907525Y dated Dec. 23, 2020.

630

640

SYSTEM WITH VIBRATION DEVICE AND COOLING FLUID FOR INTERSTITIAL LASER THERAPY

CROSS-REFERENCE TO RELATED APPLICATION

This patent application is a Continuation-in-Part of U.S. patent application Ser. No. 17/629,073, filed Jan. 21, 2022, and entitled SYSTEM WITH COOLING FLUID FOR INTERSTITIAL LASER THERAPY, which claims priority to U.S. National Stage Application filed under 35 U.S.C. § 371 of PCT/AU2019/051039, filed Sep. 26, 2019, and entitled SYSTEM WITH COOLING FLUID FOR INTERSTITIAL LASER THERAPY, which International Application claims the benefit of priority from Australian Patent Application No. 2019902617, filed on Jul. 24, 2019. The entire contents of each of the above-identified patent applications are incorporated herein by reference.

TECHNICAL FIELD

The present invention generally relates to the field of interstitial laser thermotherapy. In specific examples, a temperature sensor is formed or provided as part of a device for interstitial laser therapy. In further specific examples, there is provided a system with cooling fluid for interstitial laser therapy. In further specific examples, there is provided a vibration device to vibrate one or more components of the system. In examples, the device for interstitial laser therapy is part of the system with a vibration device and cooling fluid for interstitial laser therapy.

BACKGROUND

Optical fibres exhibit excellent light-guiding properties which, combined with a compact size and flexibility, make them ideal for various medical applications. Interstitial laser therapy is one such application, in which light is directed at a target tissue to induce local hyperthermia and destroy the tissue. Interstitial laser therapy can be effective for treating lesions and tumours, particularly those difficult to access using conventional surgery. Interstitial techniques of local hyperthermia deep inside a patient's body offer a safe and effective way of treating cancers. Tumours can be accessed via a cannula, minimising the invasiveness of the procedure and improving patient comfort while reducing side effects. A key challenge in interstitial laser therapy involves monitoring and controlling the temperature of the target area during treatment. Hyperthermia is capable of destroying both tumour tissue as well as any surrounding healthy tissue. It has been well established that heating tissue to 60° C. for one minute induces irreversible cell death. At 100° C., tissue destruction is immediate. Typically, the aim of thermotherapy is to induce local hyperthermia and coagulative necrosis in a target tissue, without causing charring. It is therefore critical that the temperature of the target area be continuously monitored during interstitial laser therapy, to provide real-time feedback on the status of the target area.

Advanced medical imaging devices such as magnetic resonance imaging (MRI) scanners, with the aid of external computer interfaces, may be used to estimate internal temperatures during interstitial laser therapy. These devices however are expensive, bulky, and their operation necessitates extensive training. Moreover, the temperature readings they provide are not direct measurements but have to be extrapolated by a computer and can therefore suffer from low accuracy. The lack of rapid and reliable feedback concerning the tissue's temperature means that current thermotherapy devices necessitate cooling systems to minimise the risk of charring the tissue. Example cooling systems include cooling or irrigation catheters. These cooling systems however increase the overall size of the accessing cannula, inducing greater trauma to the patient.

There is a need for new or improved devices and/or systems for interstitial laser therapy. The reference in this specification to any prior publication (or information derived from the prior publication), or to any matter which is known, is not, and should not be taken as an acknowledgment or admission or any form of suggestion that the prior publication (or information derived from the prior publication) or known matter forms part of the common general knowledge in the field of endeavour to which this specification relates.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one aspect there is provided a system for interstitial laser therapy comprising: an optical waveguide having an optical output end; an optical diffuser positioned over the optical output end of the optical waveguide; an irrigation tube, in use positioned over at least part of the optical waveguide, the irrigation tube able to direct a cooling fluid to flow out of an end of the irrigation tube; an outer tube, in use positioned over at least part of the irrigation tube and over the optical diffuser; and a vibration device.

In one example, the vibration device is used to vibrate the irrigation tube. In one example, the vibration device is used to vibrate the optical diffuser by vibrating the irrigation tube being attached to the optical diffuser. In one example, the vibration device is used to vibrate the outer tube.

In another example, there is further provided a fluid guide tube, in use positioned over at least part of the optical diffuser and over at least part of the irrigation tube, and wherein in use the outer tube is positioned over at least part of the fluid guide tube. In one example, the vibration device is used to vibrate the fluid guide tube. In one example, the vibration device is used to vibrate: (i) the irrigation tube and the optical diffuser; (ii) the irrigation tube and the fluid guide tube; (iii) the irrigation tube and the outer tube; or (iv) the irrigation tube and the fluid guide tube and the outer tube.

In one example, there is more than one vibration device, each vibration device used to vibrate one of the irrigation tube and the outer tube. Optionally, the vibration device is a button or coin motor, or a piezo motor. Optionally, the vibration device is a piezoelectric plate vibrator. In one example, the vibration device is attached to the irrigation tube and/or the outer tube. Preferably, the vibration device is positioned away from a laser ablation zone. Optionally, the vibration device is positioned at or near a fluid inlet port or a fluid outlet port for the cooling fluid. Preferably, in use the vibration produced by the vibration device releases gas bubbles. Preferably, the cooling fluid is water and the gas bubbles are steam.

In one example, the optical diffuser is provided with one or more optical diffuser apertures. Preferably, the one or more optical diffuser apertures allow gases generated during use to escape out from an inside region of the optical diffuser. In one example, the cooling fluid is directed to flow inside of the optical diffuser, and wherein the cooling fluid flows out of the optical diffuser partially via at least the one or more optical diffuser apertures. Optionally, the fluid guide tube is provided with one or more fluid guide tube apertures. Preferably, the outer tube includes or is attached to a trocar.

In another aspect there is provided a system for interstitial laser therapy comprising a device for interstitial laser therapy and an irrigation tube positioned over at least part of an optical waveguide of the device for interstitial laser therapy. The irrigation tube is able to direct a cooling fluid to flow out of an end of the irrigation tube. In another aspect, the device for interstitial laser therapy comprises an optical waveguide having an optical output end, and an optical diffuser positioned over the optical output end of the optical waveguide.

In another example, a fluid guide tube is positioned over at least part of the optical diffuser. The fluid guide tube can be positioned over at least part of the irrigation tube. In another example, a cooling fluid is input into the irrigation tube and is directed to flow out of the end of the irrigation tube. In another example, the optical diffuser is provided with one or more optical diffuser apertures. Preferably, the fluid guide tube is provided with one or more fluid guide tube apertures. In another example, the irrigation tube is positioned over part of the optical diffuser. In this example situation, cooling fluid can be directed to flow inside of the optical diffuser. The cooling fluid can preferably flow out of the optical diffuser via at least the one or more optical diffuser apertures. In another example, the irrigation tube is not longitudinally coextensive with the optical diffuser. In this example situation, cooling fluid can be directed to flow outside of the optical diffuser.

Preferably, the cooling fluid flows out of the fluid guide tube via at least the one or more fluid guide tube apertures. Alternatively, the cooling fluid flows into the fluid guide tube via at least the one or more fluid guide tube apertures. Optionally, the cooling fluid flows out of at least a distal end of the fluid guide tube. In another example, as part of the system there is provided an outer tube positioned over at least part of the fluid guide tube. In one option, the outer tube is provided with one or more outer tube apertures. In this situation, the cooling fluid flows out of the outer tube via at least the one or more outer tube apertures. Additionally or alternatively, return cooling fluid flows along the inside of the outer tube. Preferably, though not necessarily, a laser ablation zone is limited in extent by the cooling fluid exiting the irrigation tube. Preferably, though not necessarily, a laser ablation zone is limited in longitudinal extent to forward of an end of the irrigation tube towards an end of the device for interstitial laser therapy. In another example, a longitudinal length of a laser ablation zone is able to be changed by adjusting a position of the irrigation tube and the device for interstitial laser therapy relative to the position of a distal end of the system along a longitudinal axis.

In another example, the system includes a second fluid guide tube positioned between the fluid guide tube and the outer tube. Preferably, if used, the second fluid guide tube is provided with one or more second fluid guide tube apertures. In this situation, in one example, the cooling fluid flows out of the second fluid guide tube via the one or more second fluid guide tube apertures. Alternatively, the cooling fluid flows into the second fluid guide tube via at least the one or more second fluid guide tube apertures. Preferably, the outer tube of the system is used for delivering the device for interstitial laser therapy to a treatment region. Optionally, the outer tube includes or is attached to a trocar. Optionally, at least an end portion of the outer tube and/or the trocar is transparent or semi-opaque. The system with cooling fluid for interstitial laser therapy (i.e. a thermotherapy laser ablation system) limits the laser ablation zone produced by a device for interstitial laser therapy, which allows for better control of the laser ablation zone and more predictive and accurate interstitial laser therapy. The limitation of the laser ablation zone provides for greatly improved accuracy of ablation of tissue in interstitial laser therapy. In a further example, a trocar can form part of a thermocouple. In another example, an annular ring can form part of a second thermocouple, the annular ring may be an annular metal ring. In further examples, the annular ring can be longitudinally positioned at or near a distal end of the optical diffuser, or at or near a distal end of an irrigation tube. In other examples, the annular ring can be positioned external to the optical diffuser, or positioned external to or embedded within an outer tube.

According to other example aspects, there is provided a device and/or a system for interstitial laser therapy. The device preferably comprises an optical waveguide having an optical output end, and an optical diffuser optically coupled to the optical output end. In one example form, the optical diffuser comprises a housing having an open end for receiving the optical output end. In another example form, the optical diffuser comprises a housing having an open end for receiving a longitudinal portion of the optical waveguide. Preferably, the optical diffuser comprises a housing having an open end for receiving the optical output end and the longitudinal portion of the optical waveguide. In another example form, the device includes a temperature sensor. Preferably, the temperature sensor is interposed, or positioned or located, between a central longitudinal axis of the optical waveguide and an exterior surface of the housing, and optionally within the longitudinal extent of the longitudinal portion of the optical waveguide. According to another example aspect, there is provided a device for interstitial laser therapy comprising: an optical waveguide having an optical output end; an optical diffuser optically coupled to, or is optically associated with, or is positioned about, the optical output end, wherein the optical diffuser comprises an open end for receiving the optical output end; and a temperature sensor positioned internally of an exterior surface of the optical diffuser.

According to another example aspect, there is provided a device for interstitial laser therapy comprising: an optical waveguide extending along, or about, a central longitudinal axis and having an optical output end; an optical diffuser optically coupled to the optical output end, wherein the optical diffuser comprises a housing having an open end for receiving the optical output end and a longitudinal portion of the optical waveguide; and a temperature sensor interposed between the central longitudinal axis and an exterior surface of the housing within the longitudinal extent of the longitudinal portion of the optical waveguide. According to another example aspect, there is provided a system, with or without cooling fluid, for interstitial laser therapy comprising: one of the devices for interstitial laser therapy described above; a power-tunable optical source optically coupled to the optical waveguide; and a processing system configured to: obtain a temperature measurement from the temperature sensor; and adjust an optical output power of the optical source. According to other example aspects, the extent of and/or control of the ablation zone, leading to control of ablation, including for example the rate of ablation, can be controlled. For example, in a fixed laser power system, control of cooling fluid flow allows an operator to control the extent and/or rate of ablation. For example, in a fixed cooling fluid flow system, control of laser power allows an operator to control the extent and/or rate of ablation.

BRIEF DESCRIPTION OF FIGURES

Example embodiments are apparent from the following description, which is given by way of example only, of at least one non-limiting embodiment, described in connection with the accompanying figures.

FIG. 11 illustrates an example optical diffuser.

DETAILED DESCRIPTION

Figure 1:
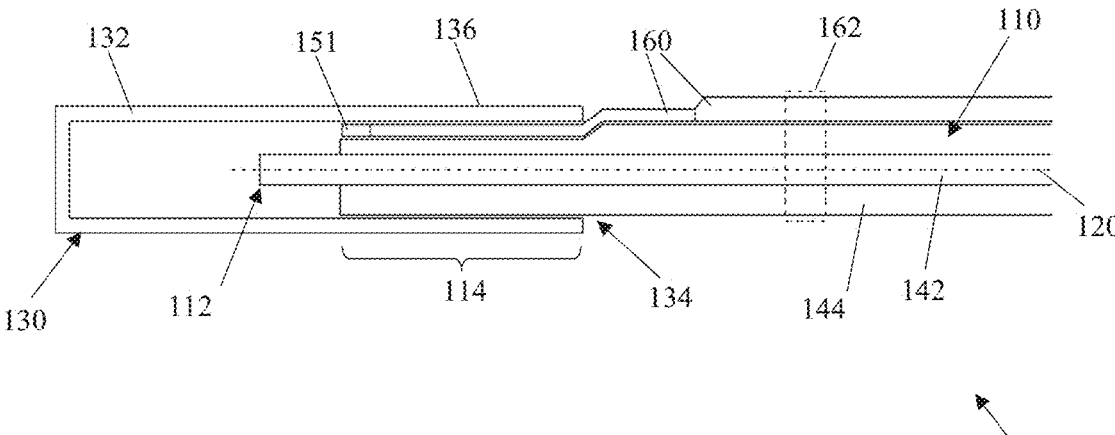
FIG. 1 illustrates a cross-sectional view of an example device for interstitial laser therapy, from a front-side perspective.

The following modes, given by way of example only, are described in order to provide a more precise understanding of the subject matter of an embodiment or embodiments. In the figures, incorporated to illustrate features of an example embodiment, like reference numerals are used to identify like parts throughout the figures. In the context of this specification, the term "about" is understood to refer to a range of numbers that a person of skill in the art would consider equivalent to the recited value in the context of achieving the same function or result.

Device for Interstitial Laser Therapy

Figure 2:
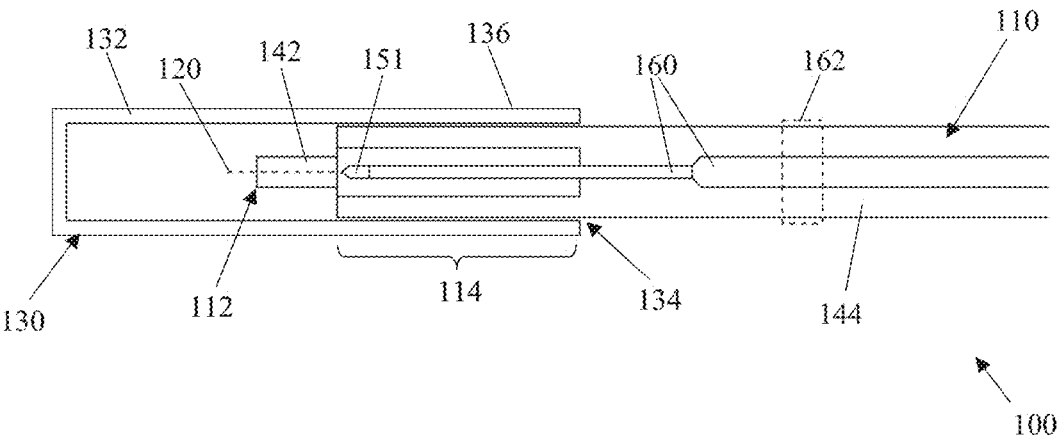
FIG. 2 illustrates a cross-sectional view of the device of FIG. 1, from a top-side perspective.

Referring to FIGS. 1 and 2, there is provided an example device 100 for interstitial laser therapy. Device 100 includes an optical waveguide 110 extending along, or about, a central longitudinal axis 120 and having an optical output end 112. Output end 112 is a distal end of optical waveguide 110. Device 100 further includes an optical diffuser 130 optically coupled to, or optically associated with, or positioned about, output end 112. Diffuser 130 includes, or is comprised of, a housing 132 having an open end 134 for receiving output end 112, and preferably for also receiving a longitudinal portion 114 of optical waveguide 110. Housing 132 has an exterior surface 136, for example being a circumferential exterior surface. Device 100 further includes a temperature sensor 151. Temperature sensor 151 is preferably positioned internally of exterior surface 136 of optical diffuser 130. In one example, temperature sensor 151 is interposed, or positioned, or located, between central longitudinal axis 120 and exterior surface 136, furthermore temperature sensor 151 is preferably, though not necessarily, also interposed, or positioned, or located, within the longitudinal extent of longitudinal portion 114 of optical waveguide 110. A temperature sensor could be a thermocouple or part of a thermocouple junction provided at a thermal mass component.

Central longitudinal axis 120 is an imaginary axis centred on, or coinciding to, a main path of propagation of electromagnetic waves in optical waveguide 110. In some examples, where optical waveguide 110 comprises multiple paths of propagation of electromagnetic waves, central longitudinal axis 120 is centred on, or coincides to, a central path of propagation of electromagnetic waves. Thus, in one example there is provided a device 100 for interstitial laser therapy comprising an optical waveguide 110 having an optical output end 112. An optical diffuser 130 is optically coupled to, or is optically associated with, or is positioned about, the optical output end 112, wherein the optical diffuser 130 comprises an open end 134 for receiving the optical output end 112. A temperature sensor 151 is positioned internally of an exterior surface 136 of the optical diffuser 130. The central longitudinal axis 120 does not intersect with, or pass through, first temperature sensor 151 (and/or a second temperature sensor, if provided, such as second temperature sensor 252 of FIG. 5). First temperature sensor 151 (and/or a second temperature sensor, if provided, such as second temperature sensor 252 of FIG. 5) is positioned apart from the optical output end 112. First temperature sensor 151 can be positioned adjacent to and/or abutting an internal surface of optical diffuser 130. Preferably, though not necessarily, optical waveguide 110 is an optical fibre, or is a plurality of optical fibres. Examples of suitable optical fibres include quartz optical fibres, although any other material suitable for propagation of electromagnetic waves may also be suitable, such as silica, fluoride glass, phosphate glass, chalcogenide glass, polymers, or any other material.

The dimensions of the optical fibre may vary depending on particular applications of device 100. In one example, the optical fibre has a diameter of about 600 μm and a divergence angle of about 8°. In other examples, the optical fibre may have any other suitable diameter size and divergence angle. These dimensions may depend on the size of the lesion or tumour requiring treatment. For example, when treating larger tumours, it may be preferable for the optical fibre to have a larger diameter size and/or a greater divergence angle spread since, with these characteristics, device 100 may achieve a larger thermal imprint and destruction of tissue over a wider area. In other examples, optical waveguide 110 may be any type of optical waveguide or collection of optical waveguides. Examples of suitable optical waveguides include but are not limited to: single mode fibres, multi-mode fibres, optical cables comprising one or more optical fibres, planar waveguides, and strip waveguides. Preferably, though not necessarily, optical waveguide 110 is capable of guiding electromagnetic waves having a wavelength, or range of wavelengths, in the visible (400 nm to 700 nm) and/or infrared (700 nm to 1 mm) spectra. In some examples, optical waveguide 110 is suitable for guiding electromagnetic waves having wavelengths in the range between about 890 nm and about 960 nm.

Optical waveguide 110 includes an inner layer 142 and an outer layer 144 radially surrounding inner layer 142. Inner layer 142 is for guiding electromagnetic waves (e.g. visible and/or infrared radiation) and comprises a core layer and a cladding layer (not shown) radially surrounding the core layer. Outer layer 144 is for protecting inner layer 142 and comprises a protective jacket. In other examples, optical waveguide 110 may have additional or fewer layers. For example, optical waveguide 110 may include two or more protective jacket layers, or it may have no projective jacket layer. Output end 112 is preferably stripped of outer layer 144. This may be advantageous for preventing outer layer 144 from being exposed to electromagnetic radiation, which may cause outer layer 144 to burn and damage optical waveguide 110. In some examples, output end 112 has a longitudinal length of about 1.7 mm. That is, optical waveguide 110 is stripped of outer layer 144 along a longitudinal portion extending from the tip of output end 112 for about 1.7 mm. In some examples, output end 112 has a longitudinal length extending between about 1 mm and about 2 mm. In other examples, output end 112, or a longitudinal portion of output end 112, may be stripped of outer layer 144 along any other longitudinal length. Alternatively, output end 112 may not be stripped of outer layer 144, or it may be partially stripped of outer layer 144, or only a radial portion of outer layer 144 may be stripped or shaved from output end 112. The tip, or longitudinal extremity, of output end 112 is cleaved or polished flat. In other examples, output end 112 may have an angled tip (i.e. cleaved at an angle relative to longitudinal axis 120), a cone tip, a ball tip, or any other geometry or termination configuration. Optical waveguide 110 may further include an optical input end (not shown) which is adapted to receive electromagnetic waves outputted from an optical source such as a laser or light-emitting diode (LED). The optical input end may be provided with a connector for coupling with an optical output port of the optical source. During operation, electromagnetic waves entering the optical input end propagate through optical waveguide 110 along its longitudinal axis 120 and exit from output end 112. Diffuser 130 is optically coupled to, or optically associated with, or positioned about, output end 112 such that electromagnetic waves exiting output end 112 propagate into diffuser 130. Electromagnetic waves entering diffuser 130 from output end 112 are diffused, scattered, or spread across the surface area of housing 132. The use of an optical diffuser improves the operation of device 100 for the purpose of interstitial laser therapy. Without the use of an optical diffuser, the energy outputted by an optical waveguide is typically concentrated in a narrow spot. Such high energy concentration can cause tissue in the vicinity of the output end of the waveguide to char or vaporize. While it is possible to create large thermal lesions in this manner, the morphology of the resulting lesion is highly unpredictable and not reproducible. The use of an optical diffuser causes the energy outputted by the optical waveguide to be distributed across a larger surface area, resulting in more tempered coagulation across larger volumes, while minimising or preventing charring of tissue. The use of an optical diffuser permits more consistent and predictable treatment procedures. Moreover, an optical diffuser limits denaturing of the optical waveguide tip. Preservation of the optical waveguide tip allows for repeated use of device 100, as well as enhancing its safety and accuracy.

In one example, housing 132 is cylindrical or tubular. In other examples, housing 132 may have any other geometry, such as conical. Moreover, diffuser 130 may be hollow or diffuser 130 may further include scattering material enclosed by housing 132 and forming a medium for scattering of electromagnetic waves entering diffuser 130. In another example, a diffuser may be constructed to diffuse over a sector of a cylinder, that is of variable angular aperture. For example, a diffuser may be constructed that diffuses laser light through a 180 degrees aperture resulting in a half cylinder ablation zone. In another example, a diffuser may be constructed that diffuses laser light through a 90 degrees aperture resulting in a quarter cylinder ablation zone. Such arrangements could be used for direction specific ablation of tissue. Housing 132 is preferably a tubular housing comprising an open end 134, a closed end opposite open end 134, and an exterior surface 136. Open end 134 is mechanically coupled to, or is fixed to, or is attached to, longitudinal portion 114. A longitudinal portion of housing 132 surrounds longitudinal portion 114 and clasps to, or embraces, or grips, or frictionally engages with, outer layer 144. In some examples, glue or other fastening mechanisms may be provided to mechanically couple, or fix, or attach, housing 132 to longitudinal portion 114. Housing 132 is defined by an inner diameter, being the diameter of a receptacle (i.e. the space for receiving output end 112 and longitudinal portion 114) of housing 132, and an outer diameter, being the diameter of exterior surface 136 of housing 132. The inner diameter of housing 132 is substantially equal to an outer diameter of optical waveguide 110. In this case, the outer diameter of housing 132 is greater than an outer diameter of optical waveguide 110, such that diffuser 130 bulges, or protrudes, radially outward relative to optical waveguide 110. In other examples, the outer diameter of housing 132 is approximately equal to the outer diameter of optical waveguide 110, such that diffuser 130 is level with optical waveguide 110. In this last example, housing 132 has a smaller inner diameter than the outer diameter of optical waveguide 110. Therefore, outer layer 144 of longitudinal portion 114 may need to be shaved, or partially stripped, so as to allow longitudinal portion 114 to be received into housing 132. An advantage of this last example is that the coupling of diffuser 130 to optical waveguide 110 does not increase the diameter of device 100. In yet other examples, the outer diameter of housing 132 may be less than the outer diameter of optical waveguide 110. Housing 132 is composed of a light-transmissive material to allow electromagnetic radiation scattered within diffuser 130 to radiate into a tissue being treated. Preferably, though not necessarily, housing 132 is composed of a heat resistant material (for example, a material having a low coefficient of thermal expansion), able to withstand temperatures up to at least about 100° C., or any maximum temperature that may be required for interstitial laser therapy. Preferably, though not necessarily, housing 132 comprises polytetrafluoroethylene (PTFE), also known as "Teflon". Advantageously, PTFE can be heat resistant up to about 300° C. In other examples, other light transmissive materials may compose housing 132, such polycarbonate, polyurethane, polyethylene, polypropylene, silicon, nylon, PVC, PET, ABS, PES, PEEK, FEP, as well as other flexible or rigid, radio-opaque or non radio-opaque materials as appropriate. An optical diffuser made from a heat-resistant material, such as PTFE, is advantageous since it enables coagulation of the tissue being treated without charring, and it protects the tip of the optical waveguide from melting or burning during treatment. Moreover, a heat-resistant diffuser removes the need for cooling systems for preserving the integrity of device 100. Therefore, device 100 need not include a cooling system.

Temperature sensor 151 is provided for measuring the temperature of a tissue being treated through interstitial thermal therapy by device 100. Therefore, device 100 allows for laser interstitial thermal therapy of tumours or tissues located in the liver, pancreas, prostate, brain, or any other location within a patient's body. In addition, device 100 allows for precise, direct, and fast measurement of absolute or relative temperatures of the tumour or tissue being treated. The temperature readings provided by temperature sensor 151 are useful for regulating the amount of radiation delivered to the tissue by device 100, and for obtaining or maintaining the necessary therapeutic tissue temperature. Temperature sensor 151 is interposed, radially interposed, or enclosed, or positioned, or located, between, or at least partially between, central longitudinal axis 120 and exterior surface 136 of housing 132. Preferably, temperature sensor 151 is also interposed, or positioned, or located, within the longitudinal extent of longitudinal portion 114 of the optical waveguide 110. In another example, temperature sensor 151 is positioned internally of exterior surface 136 of the optical diffuser 130. Central longitudinal axis 120 does not intersect with, or pass through, first temperature sensor 151. First temperature sensor 151 is positioned apart from, or away from, or does not abut, optical output end 112. First temperature sensor 151 can be positioned adjacent to and/or abutting an internal surface of optical diffuser 130. Longitudinal portion 114 is a longitudinal portion, segment, or section of waveguide 110, which is interior to housing 132 (i.e. housing 132 is mechanically coupled to longitudinal portion 114, or is mechanically coupled to at least part of longitudinal portion 114). The length of longitudinal portion 114 may vary depending on the internal structure of housing 132, into which longitudinal portion 114 is received. Preferably, though not necessarily, longitudinal portion 114 is directly adjacent to, or near, output end 112. In some examples, longitudinal portion 114 extends from a point of output end 112 stripped of outer layer 144.

Figure 3:
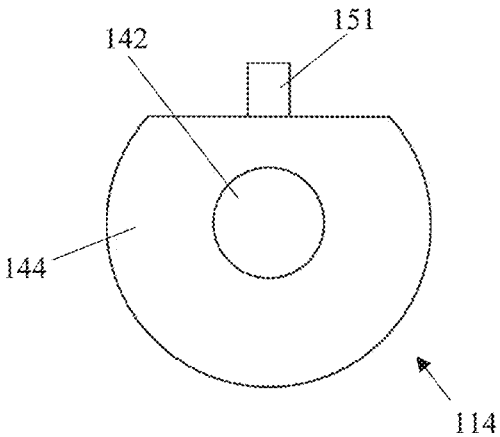
FIG. 3 illustrates a cross-sectional view of a longitudinal portion of the device of FIG. 1.
Figure 4:
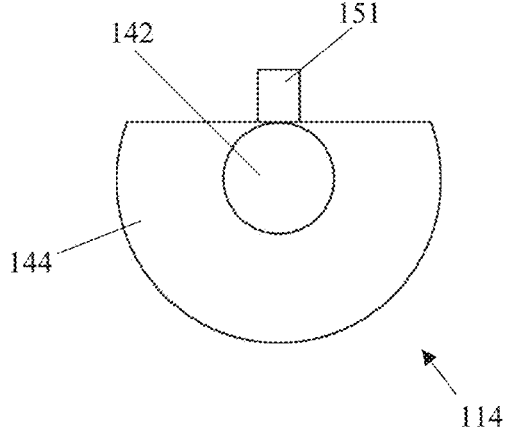
FIG. 4 illustrates a cross-sectional view of a longitudinal portion of an alternative embodiment of the device of FIG. 1.

In some examples, the length of longitudinal portion 114 is about 5 mm, meaning that the distance from an extremity of output end 112 stripped of outer layer 144 and a point of optical waveguide 110 near open end 134, is about 5 mm. In other examples, the length of longitudinal portion 114 is about 3 mm, or is about 4 mm, or is about 6 mm, or is about 7 mm, or is about 8 mm. In other examples, the length of longitudinal portion 114 is between about 1 mm and about 10 mm. In other examples, the length of longitudinal portion 114 is between about 2 mm and about 8 mm. In other examples, the length of longitudinal portion 114 is between about 3 mm and about 7 mm. In other examples, the length of longitudinal portion 114 is between about 4 mm and about 6 mm. In other examples, longitudinal portion 114 may have any suitable length. Longitudinal portion 114 is at least partially stripped of outer layer 144 for accommodating temperature sensor 151. A recess, groove, or indentation, is formed within outer layer 144 and temperature sensor 151 is arranged, located, or positioned within this recess. A cross-sectional view of longitudinal portion 114 is illustrated in FIG. 3, illustrating the profile of the recess, groove, or indentation for accommodating temperature sensor 151. Other recess profiles may also be used, for example, recess profiles that closely conform, or comport, to the profile of temperature sensor 151. In other examples, temperature sensor 151 is embedded within outer layer 144 of longitudinal portion 114. The recess for accommodating temperature sensor 151 may be formed by etching a portion, or slice, of outer layer 144 in longitudinal portion 114. The depth of the recess is such that temperature sensor 151 is in contact with, or attaches to, a remaining strip of outer layer 144 in longitudinal portion 114. In other examples, illustrated in FIG. 4, the depth of the recess is such that temperature sensor 151 is in contact with, or attaches to, an exposed portion of inner layer 142. For example, temperature sensor 151 may be in contact, or attached to, an exposed portion of a cladding or core layer of optical waveguide 110. The recess may therefore be formed by fully etching, or stripping, outer layer 144 along a segment of longitudinal portion 114. In some examples, the recess has a maximum depth of about 0.3 mm deep. In other examples, the recess has a maximum depth less than about 1 mm, or about 2 mm, or any other suitable maximum depth value.

In some examples, temperature sensor 151 may adhere to optical waveguide 110 with an adhesive, for example a cyanoacrylate-based adhesive. In other examples, any other mechanism of securely fixing or attaching temperature sensor 151 to optical waveguide 110 may be utilised. Preferably, though not necessarily, the depth of the recess is such that temperature sensor 151 does not project, or protrude, past the outer diameter, or outer extent, of optical waveguide 110. Preferably, though not necessarily, temperature sensor 151 is a micro-temperature sensor, or a temperature sensor having dimensions comporting with characteristic cross-sectional dimensions of optical waveguide 110. In some examples, the characteristic cross-sectional dimensions of optical waveguide 110 are in a millimetre or sub-millimetre range, such as between about 0.06 mm to about 0.1 mm. In some examples, temperature sensor 151 is an integrated temperature sensor, including an integrated circuit for the purpose of measuring temperature.

In some examples, temperature sensor 151 is a thermocouple or a microthermocouple, or is a thermocouple junction or a microthermocouple junction. In other examples, temperature sensor 151 is an infrared temperature sensor. In other examples, temperature sensor 151 is a fully integrated microelectromechanical system (MEMs) thermopile sensor capable of measuring the temperature of an object without having to be in direct contact, such as the Texas Instruments TMP006 or TMP006B infrared thermopile contactless temperature sensor. In other examples, other types of temperature sensors may be used, such as digital temperature sensors, analog temperature sensors, electrical temperature sensors, mechanical temperature sensors, thermistors, silicon bandgap temperature sensors, or any other type of temperature sensor. In further example embodiments, thermometry may be achieved by use of laser. An optical sensor could be used to measure reflected electromagnetic energy (back scatter). This could be a measured artefact of the glass to diffuser junction where such back scatter would occur.

In one example, temperature sensor 151 connects to electrical cable, or lead, 160 necessary for the operation of temperature sensor 151 (e.g. for powering temperature sensor 151 and/or for transmitting measurement data). Electrical cables 160 extend along optical waveguide 110 to reach an operator or system for operating device 100. Preferably, though not necessarily, cables 160 may be fastened to optical waveguide 110 to avoid them becoming tangled during operation of device 100. In some examples, fluorine tape windings 162 may fasten these electrical cables to optical waveguide 110. In other examples, other fastening mechanisms may be used. In other examples, temperature sensor 151 is a wireless temperature sensor, transmitting its temperature measurements by way of a wireless link. In some examples, temperature sensor 151 is a wireless temperature sensor that is powered wirelessly. An example wireless temperature sensor is that developed by the Mixed-Signal Microelectronics group at Eindhoven University of Technology, which is powered by radio waves that are part of a wireless network of the sensor. Further examples of suitable wireless temperature sensors may be found in the PhD thesis of Gao, H. (2015) "*Fully integrated ultra-low power mm-wave wireless sensor design methods*" Eindhoven: Technische Universiteit Eindhoven, and in the publication of Gao, H. et al., "*A 71 GHz RF energy harvesting tag with 8% efficiency for wireless temperature sensors in 65 nm CMOS*", Proceedings of the 2013 IEEE Radio Frequency Integrated Circuits Symposium (RFIC 2013), 2-4 June, Seattle, USA. Piscataway: Institute of Electrical and Electronics Engineers (IEEE), p. 403-406. In example embodiments where temperature sensor 151 is a wireless sensor, or in other examples where cables 160 are superfluous, cables 160 may not be included in device 100.

Preferably, though not necessarily, temperature sensor 151 is adapted to measure temperature external to optical diffuser 130. For example, where temperature sensor 151 is an infrared temperature sensor, its orientation should be set, or arranged, to detect an infrared energy spectrum of tissue being treated. Alternatively, temperature sensor 151 is adapted to measure a temperature external to optical diffuser 130 by measuring the temperature of optical diffuser 130. For example, optical diffuser 130 may be in contact with, or close proximity to, a tissue being treated, in which case optical diffuser 130 may be approximately in thermal equilibrium, or quasi-equilibrium, with the tissue. In general, it is not desirable for temperature sensor 151 to be exposed to electromagnetic radiation exiting output end 112. Such exposure may lead to temperature sensor 151 absorbing the electromagnetic radiation, causing damage or erroneous temperature measurements. To avoid this, temperature sensor 151 is arranged, positioned, or located on longitudinal portion 114, which is itself removed, offset, or displaced, from a path of propagation of electromagnetic waves exiting output end 112. In some examples, temperature sensor 151 is arranged, positioned, or located outside the range of electromagnetic exposure from output end 112. For example, temperature sensor 151 may be arranged further than a minimum distance from output end 112. In some examples, the position of temperature sensor 151 may be varied to prevent direct exposure to radiation depending on the operating conditions of device 100.

However, to enhance the accuracy of temperature measurements, it may be preferable to locate temperature sensor 151 as near as possible to tissue being irradiated by device 100. Therefore, in some examples, temperature sensor 151 should be as near as possible to output end 112 without being exposed to electromagnetic radiation exiting output end 112. In the example embodiment illustrated in FIGS. 1 and 2, temperature sensor 151 is arranged, positioned, or located at an extremity of longitudinal portion 114 near to, or in vicinity of, output end 112. In other examples, device 100 further includes electromagnetic shielding for protecting temperature sensor 151 from exposure to electromagnetic waves outputted by output end 112 and/or reflected or scattered from diffuser 130. In this way, the temperature measurement is not affected, or is minimally affected, by direct absorbance of electromagnetic energy by temperature sensor 151.

Figure 5:
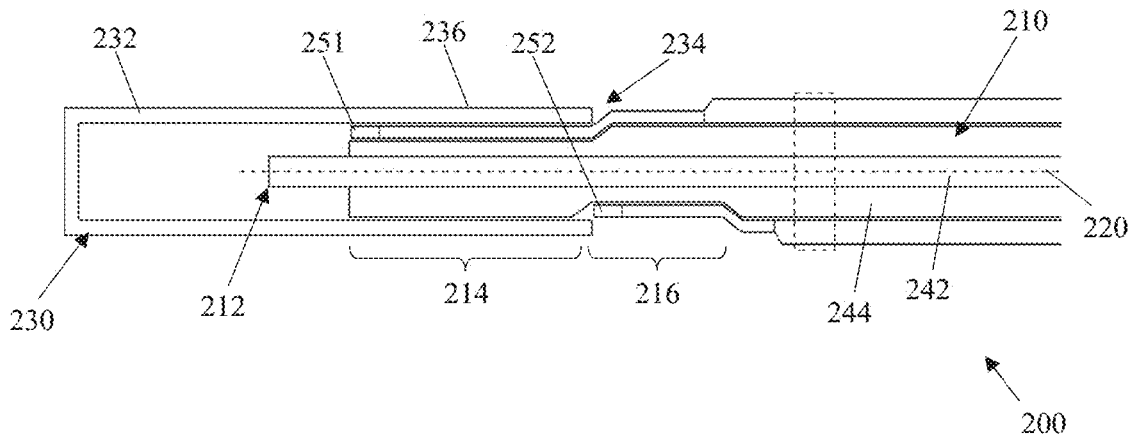
FIG. 5 illustrates a cross-sectional view of a further example device for interstitial laser therapy, from a front-side perspective.

Referring to FIG. 5, there is illustrated a further example device 200 for interstitial laser therapy. Device 200 includes an optical waveguide 210 extending along, or about, a central longitudinal axis 220 and having an optical output end 212. Device 200 further includes an optical diffuser 230 optically coupled to, or optically associated with, or positioned about, output end 212. Diffuser 230 includes a housing 232 having an open end 234 for receiving output end 212 and a first longitudinal portion 214 of optical waveguide 210. Device 200 further includes a first temperature sensor 251, interposed, positioned or located between longitudinal axis 220 and an exterior surface 236 of housing 232, within the longitudinal extent of the first longitudinal portion 214 of optical waveguide 210, and a second temperature sensor 252, attached to or fixed to optical waveguide 210. As previously, in another example, first temperature sensor 251 can be positioned internally of an exterior surface 236 of the optical diffuser 230. Preferably, though not necessarily, second temperature sensor 252 is arranged, positioned, or located on optical waveguide 210 and externally to optical diffuser 230. Second temperature sensor 252 is attached or fixed within a second longitudinal portion 216 of optical waveguide 210. Second temperature sensor 252 is arranged, positioned, or located adjacent to open end 234 of optical diffuser 230. Second temperature sensor 252 is longitudinally offset, or displaced from first temperature sensor 251. In some examples, first temperature sensor 251 and second temperature sensor 252 are longitudinally offset by about 5 mm. In some examples, first temperature sensor 251 and second temperature sensor 252 are longitudinally offset by between about 4 mm to about 6 mm, or by between about 3 mm to about 7 mm, or by between about 2 mm to about 8 mm. In other examples, any length of longitudinal offset may be used between first and second temperature sensors 251 and 252.

Moreover, although first temperature sensor 251 and second temperature sensor 252 are illustrated as being located on circumferentially opposite ends of optical waveguide 210, this is not necessary. In other examples, any relative circumferential displacement between first temperature sensor 251 and second temperature sensor 252 may be used. Central longitudinal axis 120 does not intersect with, or pass through, first temperature sensor 251 and/or second temperature sensor 252. First temperature sensor 251 and/or second temperature sensor 252 are/is positioned apart from optical output end 212. First temperature sensor 251 can be positioned adjacent to and/or abutting an internal surface of optical diffuser 230. Second temperature sensor 252 can be positioned outside the longitudinal extent of optical diffuser 230, i.e. within second longitudinal portion 216. Optical waveguide 210 includes an inner layer 242 and an outer layer 244 radially surrounding inner layer 242. Second longitudinal portion 216 is a longitudinal portion, segment, or section of optical waveguide 210, which is exterior to housing 232. Preferably, though not necessarily, second longitudinal portion 216 is in the immediate vicinity of, or directly adjacent to, housing 232. Second longitudinal portion 216 may have any longitudinal length, such as 1 mm, 2 mm, 3 mm, 4 mm, 5 mm, or any other length. Preferably, second longitudinal portion 216 does not overlap, or is not coextensive with, first longitudinal portion 214.

Figure 6:
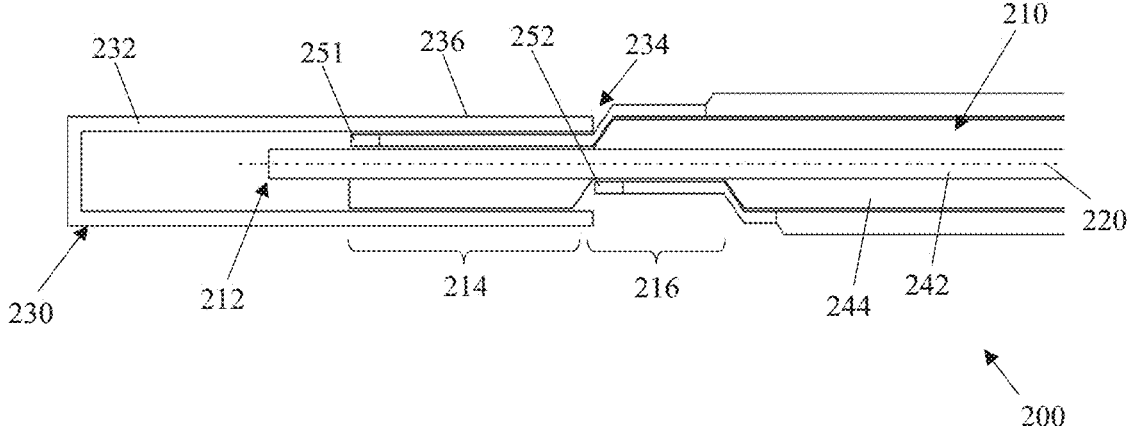
FIG. 6 illustrates a cross-sectional view of an alternative embodiment of the device of FIG. 5, from a front-side perspective.

Second longitudinal portion 216 is at least partially stripped of outer layer 244 for accommodating second temperature sensor 252. A recess, groove, or indentation, is formed within outer layer 244 and second temperature sensor 252 is arranged, located, or positioned within this recess. In other examples, second temperature sensor 252 is embedded within outer layer 244 of second longitudinal portion 216. The recess for accommodating second temperature sensor 252 may be formed by etching a portion, or slice, of outer layer 244 in second longitudinal portion 216. The depth of the recess is such that second temperature sensor 252 is in contact with, or attaches to, a remaining strip of outer layer 244 in second longitudinal portion 216. In other examples, illustrated in FIG. 6, the depth of the recess is such that second temperature sensor 252 is in contact with, or attaches to, an exposed portion of inner layer 242. As illustrated in FIG. 6, first temperature sensor 251 may also be in contact with, or attached to, an exposed portion of inner layer 242. That is, the recesses for accommodating first and second temperature sensors 251 and 252 may be formed by fully etching, or stripping, outer layer 244 along segments of first and second longitudinal portions 214 and 216. In some examples, the recess has a maximum depth of about 0.3 mm deep. In other examples, the recess has a maximum depth less than about 1 mm. In other examples, the recess may have any other maximum depth value. In other examples, second temperature sensor 252 is arranged, located, or positioned within a cladding layer of inner layer 242, without obstructing the propagation of electromagnetic waves in a core layer of inner layer 242.

In some examples, second temperature sensor 252 may be attached to optical waveguide 210 with an adhesive, for example a cyanoacrylate based adhesive. In other examples, any other mechanism of securely fixing or attaching second temperature sensor 252 to optical waveguide 210 may be utilised. Preferably, though not necessarily, the depth of the recess is such that second temperature sensor 252 does not project, or protrude, past the outer diameter of optical waveguide 210. Preferably, though not necessarily, second temperature sensor 252 is a micro-temperature sensor, or a temperature sensor having dimensions comporting with characteristic cross-sectional dimensions of optical waveguide 210 (e.g. millimetre or sub-millimetre). In some examples, second temperature sensor 252 is an integrated temperature sensor, including an integrated circuit for the purpose of measuring temperature. In some examples, second temperature sensor 252 is a thermocouple or a microthermocouple. In other examples, second temperature sensor 252 is an infrared temperature sensor. In other examples, second temperature sensor 252 is a fully integrated microelectromechanical system (MEMs) thermopile sensor capable of measuring the temperature of an object without having to be in direct contact, such as the Texas Instruments TMP006 or TMP006B infrared thermopile contactless temperature sensor. In other examples, other types of temperature sensors may be used, such as digital temperature sensors, analog temperature sensors, electrical temperature sensors, mechanical temperature sensors, thermistors, silicon bandgap temperature sensors, or any other type of temperature sensor. In other examples, second temperature sensor 252 is a wireless temperature sensor, transmitting its temperature measurements by way of a wireless link. In some examples, second temperature sensor 252 is a wireless temperature sensor that is powered wirelessly, as previously described herein. Furthermore, in some examples, second temperature sensor 252 is of a same type or kind as first temperature sensor 251. For example, both first temperature sensor 251 and second temperature sensor 252 may be microthermocouples. In other examples, second temperature sensor 252 is of a different type or kind compared to first temperature sensor 251. For example, first temperature sensor 251 may be an infrared temperature sensor and second temperature sensor 252 may be a microthermocouple. In other examples, first temperature sensor 251 and second temperature sensor 252 may have the same or different operational characteristics (e.g. temperature measurement range, measurement resolution) and ratings.

During operation of device 200, first temperature sensor 251 and second temperature sensor 252 measure or sense different temperatures. First temperature sensor 251 is provided to measure a temperature of a tissue being irradiated for the purpose of interstitial laser therapy, while second temperature sensor 252 is provided to measure temperatures of other objects and/or tissues. Since second temperature sensor 252 is offset from diffuser 230, it is not adapted to measure a temperature of a tissue being irradiated. In some examples, second temperature sensor 252 is adapted to measure a temperature external to optical diffuser 230. In some examples, second temperature sensor 252 provides a reference, or baseline, temperature reading. For example, second temperature sensor 252 may measure the temperature of a tissue adjacent to, surrounding, or in the vicinity of a tissue being treated. The temperature measurement of first temperature sensor 251 may then be considered relative to the temperature measurement of second temperature sensor 252. For example, device 200 may provide a measure of a temperature gradient, or difference, between first temperature sensor 251 and second temperature sensor 252. In some examples, first temperature sensor 251 and second temperature sensor 252 are adapted to measure a temperature difference. In other examples, second temperature sensor 252 may be used to monitor temperatures of tissues which should not be heated during interstitial thermal therapy. For example, second temperature sensor 252 enables an operator to monitor the temperature of healthy tissue surrounding a tumour being treated, and to make appropriate adjustments in case the temperature of the healthy tissue surpasses a certain safe level. Alternatively, second temperature sensor 252 provides a backup, redundant, or alternative temperature sensor in case first temperature sensor 251 becomes unusable or faulty during treatment procedures. In other examples, device 200 may include additional temperature sensors, such as three, four, or more temperature sensors.

Figure 7:
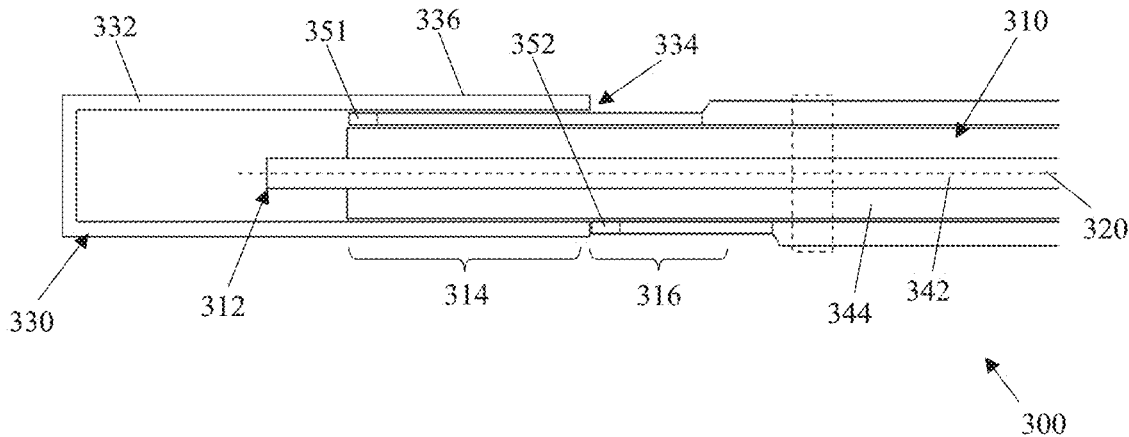
FIG. 7 illustrates a cross-sectional view of a further example device for interstitial laser therapy, from a front-side perspective.

Referring to FIG. 7, there is illustrated a further example device 300 for interstitial laser therapy. Device 300 includes an optical waveguide 310 extending along, or about, a central longitudinal axis 320 and having an optical output end 312. Device 300 further includes an optical diffuser 330 optically coupled to, or optically associated with, or positioned about, output end 312. Diffuser 330 includes a housing 332 having an open end 334 for receiving output end 312 and a first longitudinal portion 314 of optical waveguide 310. Housing 332 has an exterior surface 336. Device 300 further includes a first temperature sensor 351, interposed, positioned or located between central longitudinal axis 320 and exterior surface 336 within the longitudinal extent of first longitudinal portion 314 of optical waveguide 310, and a second temperature sensor 352, fixed to optical waveguide 310. As previously, in another example, first temperature sensor 351 can be positioned internally of an exterior surface 336 of the optical diffuser 330. Optical waveguide 310 includes an inner layer 342 and an outer layer 344 radially surrounding inner layer 342. First temperature sensor 351 is fixed to outer layer 344 of first longitudinal portion 314. Second temperature sensor 352 is fixed within a second longitudinal portion 316 of optical waveguide 310. Second temperature sensor 352 is fixed to outer layer 344 of second longitudinal portion 316. First and second longitudinal portions 314 and 316 are not stripped, or shaved, of outer layer 344. This configuration may facilitate manufacturing, or assembling, of device 300. Housing 332 should be provided with an inner diameter which exceeds an outer diameter of optical waveguide 310, in order to accommodate first temperature sensor 351.

Figure 8:
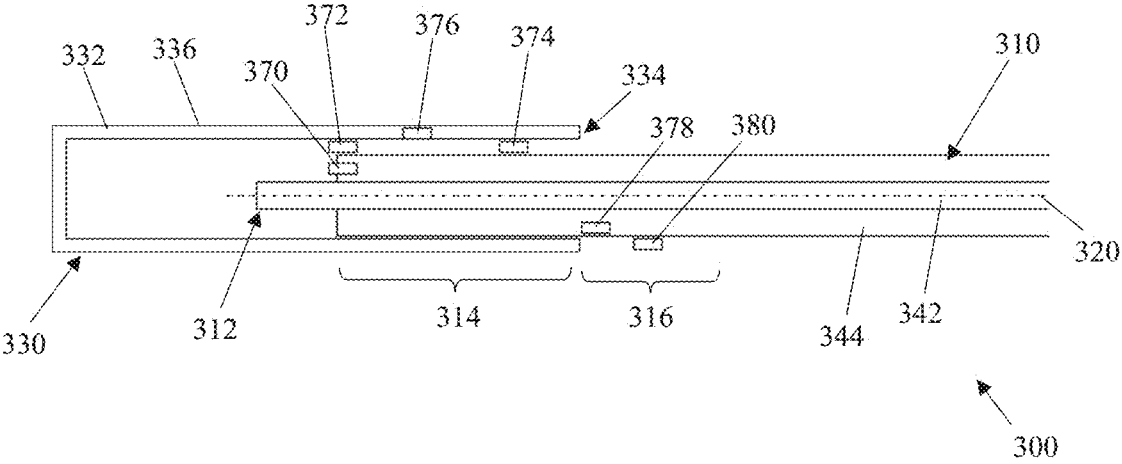
FIG. 8 illustrates a simplified schematic of the device of FIG. 7, showing various placements for a first temperature sensor and a second temperature sensor.

Referring to FIG. 8, there is illustrated a simplified schematic of device 300 showing various, alternative points or positions, where a first temperature sensor and a second temperature sensor, or additional temperature sensors, may be arranged, positioned, embedded or located, either individually or collectively. In one example, first temperature sensor 370 is embedded in outer layer 344 of first longitudinal portion 314, and is partially exposed towards, or in the vicinity of, output end 312. In another example, the first temperature sensor may be completely embedded in outer layer 344. In another example, first temperature sensor 372 is positioned on outer layer 344 of first longitudinal portion 314, and projects, or protrudes towards output end 312. In another example, first temperature sensor 374 is positioned on outer layer 344 of first longitudinal portion 314, and is displaced from an extremity of first longitudinal portion 314 nearest to output end 312. For example, first temperature sensor 364 may be positioned in the vicinity of open end 334. In another example, first temperature sensor 376 is positioned within a groove, recess, or cavity of housing 332. In other examples, outer layer 344 and housing 332 may both be provided with a corresponding groove, recess, or cavity for accommodating first temperature sensor 376. In other examples, the first temperature sensor may be embedded, positioned, arranged, or located within a cladding layer of inner layer 342 in first longitudinal portion 314, and arranged without obstructing the propagation of electromagnetic waves in a core layer of inner layer 342.

In one example, second temperature sensor 378 is embedded in outer layer 344 of second longitudinal portion 316. In other examples, second temperature sensor 378 may be only partially embedded in outer layer 344 of second longitudinal portion 316. In another example, second temperature sensor 380 is positioned on outer layer 344 of second longitudinal portion 316, and is offset, displaced, or removed from housing 332 and open end 334. The distance between second temperature sensor 380 and open end 334 may vary in various embodiments. In other examples, the second temperature sensor may be embedded, positioned, arranged, or located within a cladding layer of inner layer 342 in second longitudinal portion 316, and arranged without obstructing the propagation of electromagnetic waves in a core layer of inner layer 342. In various further examples, two or more of any of the first temperature sensors 351, 370, 372, 374 and 376 can be used. In another example, two or more of any of the second temperature sensors 352, 378 and 380 can be used.

System for Interstitial Laser Therapy

Figure 9:
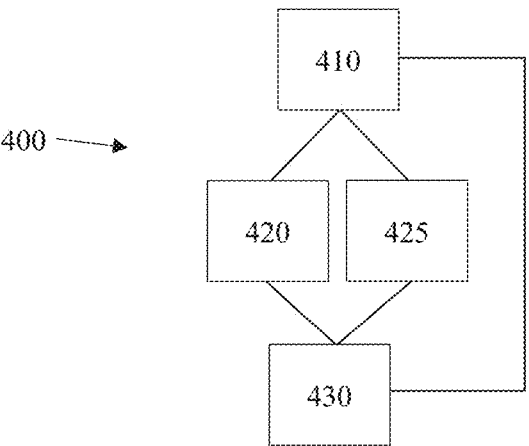
FIG. 9 illustrates an example system for interstitial laser therapy.

Referring to FIG. 9, there is illustrated an example system 400 for interstitial laser therapy. System 400 comprises a device 410 for interstitial laser therapy, as described in any of the previous examples. System 400 further comprises either or both of (i) a power tunable optical source 420 optically coupled to an input end of an optical waveguide of device 410 and/or (ii) a flow controller 425 providing controllable flow of cooling fluid, and a processing system 430. Flow controller 425 could be a driving pump that is pumping the cooling fluid, or a flow regulator in the fluid line of the cooling fluid. This produces changes in, i.e. control of, the ablation zone and resulting control over the ablation of tissue. Processing system 430 is configured to obtain one or more temperature measurements from one or more temperature sensors of device 410, and to adjust either or both of (i) an optical output power of optical source 420 and/or a flow rate of cooling fluid by control of flow controller 425. Processing system 430 can control optical power of optical source 420 and/or cooling fluid flow rate of flow controller 425 to create variations in the ablation zone. The extent of and/or control of the ablation zone, leading to control of ablation of tissue, including for example the rate of ablation, can be controlled by optical source 420 and/or flow controller 425, which can be varied simultaneously, or separately while one is fixed. For example, a fixed laser power system could be provided with control of cooling fluid flow, or a fixed cooling fluid flow system could be provided with control of laser power, or a system with both variable laser power and variable cooling fluid flow could be provided, thereby allowing an operator to control the extent and/or rate of ablation.

Optical source 420 delivers an optical signal to the optical waveguide and permits the tuning, or adjustment, of the optical signal's power. In some examples, optical source 420 is a laser or an LED, or other device capable of generating an optical signal. In other examples, optical source 420 is a power-tunable active device, such as an amplifier, or a power tunable passive device, such as an attenuator or tunable coupler, which relays an optical signal (generated from another optical source) to the optical waveguide of device 410. In some examples, processing system 430 receives, or obtains, the one or more temperature measurements directly from the one or more temperature sensors of device 410. In other examples, processing system 430 receives, or obtains, the one or more temperature measurements from one or more peripheral devices connected to the one or more temperature sensors, where the peripheral devices calculate the temperatures of one or more tissues being treated based on sensor data acquired from the one or more temperature sensors. Example peripheral devices include voltmeters, power meters, spectrometers, or any other instrument for interpreting sensor data and converting it to a temperature measurement. In yet other examples, processing system 430 calculates the temperature of the tissue being treated based on sensor data acquired from the one or more temperature sensors.

Processing system 430 relies on the temperature measurement to determine how to adjust the output optical power of optical source 420. In some examples, processing system 430 may rely on additional information, or data, in determining how to adjust the output optical power of optical source 420. This additional information may include the size and dimensions of a tumour being treated, as well as the type of tissue of the tumour. This information may be determined using medical imaging devices prior to treatment commencing. In some examples, processing system 430 may rely on data tables including optical power/energy requirements, exposure/radiation times, and optical wavelength requirements for particular tissues or tumours in determining how to adjust the output optical power of optical source 420. System 400 may further include a channel for delivering device 410 to a treatment region. Examples for a channel include a catheter, a cannula, a tube, or any other channel depending on the location of the tumour or tissue being treated (for example, liver, pancreas, prostate, brain, or any other location within a patient's body). The channel may be inserted into the body of a patient. Device 410 would be inserted into the channel, with a diffuser of device 410 as the leading portion, and with the optical waveguide of device

410 being subsequently fed through the channel. The channel would thus guide device 410 to the treatment region.

In a further example, the channel, i.e. the cannula, can be provided with a clear end portion and/or a closed trocar tip (or other type of sharp-pointed instrument). A cannula with a clear end portion allows for laser energy and/or heat to be transmitted out from the cannula into the tissue. Traditional trocars are solid, and are commonly formed of opaque plastic or metal. Traditional trocars also do not have a closed end. In one example, a trocar is used that has a sharp end which can be used to penetrate tissues like a normal cannula. The sharp end can cut and pierce tissue and/or skin. The end portion of the channel, i.e. the cannula, is preferably made of a transparent material, an optically clear material or an optically semi-opaque material. Optionally, the complete length of the cannula can be made of the same material (the transparent material, the optically clear material or the optically semi-opaque material). That is, at least in some examples, at least an end portion of the channel, i.e. the cannula, is transparent or semi-opaque. These examples allow laser energy and/or heat to penetrate through the walls of the cannula into surrounding tissues. In another optional form, the cannula also can be provided with an irrigation outlet and an irrigation inlet if used with an irrigation fluid.

System 400 may further include an imaging device for locating device 410 as it is being delivered to the treatment region. Example imaging devices include MRI scanners, ultrasound scanners, or other echolocation scanners. An advantage of device 410 is that it is able to measure the temperature of a tissue being treated without the need for additional diagnostic devices. This allows for the use of a simpler imaging device, such as an ultrasound scanner which is normally not able to measure temperature, for locating device 410 during therapy. Advantageously, system 400 provides a feedback mechanism which enables accurate monitoring of the temperature level of a tumour or tissue being treated and adjustment of this temperature level, for example by means of adjusting the output optical power delivered to the tumour or tissue and/or by means of adjusting a rate of cooling fluid flow. This feedback procedure can be executed in real time (or with low latency) due to the reduced complexity of the elements used. That is, it is no longer necessary to employ highly complex MRI scanners to merely estimate the temperature. A measured temperature difference between two areas can be used to provide an estimator of the uniformity of an ablation zone where ablation of tissue occurs. Measures of temperature can be used to provide feedback parameters for control of laser power and/or control of cooling fluid flow, for example by control of a fluid driving pump or fluid flow regulator.

Processing System

Figure 10:
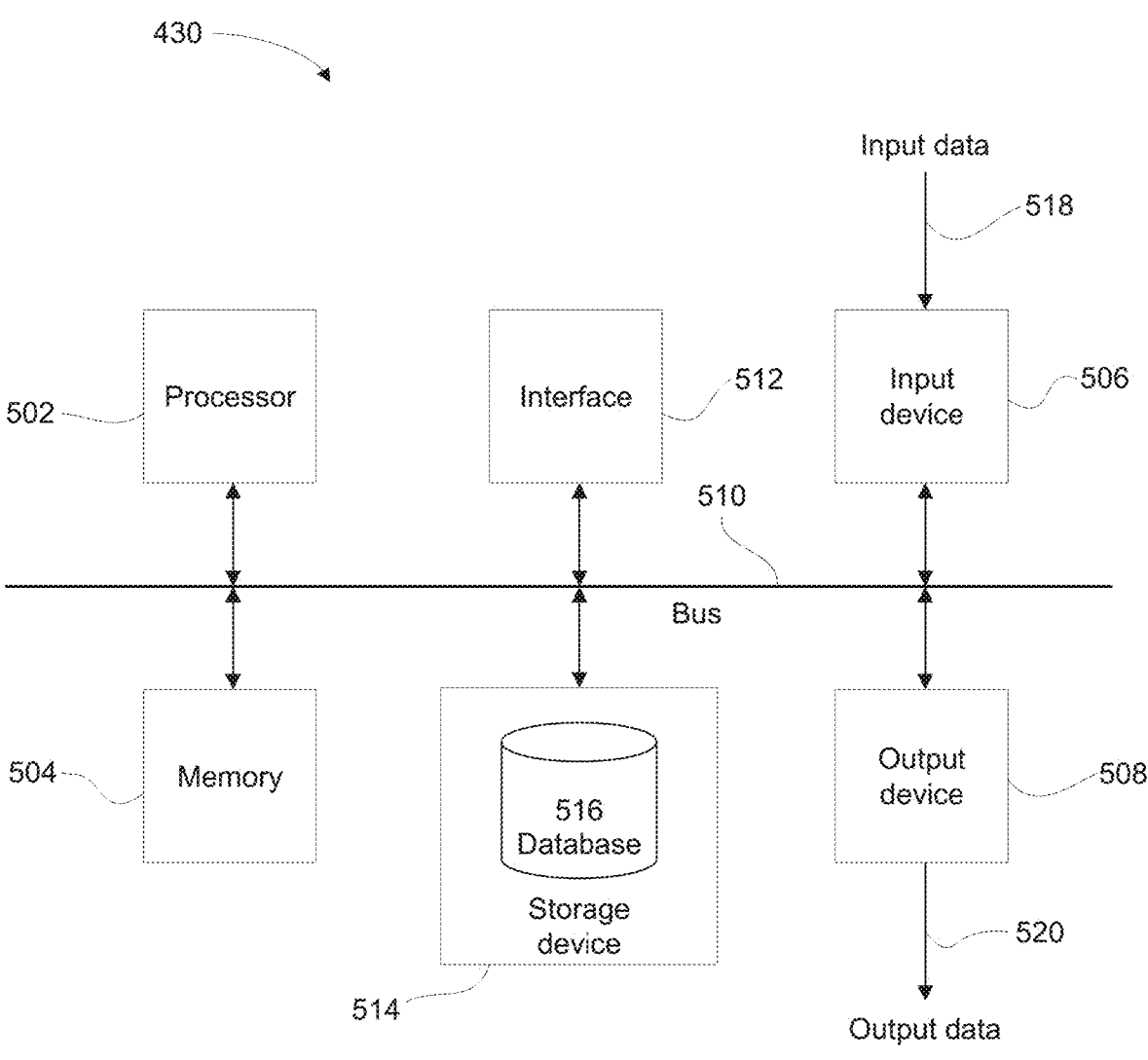
FIG. 10 illustrates an example processing system for use in the system of FIG. 9.
Figure 111:
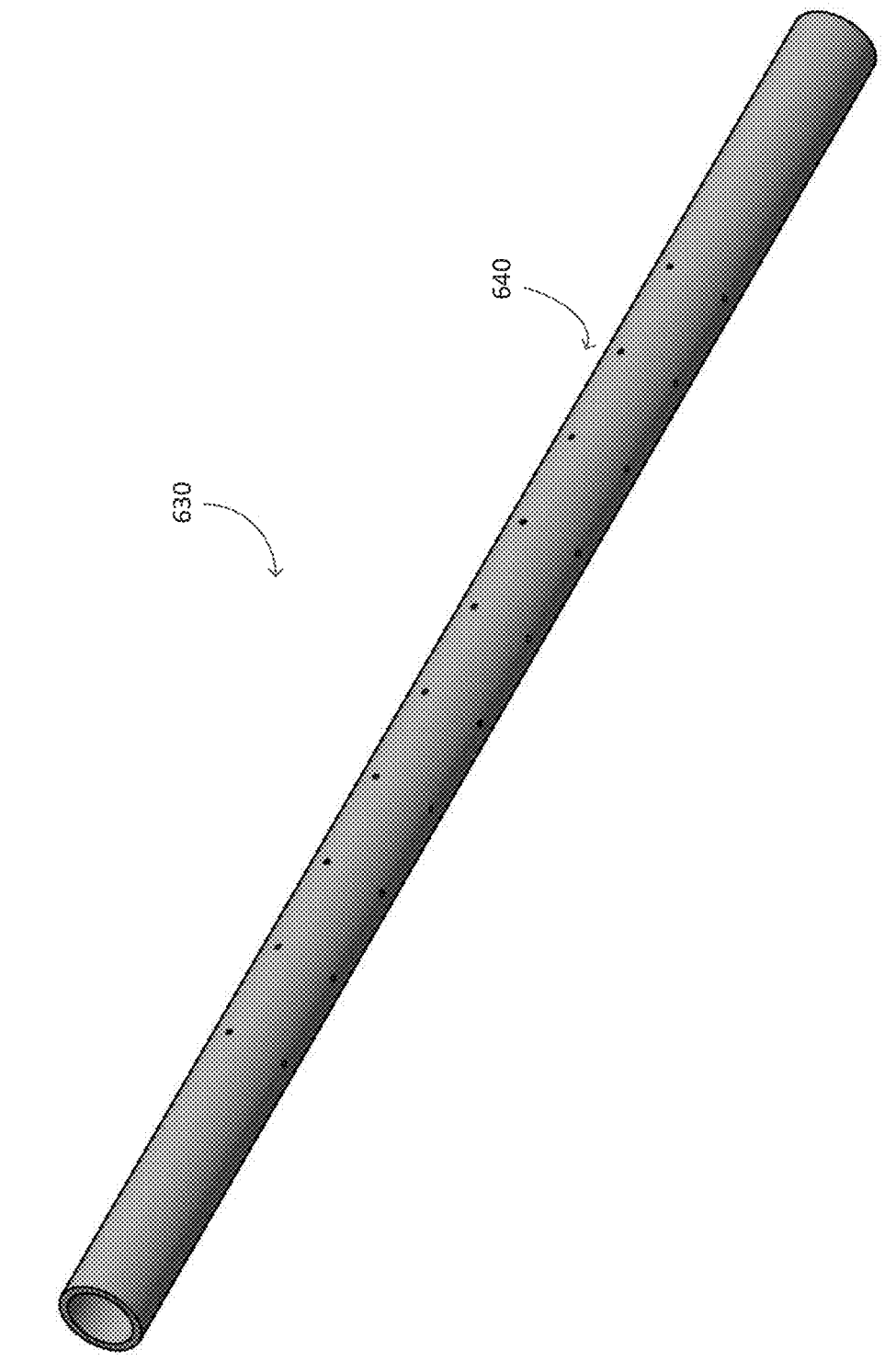

Referring to FIG. 10, there is illustrated an example processing system 430. In particular, the processing system 430 generally includes at least one processor 502, or processing unit or plurality of processors, memory 504, at least one input device 506 and at least one output device 508, coupled together via a bus or group of buses 510. In certain embodiments, input device 506 and output device 508 could be the same device. An interface 512 can also be provided for coupling the processing system 430 to one or more peripheral devices, for example interface 512 could be a PCI card or PC card. At least one storage device 514 which houses at least one database 516 can also be provided. The memory 504 can be any form of memory device, for example, volatile or non-volatile memory, solid state storage devices, magnetic devices, etc. The processor 502 could include more than one distinct processing device, for example to handle different functions within the processing system 430. Input device 506 receives input data 518, for example temperature readings or data from one or more of the temperature sensors, and can include, for example, a keyboard, a pointer device such as a pen-like device or a mouse, audio receiving device for voice controlled activation such as a microphone, data receiver or antenna such as a modem or wireless data adaptor, data acquisition card, etc. Input data 518 could come from different sources, for example keyboard instructions in conjunction with data received via a network. Output device 508 produces or generates output data 520 and can include, for example, a display device or monitor in which case output data 520 is visual, a printer in which case output data 520 is printed, a port for example a USB port, a peripheral component adaptor, a data transmitter or antenna such as a modem or wireless network adaptor, or data sent to control or adjust the output optical power of optical source 420, etc. Output data 520 could be distinct and derived from different output devices, for example a visual display on a monitor in conjunction with data transmitted to a network. A user could view data output, or an interpretation of the data output, on, for example, a monitor or using a printer. The storage device 514 can be any form of data or information storage means, for example, volatile or non-volatile memory, solid state storage devices, magnetic devices, etc.

In use, the processing system 430 is adapted to allow data or information to be stored in and/or retrieved from, via wired or wireless communication means, the at least one database 516. The interface 512 may allow wired and/or wireless communication between the processing unit 502 and peripheral components that may serve a specialised purpose. The processor 502 receives instructions as input data 518 via input device 506 and can display processed results or other output to a user by utilising output device 508. More than one input device 506 and/or output device 508 can be provided. It should be appreciated that the processing system 430 may be any form of terminal, server, specialised hardware, or the like.

Optical Diffuser

The following examples provide a more detailed discussion of particular embodiments. The examples are intended to be merely illustrative and not limiting to the scope of the present invention.

In any of the examples previously discussed herein, the diffuser, or a part of the diffuser, can be, optionally, additionally provided with one or more apertures, for example as one or more holes, one or more slits, one or more openings, and/or one or more vents. For example, one or more apertures, one or more holes, slits, openings and/or vents can be used to enable a better diffusion of the electromagnetic energy, e.g. laser energy, out from the laser fibre. This advantageously results in a reduction in damaging the diffuser tip as well as better penetration of energy into the tissues. Traditionally, laser diffuser tips are solid and clear or semi-opaque to enable the laser energy diffuse out. This causes heating of the diffuser. The diffuser can overheat and disintegrate as a result of the laser energy power. The tissue to which the laser energy is delivered may also tend to char and burn, rather than more gradually heat-up and allow the energy to penetrate into the tissue. In further examples, the one or more holes, the one or more slits, the one or more openings, and/or the one or more vents in the diffuser additionally allow gases generated from the tissue being heated to escape out, diffuse out, or vent, from the inside region of the diffuser, and again enable a more consistent energy transfer into the tissue. That is, in use generated gases escape out from an inside region of the optical diffuser via the one or more holes, the one or more slits, the one or more openings, and/or the one or more vents. A particular advantageous use of an "open", "non-solid", or "semi-closed" diffuser is that if used with irrigation solution to cool the diffuser, the irrigation solution has a much better and easier access to the diffuser. This allows the diffuser to be cooled more efficiently and enables higher laser power to be used without causing damage to the diffuser or resulting in charring or burning of the tissue. Additionally, this can also simultaneously allow gases released from heating of the tissue, or from the irrigation solution, to escape out, diffuse out, or vent, more readily from the inside region of the diffuser. A variety of types, shapes, number, orientations and/or configurations of one or more apertures, one or more holes, one or more slits, one or more openings, and/or one or more vents can be utilised.

Referring to FIG. 11, there is shown an example optical diffuser, preferably being a cylindrical optical diffuser 630 (or a tubular optical diffuser). The relative length, thickness and diameter of optical diffuser 630 is provided by way of example only, as is the orientation, location and extent of one or more holes 640. One or more holes 640, i.e. one or more apertures, one or more openings and/or one or more vents, are provided along at least part of the longitudinal length of optical diffuser 630, and at different circumferential positions, and pass through the housing of optical diffuser 630 to extend from an exterior surface to an interior surface of optical diffuser 630.

Figure 12:
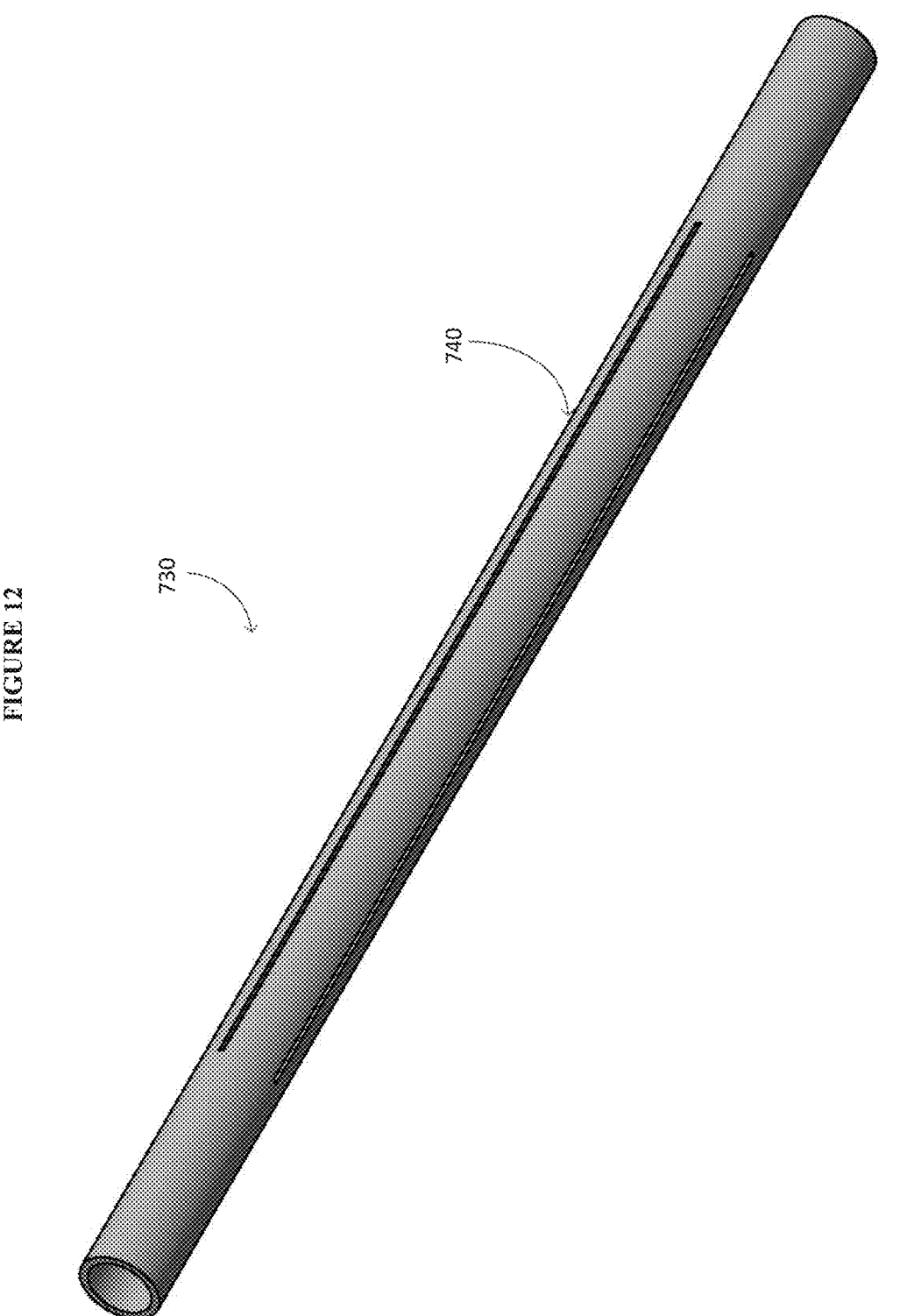
FIG. 12 illustrates another example optical diffuser.

Referring to FIG. 12, there is illustrated another example optical diffuser 730 provided with one or more slits 740, i.e. one or more apertures 740, one or more openings 740 and/or one or more vents 740. One or more slits 740, i.e. one or more apertures, one or more openings and/or one or more vents, are provided along at least part of the longitudinal length of optical diffuser 730, and at different circumferential positions, and pass through the housing of optical diffuser 730 to extend from an exterior surface to an interior surface of optical diffuser 730. More than one slit can be provided along a longitudinal length of optical diffuser 730. It should be appreciated that the one or more apertures, one or more holes, one or more slits, one or more openings and/or one or more vents, illustrated by way of example in FIGS. 11 and 12, can be provided along any length, portion, extent or circumference of the example diffusers. A variety of different types of apertures, holes, slits, openings and/or vents can be provided. Similarly, a variety of different shapes of apertures, holes, slits, openings and/or vents can be provided. Additionally, any number of apertures, holes, slits, openings and/or vents can be provided as part of a diffuser. Additionally, a variety of orientations for apertures, holes, slits, openings and/or vents can be provided as part of a diffuser. Additionally, a variety of configurations of a mixture of apertures, holes, slits, openings and/or vents can be provided as part of a diffuser.

As illustrated by way of example in FIGS. 11 and 12, one or more apertures, one or more holes, one or more slits, one or more openings and/or one or more vents can be positioned about the circumference of a diffuser, as well as being positioned along at least part of a longitudinal extent or length of the diffuser. Any desired number of apertures, holes, slits, openings and/or vents can be positioned about the circumference with any desired angular spacing. As non-limiting examples, provided by way of indication only, apertures, holes, slits, openings and/or vents may have a length or diameter of from about 0.1 mm to about 10 mm. Apertures, holes, slits, openings and/or vents could be spaced apart for example by about 0.5 mm to about 10 mm. Longitudinally extending lines or patterns of apertures, holes, slits, openings and/or vents can be spaced about 90 degrees apart circumferentially, assuming four longitudinally extending lines or patterns are desired. Longitudinally extending lines or patterns of apertures, holes, slits, openings and/or vents can be spaced about 120 degrees apart circumferentially, assuming three longitudinally extending lines or patterns are desired. Longitudinally extending lines or patterns of apertures, holes, slits, openings and/or vents can be spaced about 180 degrees apart circumferentially, assuming two longitudinally extending lines or patterns are desired. In another example, one longitudinally extending line or pattern of apertures, holes, slits, openings and/or vents is provided, assuming one longitudinally extending line or pattern is desired.

Figure 13:
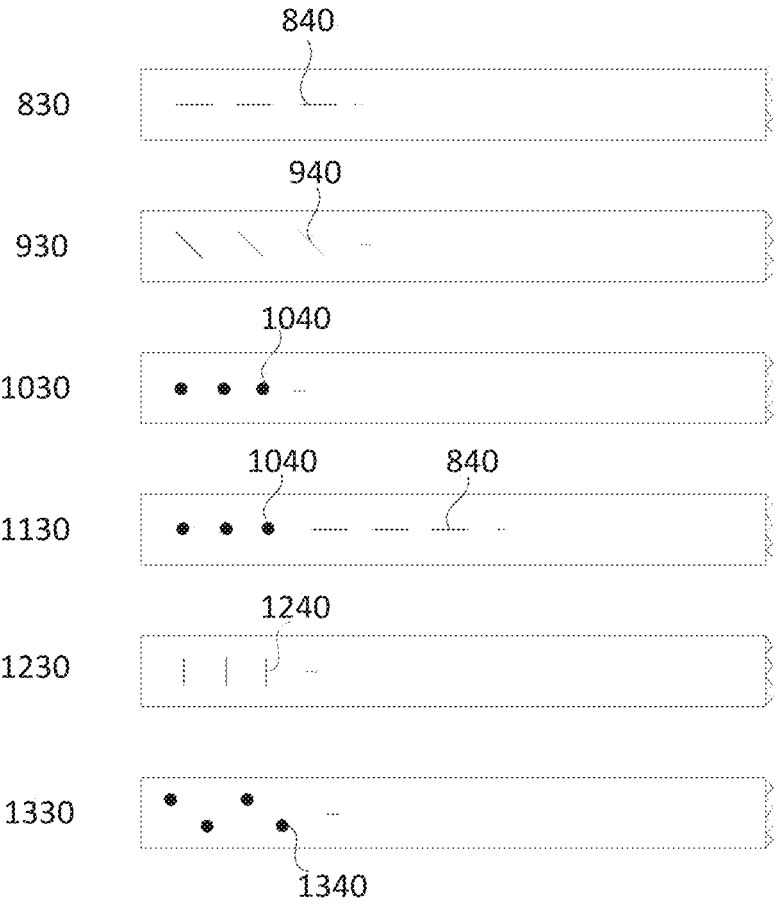
FIG. 13 illustrates further example optical diffusers.

Referring to FIG. 13, there are illustrated side-views of further example optical diffusers 830, 930, 1030, 1130, 1230, 1330, having different example types, shapes, orientations and/or configurations of apertures, holes, slits, openings and/or vents. The example optical diffusers are illustrated as being of indefinite longitudinal extent. The example optical diffusers are tube shaped or cylindrical in three-dimensions. Diffuser 830 includes one or more longitudinally aligned slits or vents 840. Diffuser 930 includes one or more angled slits or vents 940. Diffuser 1030 includes one or more apertures, holes or vents 1040. Diffuser 1130 includes a combination of one or more apertures, holes or openings together with one or more slits 840. The configuration, orientation and/or arrangement of different shapes of apertures, holes, openings, vents or slits can be significantly varied. Diffuser 1230 includes perpendicularly aligned one or more slits 1240. Diffuser 1330 includes one or more apertures, holes or openings 1340 that are offset at different or periodic circumferential (or radial) angles at least partially along the longitudinal extent or length of diffuser 1330. It should be realised that the number of apertures, holes, slits, openings and/or vents shown in example diffusers is for illustration only and any number can be utilised, for example one, two, three, four, five, six, seven, eight, nine, ten, etc. apertures, holes, slits, openings and/or vents can be utilised, or any combination thereof.

Further Examples—System for Interstitial Laser Therapy

Figure 14:
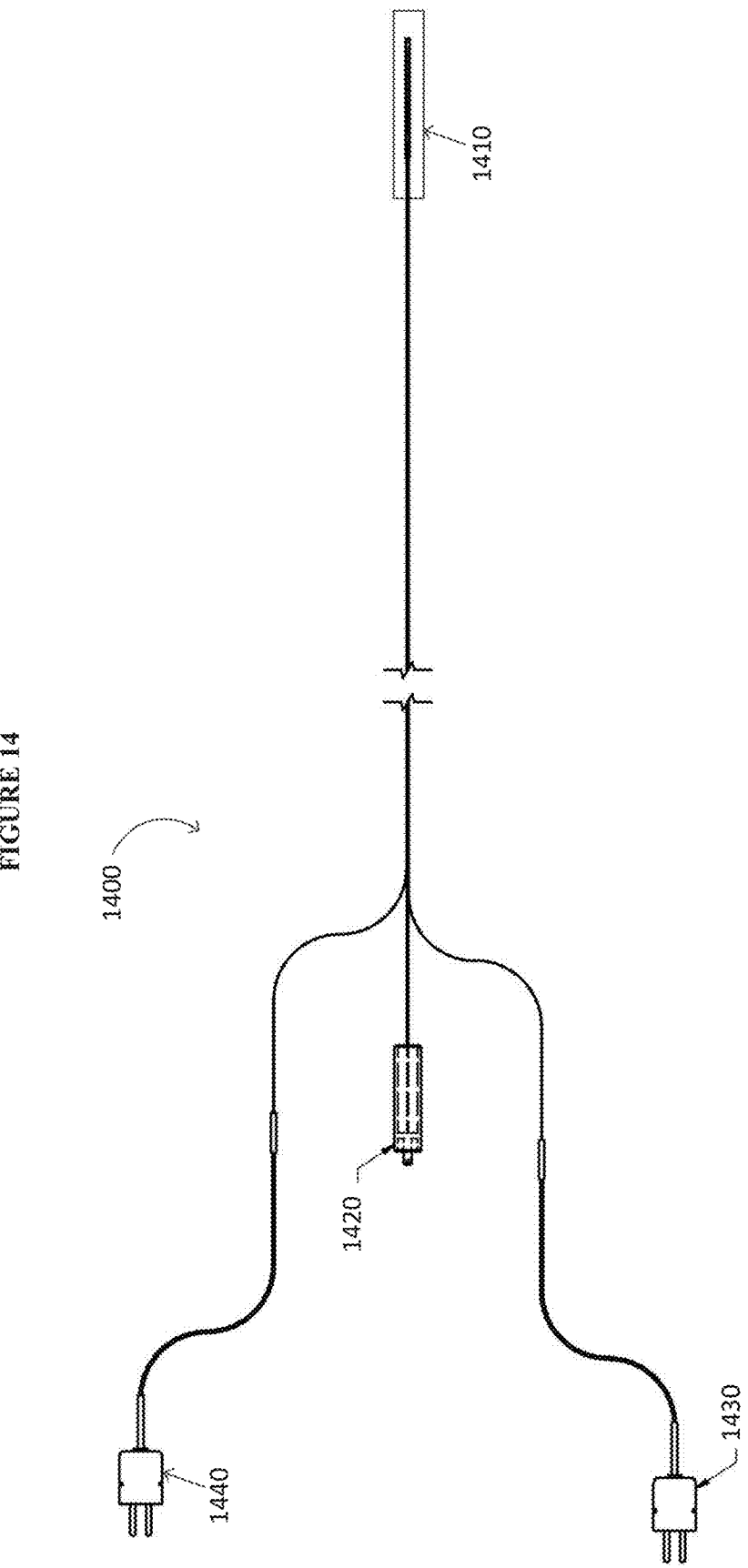
FIG. 14 illustrates an example system or assembly for interstitial laser therapy.
Figure 15:
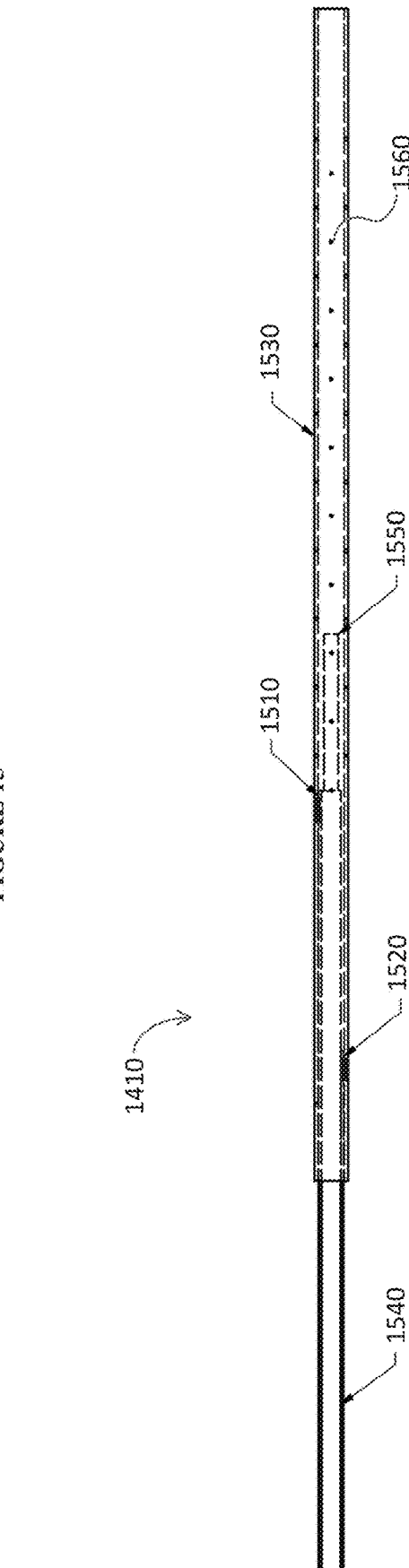
FIG. 15 illustrates an example device for use in an example system or assembly for interstitial laser therapy.

FIG. 14 illustrates part of an example system or assembly 1400 for interstitial laser therapy. System or assembly 1400 includes an optical diffuser (and other components) assembly section 1410, a connector 1420 for a laser fibre, a connector 1430 for a first thermocouple (i.e. a first temperature sensor), and a connector 1440 for a second thermocouple (i.e. a second temperature sensor). FIG. 15 illustrates further details of the optical diffuser (and other components) assembly section 1410. Optical diffuser 1530 attaches to laser fibre (with jacket) 1540. A first thermocouple 1510 (i.e. first temperature sensor) and optionally a second thermocouple 1520 (i.e. second temperature sensor) can be provided. Also illustrated is laser fibre 1550, preferably with a clear silica tip. Optical diffuser 1530 can be glued or otherwise attached (e.g. frictionally fitted) onto laser fibre 1540. One or more apertures, holes, openings, and/or vents 1560 can be provided as part of optical diffuser 1530.

Figure 16:
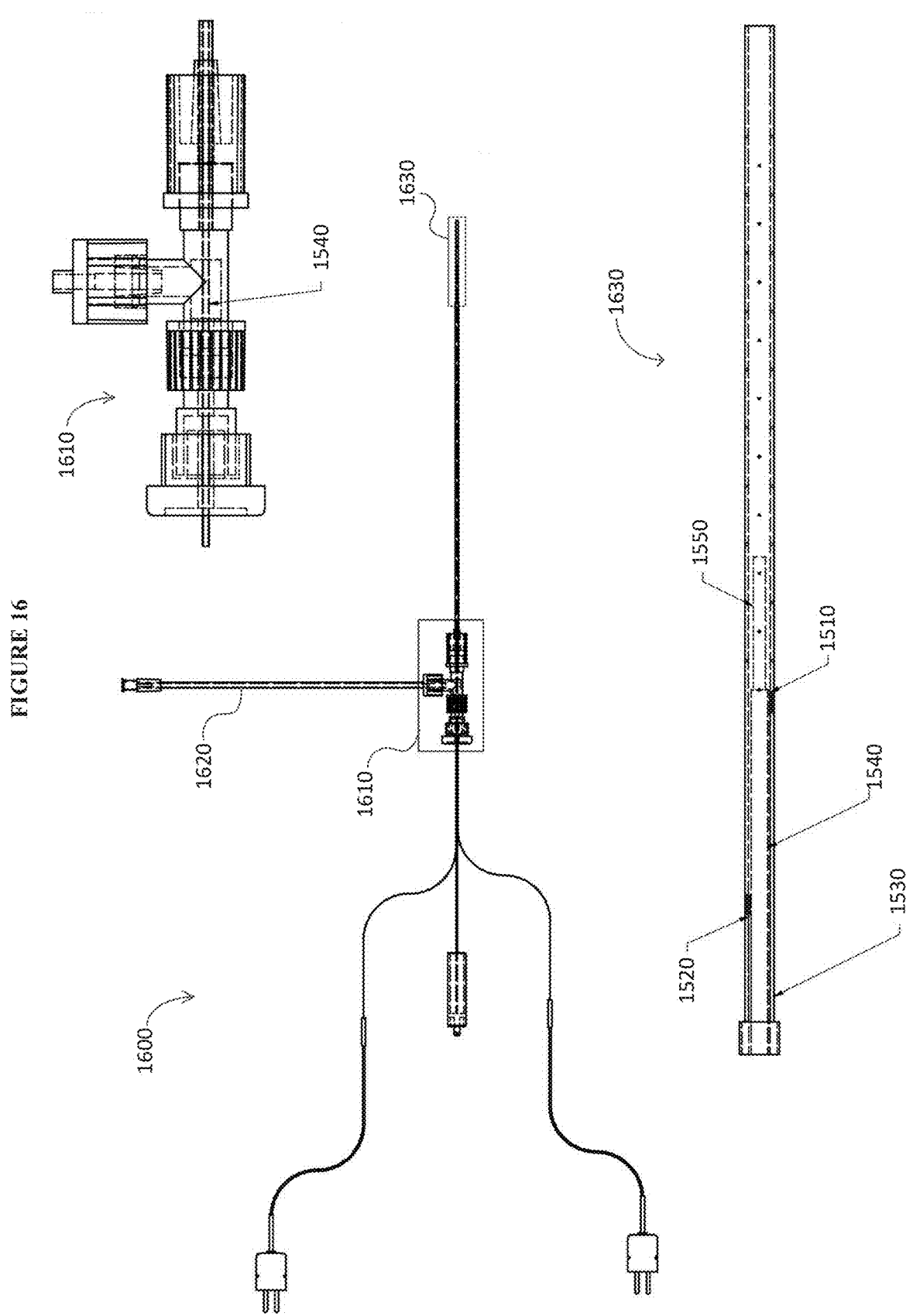
FIG. 16 illustrates another example system or assembly for interstitial laser therapy.
Figure 17:
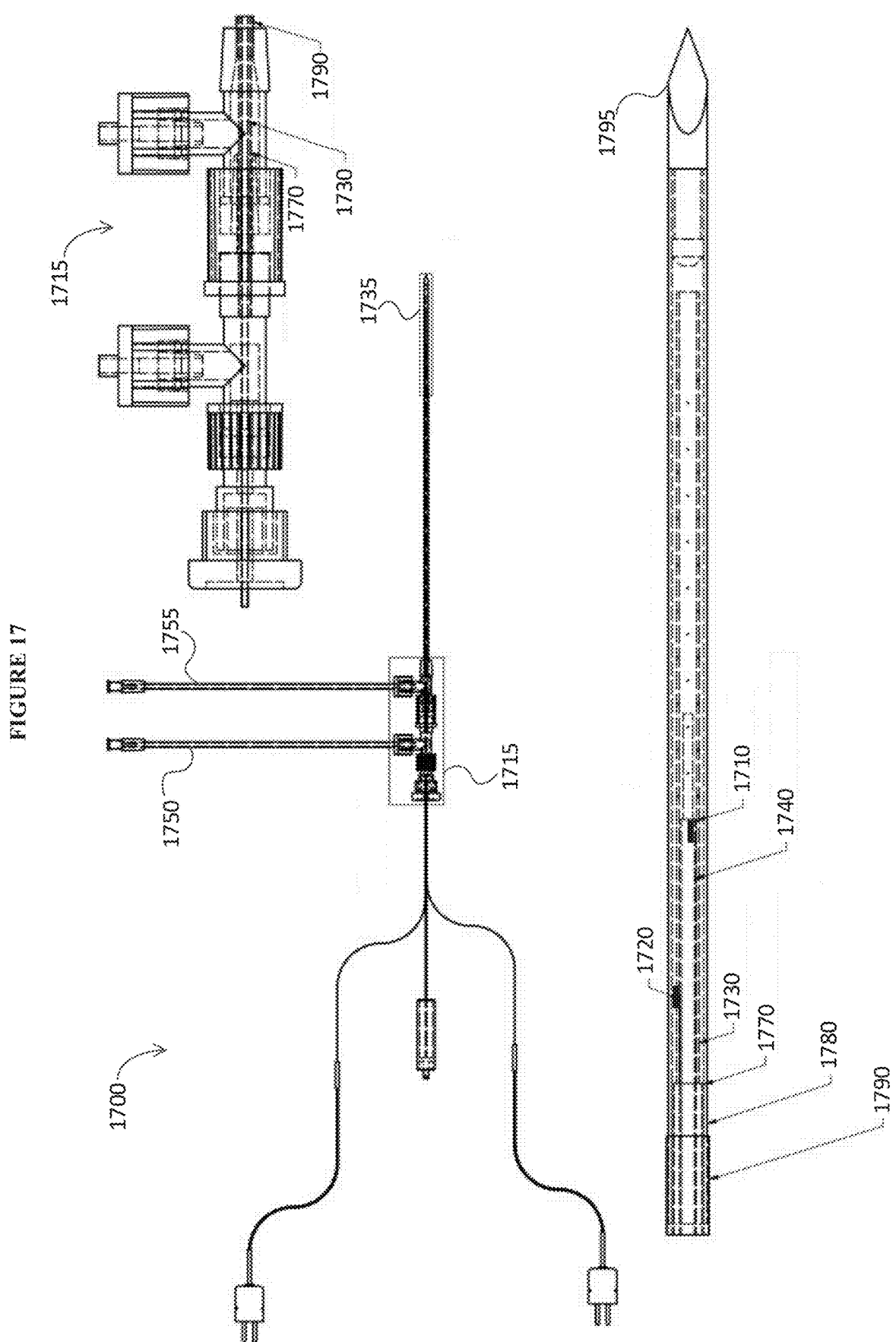
FIG. 17 illustrates another example system or assembly for interstitial laser therapy.

FIG. 16 illustrates another example system or assembly 1600 for interstitial laser therapy. Connectors 1610, which can be a variety of types or configurations, are used for connecting tubes or pipes transporting cooling fluid. The cooling fluid can be introduced by input pipe or tubing 1620, through connectors 1610, to be directed to operational zone 1630 (i.e. about the optical diffuser section). Operational zone 1630 includes optical diffuser 1530, first thermocouple 1510 (i.e. first temperature sensor), second thermocouple 1520 (i.e. second temperature sensor), laser fibre (with jacket) 1540 as at least part components. Laser fibre 1540, and thermocouples (i.e. temperature sensors), can be inserted through connectors 1610, or at least some of connectors 1610, into jacket tubing. An example of a cooling fluid is water, which can be introduced into the system at a desired water temperature, which could be room temperature, or the introduced water could first be cooled to be less than room temperature. Other types of cooling fluid can be used. FIG. 17 illustrates another example system or assembly 1700 for interstitial laser therapy. Connectors 1715 include an arrangement of connectors for introducing or transporting cooling fluid to operational zone 1735 via first inlet/outlet tube or pipe 1750 and second inlet/outlet tube or pipe 1755. In operational zone 1735 (i.e. about the optical diffuser section) there is provided optical diffuser 1730, first thermocouple 1710 (i.e. first temperature sensor), second thermocouple 1720 (i.e. second temperature sensor), laser fibre (with jacket) 1740 and jacket tubing 1770. Also provided is an introducer first section 1780, in this example being clear or transparent tubing, and an introducer second section 1790, in this example being metallic tubing. Trocar 1795, or other form of sharp instrument, is provided at an end.

In other examples, the introducer, i.e. the channel or the cannula, can be provided with a clear end portion and/or a closed trocar tip. An introducer, or channel or cannula, with a clear end portion allows for laser energy and/or heat to be transmitted out from the introducer, or cannula, into the tissue. The trocar has a sharp end which can be used to penetrate tissues like a normal cannula. In an example, a cannula can be used having a trocar tip that is provided as a transparent tip or a semi-opaque tip. An end portion of the introducer, or channel or cannula, can be made of a transparent material, an optically clear material or an optically semi-opaque material. Optionally, the complete length of the introducer, or channel or cannula, can be made of the same material (i.e. the transparent material, the optically clear material or the optically semi-opaque material). These examples allow laser energy and/or heat to penetrate through the walls of the introducer, or channel or cannula, into surrounding tissues. As illustrated, the introducer, or cannula, can be provided with fluid or irrigation inlets/outlets if used with a cooling or irrigation fluid. In other examples the introducer, or channel or cannula, could be opaque, for example made of metal or ceramic. The introducer (i.e. the channel or the cannula), or the end portion thereof, and the trocar (i.e. a puncturing spike section or region, or a metallic spike) can be transparent, optically clear or optically semi-opaque, and together can function as a combined, or integrated, trocar-diffuser device or unit. That is, the trocar can function similarly to, and/or complimentary with, the optical diffuser. The trocar (i.e. a puncturing spike section or region, or a metallic spike) can also act as an optical diffuser (or part of an optical diffuser), at the same time as acting as a trocar. That is, the trocar has a dual function. In such an example, the trocar is optically coupled to, or is optically associated with, an optical output end of an optical waveguide, similarly as described previously herein for the optical diffuser. The trocar can also be provided with an inlet for irrigation fluid.

Figure 18:
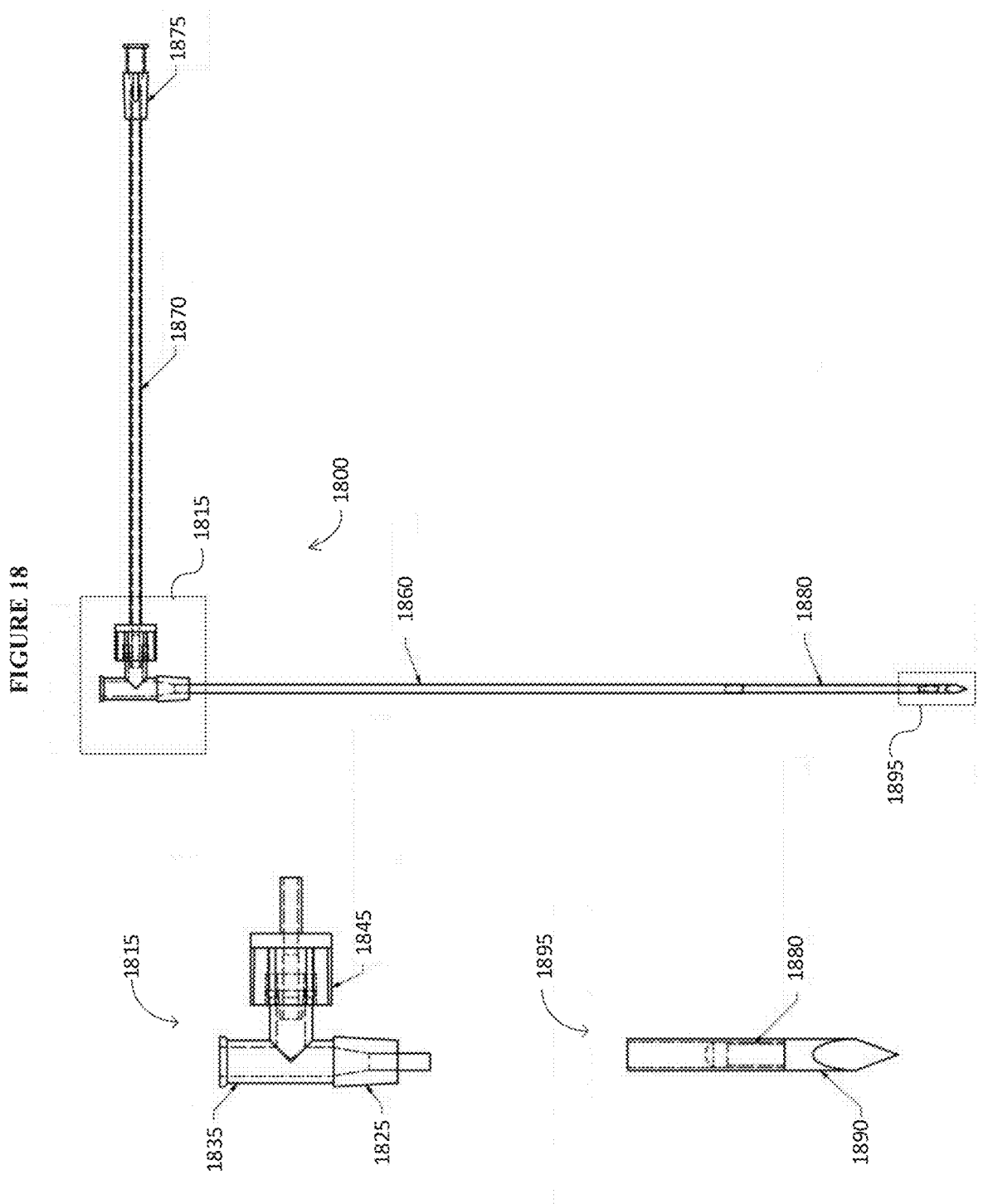
FIG. 18 illustrates an example introducer for use in an example system or assembly for interstitial laser therapy.

FIG. 18 illustrates another example system or assembly 1800 for interstitial laser therapy. Connectors 1815, for example including a T-connector, can include a male luer slip port 1825, and a female luer lock 1835 which is connected to a male luer cap 1845 and which includes a fluid extension line or pipe. System or assembly 1800 includes trocar section 1895, or puncturing spike section, which includes a metallic spike 1890, or other cutting edge, which can be glued, or otherwise attached to clear or transparent tubing 1880. Clear or transparent tubing 1880 provides a suitable clear or transparent window or region for correct laser operation. Tubing 1860, which can be metallic for example, connects connectors 1815 to clear or transparent tubing 1880. In another example, there may not be any metallic tubing 1860 and instead clear or transparent tubing 1880 may extend between connectors 1815 and trocar section 1895, or puncturing spike section. Fluid transmission extension line or pipe 1870 connects to female luer lock 1875 which provides an exit port for cooling fluid. System or assembly 1800 includes an "introducer", i.e. a cannula, which includes one or more hollow tubes or pipes, having a trocar tip, i.e. spike. The hollow tube or pipe is closed off at a distal end. A stiffening rod, i.e. a "stiffener", can be placed through the middle of the introducer, or cannula, for example during the initial stages of establishing a portal through tissue. A jacket tube can be provided which is a stiffening tube or pipe and which houses the assembly of the laser fibre, one or more thermocouples (i.e. one or more temperature sensors) and the optical diffuser, so as to allow these components to be inserted into the introducer.

Figure 19:
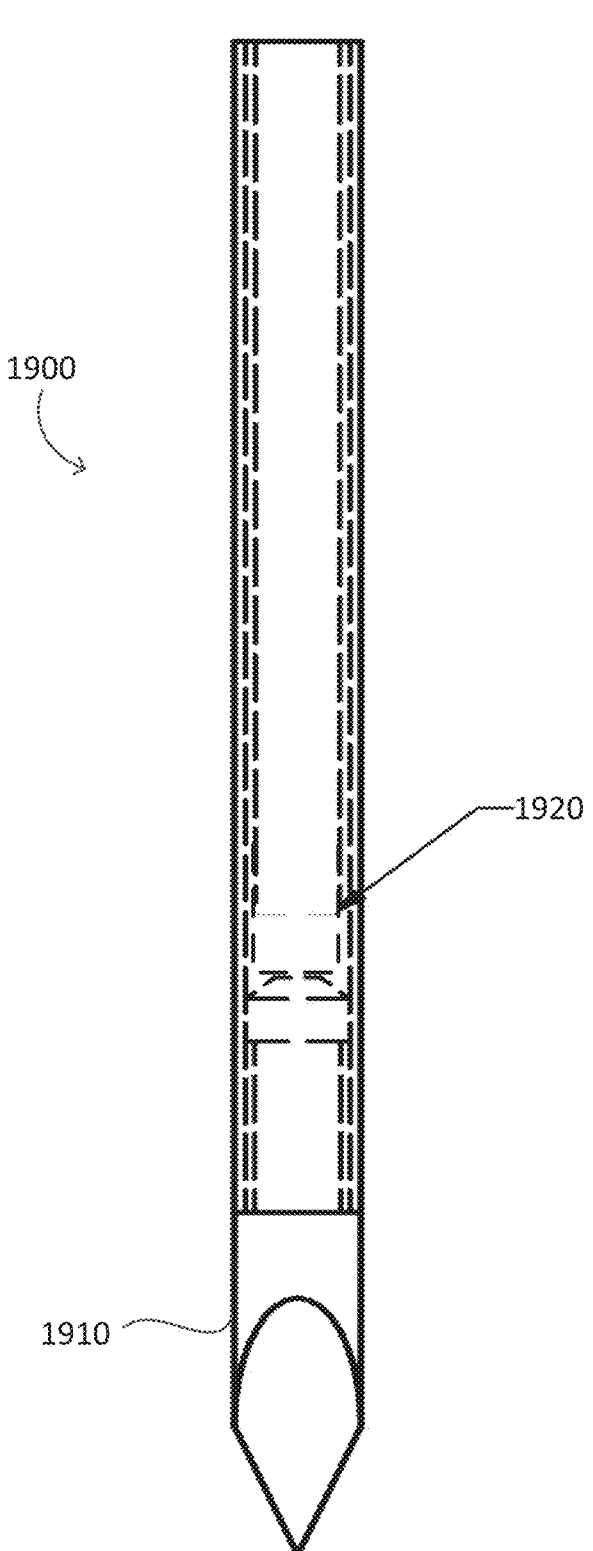
FIG. 19 illustrates an example trocar section including a stiffener and a spike for use in an example system or assembly for interstitial laser therapy.
Figure 20:
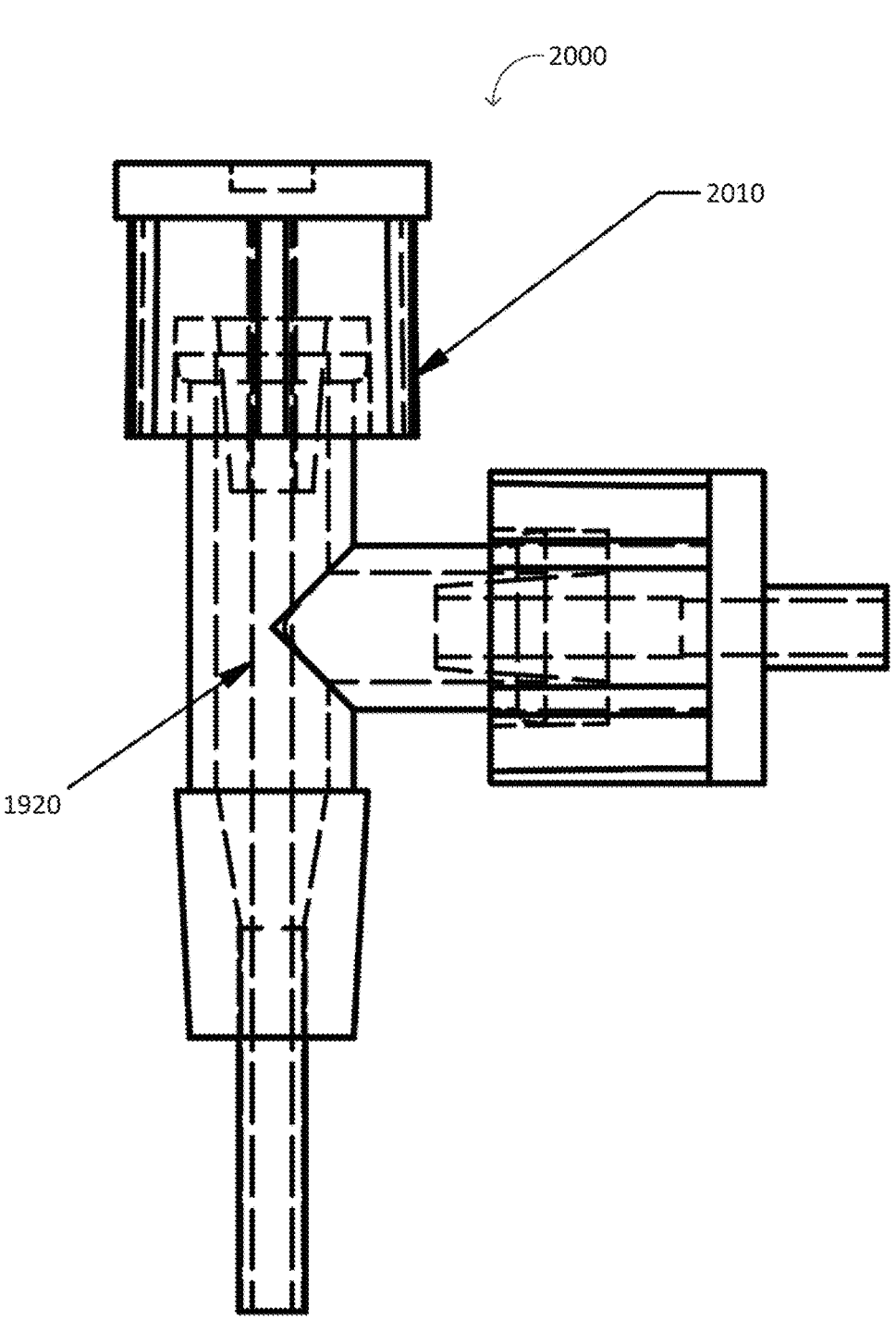
FIG. 20 illustrates example connectors and a stiffener position.

FIG. 19 shows a distal end part for a trocar section 1900, i.e. a puncturing spike section or region, having a metallic spike 1910 or other form of cutting and/or piercing edge. Also illustrated is stiffener 1920. In different examples an end of stiffener 1920 can be touching or abutting an internal end of metallic spike 1910 (as illustrated) or an end of stiffener 1920 can be spaced apart from an internal end of metallic spike 1910. FIG. 20 illustrates example connectors 2000 and stiffener 1920. Stiffener 1920, for example a stiffening rod, can be inserted into the introducer, i.e. cannula. Male luer cap 2010 from stiffener 1920 locks onto a female luer lock. In one example the introducer can include an opaque tube (e.g. a metallic tube) longitudinally extending part way along its length and a clear tube, or a transparent tube, or a clear window, provided or longitudinally extending near a distal end of the introducer. In another example, the introducer could be a length of tube that is entirely transparent, clear or semi-opaque material.

System with Cooling Fluid for Interstitial Laser Therapy

Figure 21:
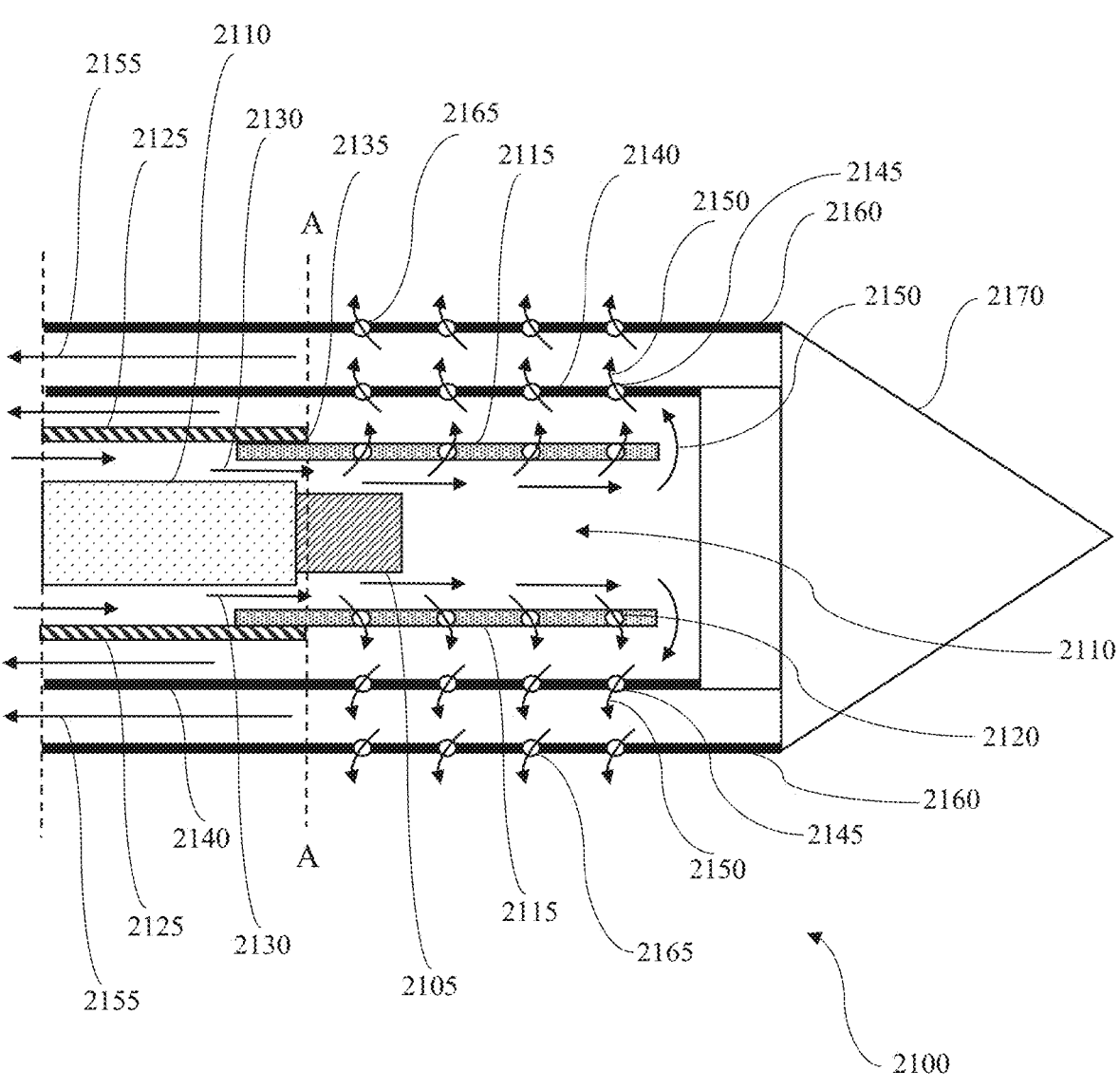
FIG. 21 illustrates a cross-sectional view of an end section (near an operational zone) of an example system provided with cooling fluid for interstitial laser therapy, indicative fluid flows are illustrated by arrows. The device for interstitial laser therapy, as discussed herein, can be part of the system with cooling fluid for interstitial laser therapy.

FIG. 21 illustrates a cross-sectional view of an end section (near an operational zone where tissue is being removed by laser therapy) of an example system with cooling fluid 2100 for interstitial laser therapy. In one example, cooling fluid is water. Indicative cooling fluid flows are illustrated by the arrows. A device 2110 for interstitial laser therapy, can be any of the example devices for interstitial laser therapy as described and illustrated herein, and is part of the system with cooling fluid 2100 for interstitial laser therapy. However, it should be appreciated that other example types of devices for interstitial laser therapy, not described or illustrated herein, could be used as part of the system with cooling fluid 2100 for interstitial laser therapy. For the device 2110 for interstitial laser therapy illustrated, temperature sensors are not shown for clarity, however, any of the previously described and illustrated example devices for interstitial laser therapy can be used. Device 2110 for interstitial laser therapy includes laser fibre 2105 (for example optical output end 112, 212, 312 of optical waveguide 110, 210, 310, or laser fibre 1550), and laser fibre jacket 2110 (for example outer layer 144, 244, 344 of optical waveguide 110, 210, 310, or laser fibre with jacket 1540, 1740). Device 2110 for interstitial laser therapy also includes optical diffuser 2115 (for example optical diffuser 130, 230, 330, 630, 730, 830, 930, 1030, 1130, 1230, 1330, 1530, 1730) positioned over or around, i.e. surrounds, the optical output end of the optical waveguide. Optical diffuser 2115 is preferably provided with one or more optical diffuser apertures 2120 as previously described and illustrated herein (for example one or more apertures, holes, slits, openings and/or vents 640, 740, 840, 940, 1040, 1240, 1340, 1560).

The irrigation tube 2125 is positioned over or around at least part of the optical waveguide, and irrigation tube 2125 surrounds at least part of laser fibre jacket 2110 and directs input cooling fluid, that is input into irrigation tube 2125, as fluid flows 2130 to flow out of distal end 2135, or tip, of irrigation tube 2125. In the example illustrated in FIG. 21, irrigation tube 2125 is positioned over or around, i.e. surrounds, and can be sealed to or abut, an end part of optical diffuser 2115. This arrangement means cooling fluid is directed to flow towards and within, about, or around optical diffuser 2115, and in the example illustrated cooling fluid is directed to flow inside of and cool optical diffuser 2115. The irrigation tube 2125 can be made of any suitable material or composite of materials. The irrigation tube 2125 can be rigid, for example to assist in stiffening or supporting the length of the device for interstitial laser therapy 2110, or the irrigation tube 2125 can be semi-rigid or flexible. In one preferred example the irrigation tube 2125 is a metal tube. The irrigation tube 2125 (also termed an irrigation tube) is positioned over or around part of the optical diffuser 2115, which results in cooling fluid (i.e. irrigation fluid) to flow inside the optical diffuser 2115. Cooling fluid is able to flow out of one or more optical diffuser apertures 2120, which are optional and may or may not be provided as part of optical diffuser 2115. Preferably, one or more optical diffuser apertures 2120 are provided as part of optical diffuser 2115. Cooling fluid can also, in the example embodiment illustrated, flow out of an end of optical diffuser 2115 as illustrated by fluid flows 2150.

An imaginary line A-A is defined at the distal end 2135, or tip, of irrigation tube 2125, being perpendicular to the lengthwise axis of irrigation tube 2125 (i.e. being perpendicular to central longitudinal axis 120). Cooling fluid is introduced into the other end of irrigation tube (not illustrated), for example as discussed for the systems shown in FIGS. 16, 17 and 18. An example of a cooling fluid is water, which can be introduced into the system at a desired water temperature, which could be room temperature, or the introduced water could first be cooled to be less than room temperature. Other types of cooling fluid can be used. The fluid guide tube 2140 is provided to be positioned over or around, i.e. surround, at least part of irrigation tube 2125 and at least part of optical diffuser 2115. Fluid guide tube 2140 can be positioned over or around the whole of irrigation tube 2125 and/or the whole of optical diffuser 2115. Fluid guide tube 2140 is provided with one or more fluid guide tube apertures 2145, which may be one or more holes, slits, openings and/or vents (similarly to one or more apertures, holes, slits, openings and/or vents 640, 740, 840, 940, 1040, 1240, 1340, 1560). Cooling fluid can flow through one or more fluid guide tube apertures 2145, preferably in one example to exit out of fluid guide tube 2140, as indicated by fluid flows 2150. Alternatively, in another example, fluid flows can be different or reversed from that illustrated, and the cooling fluid can flow into the fluid guide tube 2140 via at least the one or more fluid guide tube apertures 2145. In various examples, cooling fluid can egress or ingress through the one or more fluid guide tube apertures 2145.

Cooling fluid can be removed from the operational zone, and away from optical diffuser 2115 after cooling optical diffuser 2115 and nearby areas, along return fluid flows 2155. Outer tube 2160 can be provided with one or more apertures 2165, thus allowing cooling fluid to flow out of one or more apertures 2165. In some examples, outer tube 2160 does not have one or more apertures and may constrain and direct the flow of cooling fluid to be along return fluid flows 2155. Away from the operational zone, a fluid flow channel for return fluid flows 2155 is provided by the external surface of fluid guide tube 2140 and the internal surface of outer tube 2160. Non-limiting examples of outer tube 2160 could be made of a polycarbonate material or could be made of PTFE (polytetrafluoroethylene). It should be realised that the number of apertures, holes, slits, openings and/or vents shown in example tubes (i.e. fluid guide tube and/or outer tube) is for illustration only and any number can be utilised, for example one, two, three, four, five, six, seven, eight, nine, ten, etc. apertures, holes, slits, openings and/or vents can be utilised, or any combination thereof. The one or more apertures in optical diffuser 2115, fluid guide tube 2140 and outer tube 2160, can be arranged sets of apertures spaced about the circumference of each of the optical diffuser 2115, fluid guide tube 2140 and outer tube 2160. For example, there may be two, three, four, five, six, etc., apertures in a set of apertures that are equidistantly placed about the circumference at the same longitudinal axial position. Furthermore, two, three, four, five, six, etc., sets of apertures could be used that are positioned at different locations along the longitudinal axis of each of the optical diffuser 2115, fluid guide tube 2140 and outer tube 2160. In a specific example, there are four apertures in a set of apertures, each aperture positioned radially at 90 degrees to each neighbouring aperture, and there are two sets of apertures positioned along the axial length. Trocar 2170 can be provided as part of the system with cooling fluid 2100 for interstitial laser therapy, as previously described herein as for example trocar 1795, 1890, 1910. In an example trocar 2170 is metallic, for example titanium. Outer tube 2160 could be, for example, previously described herein introducer 1780 (i.e. a cannula).

The longitudinal extent to which irrigation tube 2125 extends along the length of laser fibre jacket 2110 and/or optical diffuser 2115 (in examples where there is lengthwise overlap between irrigation tube 2125 and optical diffuser 2115) can be varied. That is, line A-A can be varied along the length of the device 2110 for interstitial laser therapy. For example:

there may be no lengthwise overlap between irrigation tube 2125 and optical diffuser 2115;

there may be a partial lengthwise overlap between irrigation tube 2125 and optical diffuser 2115, such that distal end 2135 of irrigation tube 2125 is within the lengthwise extent of optical diffuser 2115; or there may be complete lengthwise overlap between irrigation tube 2125 and optical diffuser 2115, such that irrigation tube 2125 completely covers optical diffuser

2115, for example in an embodiment where irrigation tube 2125 is made of a material that is transparent to the laser light emitted from laser fibre 2105.

Other example systems described herein, for example as illustrated in FIGS. 15-20, describe components that can be used with system with cooling fluid 2100 for interstitial laser therapy. However, system with cooling fluid 2100 for interstitial laser therapy additionally utilises at least one fluid guide tube 2140 to provide further advantages for cooling. Additionally, in the system with cooling fluid 2100 for interstitial laser therapy, the system allows positioning of irrigation tube 2125 so that distal end 2135 of irrigation tube 2125 can be used to define, or substantially define, a longitudinal extent of a laser ablation zone. For example, distal end 2135 of irrigation tube 2125 is positioned farther away from trocar 2170, different to the system discussed for FIG. 19, so that a laser ablation zone is controlled in longitudinal extent and as irrigation tube 2135 and fluid guide tube 2140 direct and/or remove cooling fluid flows inside of and/or about optical diffuser 2115. It should be noted that vaporised cooling fluid, for example steam, may also pass through, either exiting or entering, one or more apertures, for example in situations where laser heating causes vaporization of cooling fluid. In another example, flow of cooling fluid, for example the rate of flow or the pressure of the cooling fluid, can be changed by control of a driving pump that is pumping the cooling fluid, or by control of a flow regulator in the fluid line of the cooling fluid. This produces changes in, i.e. control of, the ablation zone and resulting control over the ablation of tissue.

Positioning of irrigation tube 2125 relative to other components in the system with cooling fluid 2100, for example adjusting the position relative to a distal end of the system with cooling fluid 2100 or relative to trocar 2170, can be used to change the length, size or extent of the ablation zone. Preferably, irrigation tube 2125 and the device for interstitial laser therapy 2110 (i.e. including the laser fibre 2105 and optical diffuser 2115) both move and adjust position together. That is, preferably irrigation tube 2125 does not move independently of the device for interstitial laser therapy 2110 (i.e. including the laser fibre 2105 and optical diffuser 2115). By adjusting the position of irrigation tube 2125 and the device for interstitial laser therapy 2110 (i.e. including the laser fibre 2105 and optical diffuser 2115) along a longitudinal axis, relative to a distal end of the system with cooling fluid 2100, or relative to the position of trocar 2170, the ablation zone can be changed and made longer or shorter in length along the longitudinal axis. As irrigation tube 2125, jointly with the device for interstitial laser therapy 2110 (i.e. including the laser fibre 2105 and optical diffuser 2115), is pushed forward or pulled away from the distal end of the system with cooling fluid 2100, or the position of trocar 2170, or the catheter end, the ablation zone will correspondingly shorten or lengthen, respectively, along the longitudinal axis. A mechanism to adjust the position of irrigation tube 2125 and the device for interstitial laser therapy 2110 (i.e. including the laser fibre 2105 and optical diffuser 2115), along a longitudinal axis relative to, for example, the distal end of the system with cooling fluid 2100 or relative to the position of trocar 2170, can be placed on a handle proximal to a user's hand to make such an adjustment before or during an ablation procedure.

In further examples, a system with cooling fluid can be provided where the device for interstitial therapy 2110 is steerable. For example, irrigation tube 2125, fluid guide tube 2140 and outer tube 2160, if they are utilised, can be flexible and one or more of irrigation tube 2125, fluid guide tube 2140 and outer tube 2160, if they are utilised, can be steerable so that the direction that the end of the device for interstitial therapy 2110 points can be controlled by an operator. By being steerable this allows that if laser energy is directed out of the distal end of the device for interstitial therapy 2110, then the operator can direct the laser energy in a desired direction. Preferably, though not necessarily, the optical diffuser is composed of a heat resistant material able to withstand temperatures up to at least about 100° C., or any maximum temperature that may be required for interstitial laser therapy. Optionally, at least part of, or all of, the optical diffuser is made of polytetrafluoroethylene (PTFE). In other examples, other light transmissive materials may provide at least part of, or all of, the optical diffuser, such polycarbonate, polyurethane, polyethylene, polypropylene, silicon, nylon, PVC, PET, ABS, PES, PEEK, FEP, or other flexible or rigid materials as appropriate.

Figure 22:
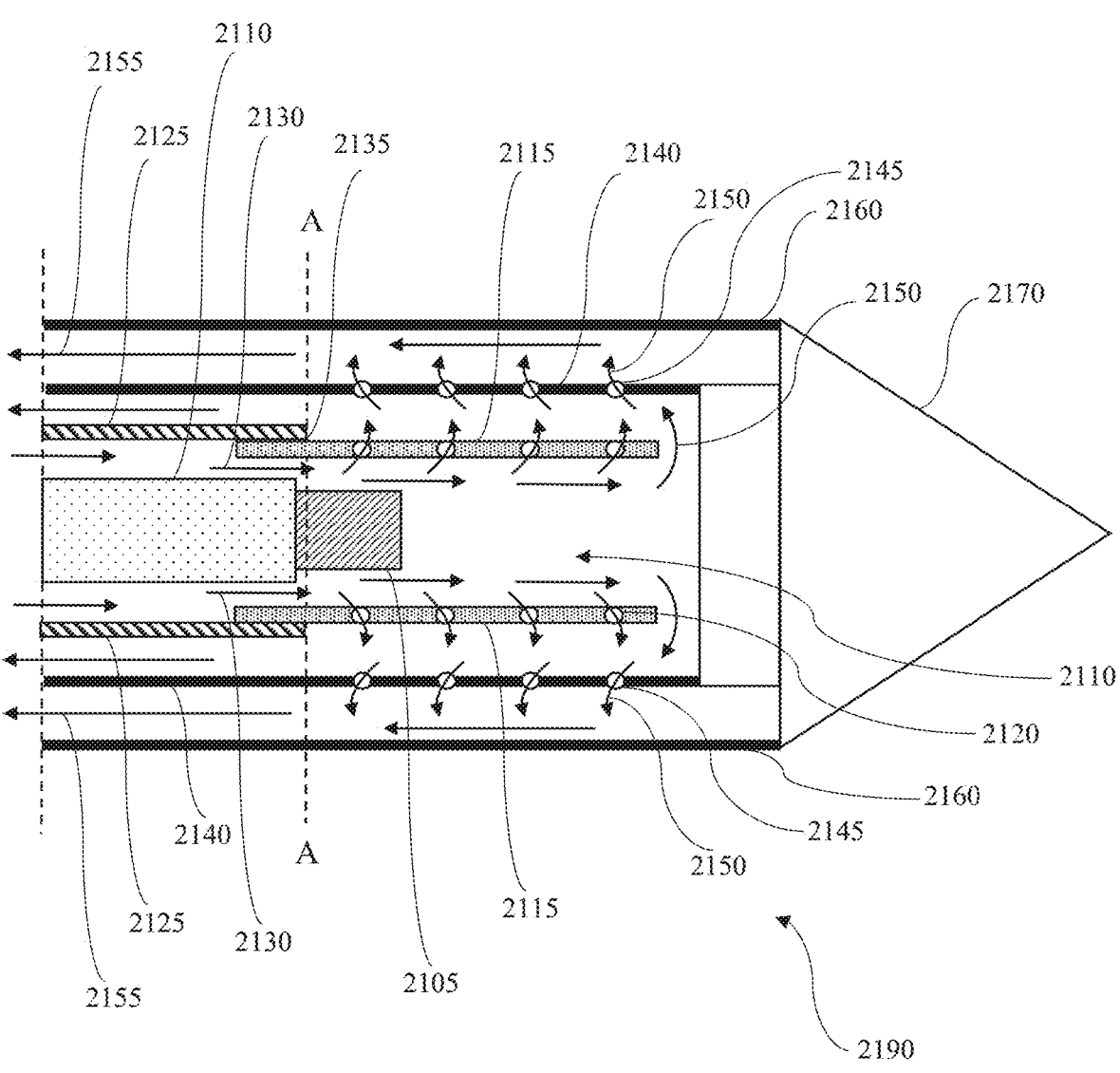
FIG. 22 illustrates a cross-sectional view of an end section (near an operational zone) of another example system provided with cooling fluid for interstitial laser therapy.
Figure 23:
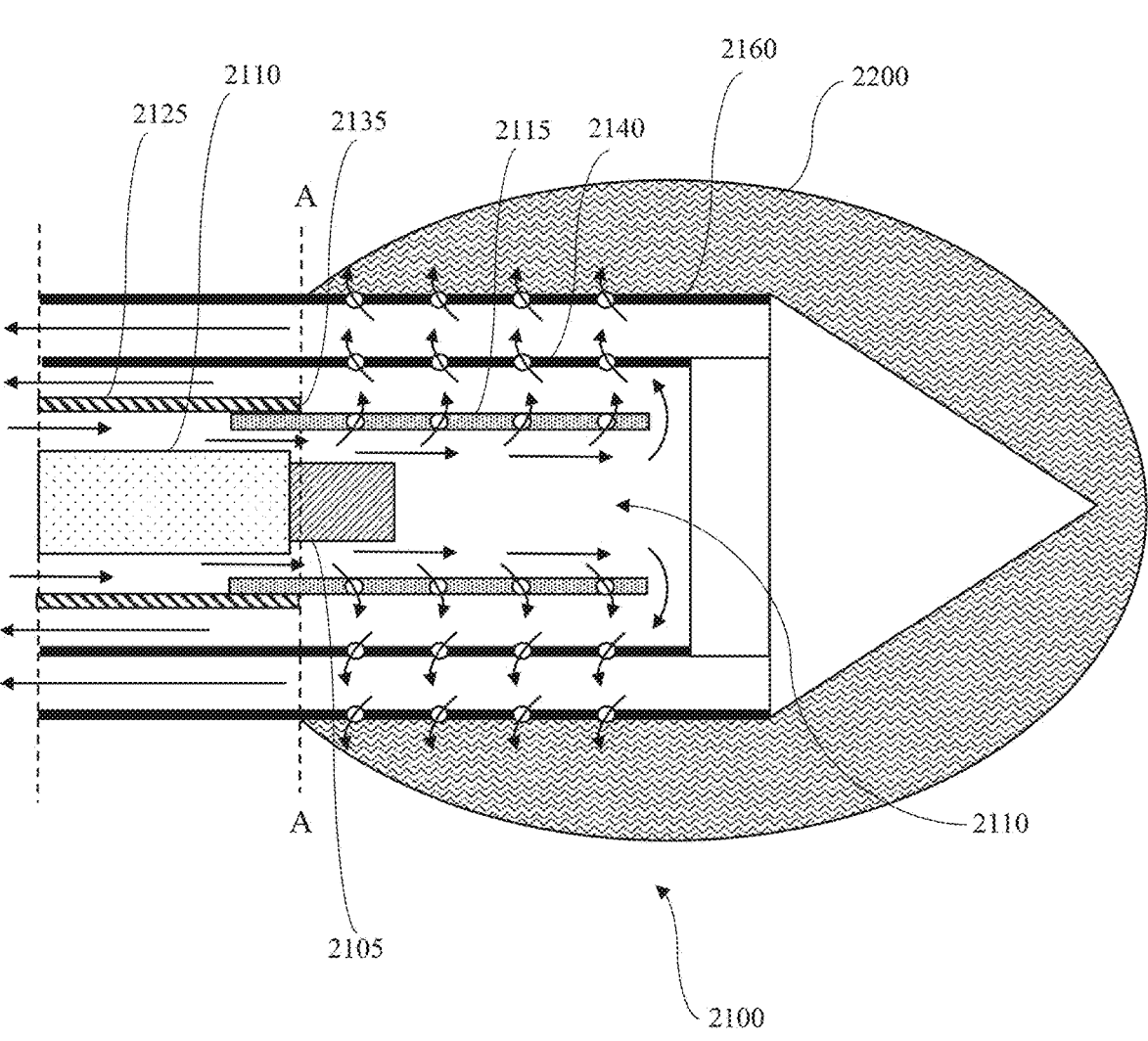
FIG. 23 illustrates the example system with cooling fluid for interstitial laser therapy of FIG. 21, when in use to produce a laser ablation zone, and shows the laser ablation zone being limited in extent to be forward of a line A-A defined by the distal end of an irrigation tube, where the cooling fluid flows out from the distal end of the irrigation tube.

FIG. 22 illustrates a cross-sectional view of an end section (near an operational zone where tissue is being removed by laser therapy) of another example system with cooling fluid 2190 for interstitial laser therapy. In this example, outer tube 2160 is solid and does not have one or more apertures and so constrains and directs the flow of cooling fluid to be along return fluid flows 2155. FIG. 23 illustrates the system with cooling fluid 2100 of FIG. 21 in use to produce a laser ablation zone 2200 and shows laser ablation zone 2200 being limited in longitudinal extent to be substantially forward of line A-A defined by distal end 2135 of irrigation tube 2125. That is, in use the flow of cooling fluid out of irrigation tube 2125 acts to reduce temperatures so that the laser ablation zone does not extend beyond, or substantially beyond, a cross-sectional area intersecting with distal end 2135 of irrigation tube 2125, where the cross-sectional area is perpendicular to the longitudinal axis of irrigation tube 2125. A radial axis of the cross-sectional area is defined by line A-A. The system with cooling fluid 2100 for interstitial laser therapy (i.e. a thermotherapy laser ablation device) limits the laser ablation zone 2200 to be generally forward of line A-A at or near the end of the irrigation tube 2125, which allows for better control of the laser ablation zone 2200 and much more predictive and accurate laser ablation therapy. The laser ablation zone 2200 is considered to be the zone or region where laser power is sufficient to ablate tissue or cells.

Irrigation tube 2125 thus may have a dual purpose in system with cooling fluid 2100 for interstitial laser therapy. Firstly, irrigation tube 2125 supports device 2110 for interstitial laser therapy so as to assist in safety and ease of insertion of laser fibre 2105 and optical diffuser 2115 into fluid guide tube 2140 (and outer tube 2160, for example the introducer provided with a trocar 2170). Secondly, irrigation tube 2125 provides a cooling fluid flow channel for inflow of cooling fluid to be directed to optical diffuser 2115 and/or the region surrounding optical diffuser 2115. The flow of cooling fluid, which exits irrigation tube 2125 at distal end 2135 of irrigation tube 2125 defined by line A-A, ameliorates, or prevents, laser ablation zone 2200 from extending rearwards along the longitudinal length of outer tube 2160 away from trocar 2170 substantially beyond line A-A. The limitation of the laser ablation zone 2200 to a region forward of the distal end 2135, or tip, of irrigation tube 2125 provides for greatly improved accuracy of ablation of tissue in surgical use. The extent of and/or control of the ablation zone, leading to control of ablation, including for example the rate of ablation, can be controlled by different means. In a fixed laser power system, control of cooling fluid flow (i.e. coolant flow), in combination with monitoring of temperature allows an operator to control the extent and/or rate of ablation. In a fixed cooling fluid flow (i.e. coolant flow) system, control of laser power, in combination with monitoring of temperature also allows an operator to control the extent and/or rate of ablation. Measurement of the difference in temperature between an inlet region and an outlet region of cooling fluid is an indicator of the energy withdrawn from the available laser energy, the balance of the laser energy is available to induce ablation.

Figure 24:
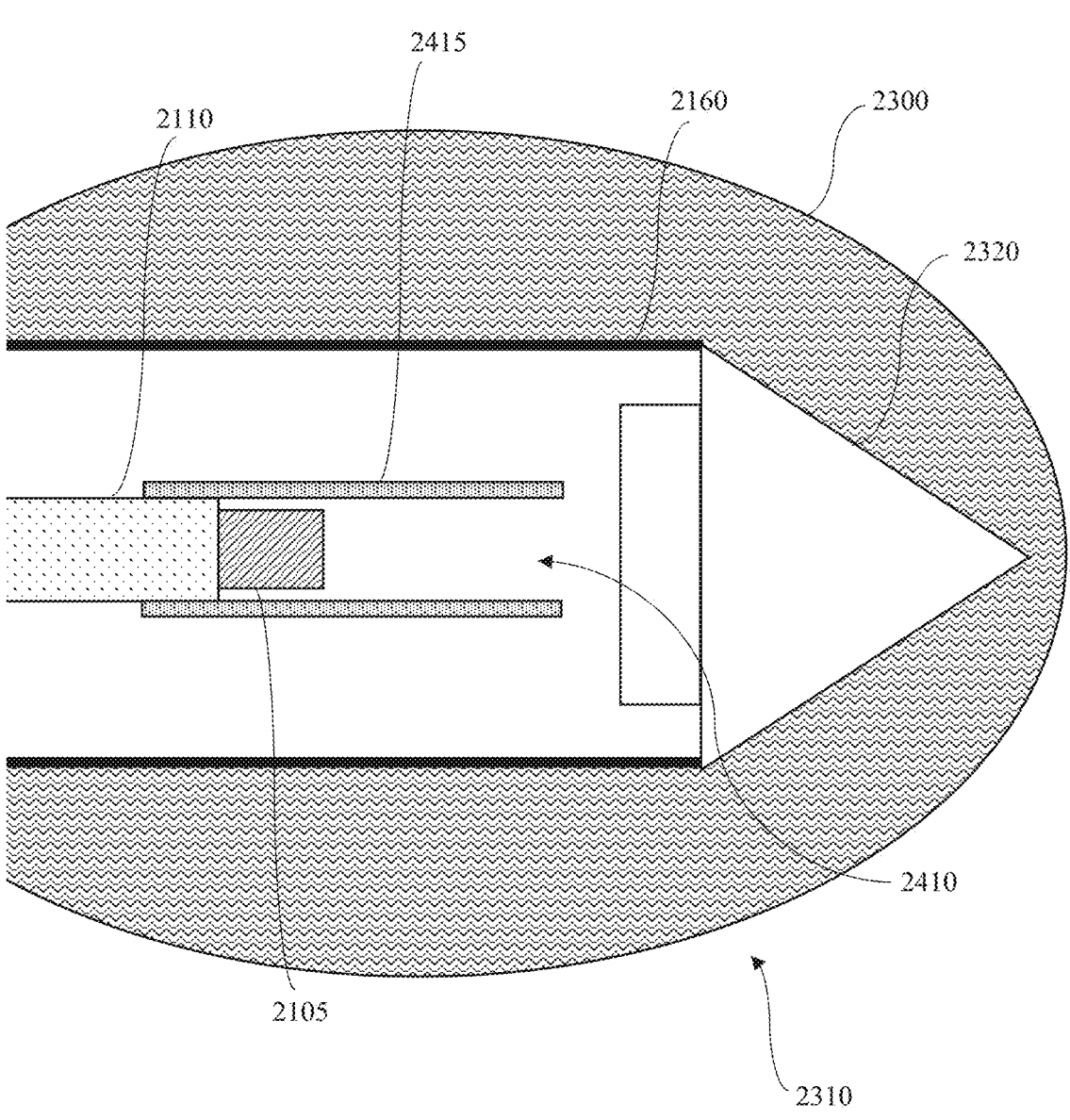
FIG. 24 illustrates another example system for interstitial laser therapy, which uses an example device for interstitial laser therapy, and where the system is not provided with cooling fluid or a cooling fluid system, and in this case shows the laser ablation zone being more unconstrained and extending rearward farther along the length of the device.
Figure 25:
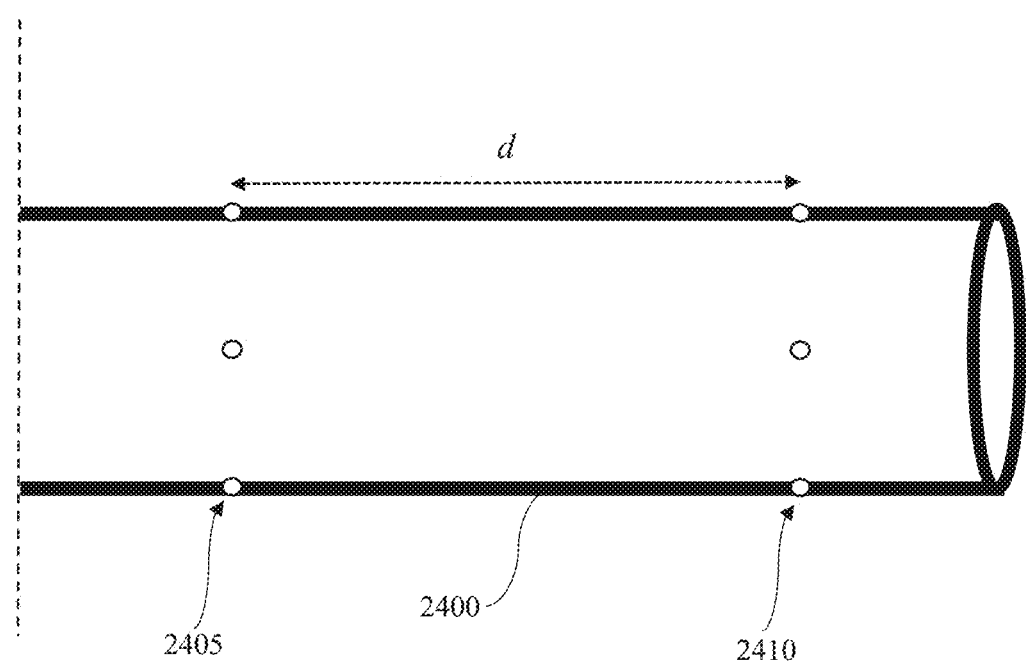
FIG. 25 illustrates an example fluid guide tube, provided as part of the system with cooling fluid for interstitial laser therapy, and with the fluid guide tube provided with one or more apertures for facilitating egress or ingress of cooling fluid.

In contrast, FIG. 24 illustrates another example system 2310 for interstitial laser therapy, including device 2410 for interstitial laser therapy having optical diffuser 2415 for example without one or more apertures, but where the system 2310 is not provided with cooling fluid or a cooling fluid system. In this case for system 2310, the laser ablation zone 2300 is more unconstrained and extends farther backwards along the longitudinal length of the device 2410. For such a system 2310, without irrigation tube 2125 introducing cooling fluid, the extent of the laser ablation zone 2300 can be unpredictable rearwards of the trocar 2320. FIG. 25 illustrates an example fluid guide tube 2400, provided as part of the system with cooling fluid 2100, 2190 for interstitial laser therapy, and with the fluid guide tube 2400 provided with one or more apertures as a set of apertures 2405, 2410 for facilitating egress of cooling fluid from inside fluid guide tube 2400. In one example, fluid guide tube 2400 is made of PTFE (polytetrafluoroethylene) or other type of fluoropolymer. In the specific non-limiting example illustrated, there are four apertures in a first set of apertures 2405 and there are four apertures in a second set of apertures 2410, with each aperture positioned radially at 90 degrees to each neighbouring aperture in a set, and there are two sets of apertures positioned along the axial length of fluid guide tube 2400 separated by a distance d. In various examples, each aperture is a hole of diameter between 1 micron and 200 microns, preferably between 10 microns and 100 microns. More preferably each aperture is a hole of diameter between 30 microns and 50 microns. In a specific example, each aperture is a hole of diameter of about 30, 40 or 50 microns. The distance d between first set of apertures 2405 and second set of apertures 2410 is preferably between 5 mm and 50 mm. More preferably, the distance d between first set of apertures 2405 and second set of apertures 2410 is between 10 mm and 30 mm. In particular examples, the distance d is 10, 11, 12, 13, 14, 15, 16, 17, 18, 19 or 20 mm. If more than two sets of apertures are used, the distance d can be used between each set of apertures, if desired, or different distances can separate sets of apertures of more than two sets or apertures are utilised. In various examples, the set of apertures 2410, nearest the distal end of fluid guide tube 2400, can be positioned greater than or equal to 1 mm, 5 mm, 10 mm, 15 mm or 20 mm from the distal end of fluid guide tube 2400. The fluid guide tube 2400 can have a variety of internal and external diameters. For example, the fluid guide tube 2400 could be 16G LW PTFE medical tubing supplied by Zeus Industrial Products, Inc. with an internal diameter of 1.35 mm. It should be realised that the same aperture sizes, number and spacing, can be used for one or more apertures in outer tube 2160 when there are apertures utilised in the outer tube.

Figure 26:
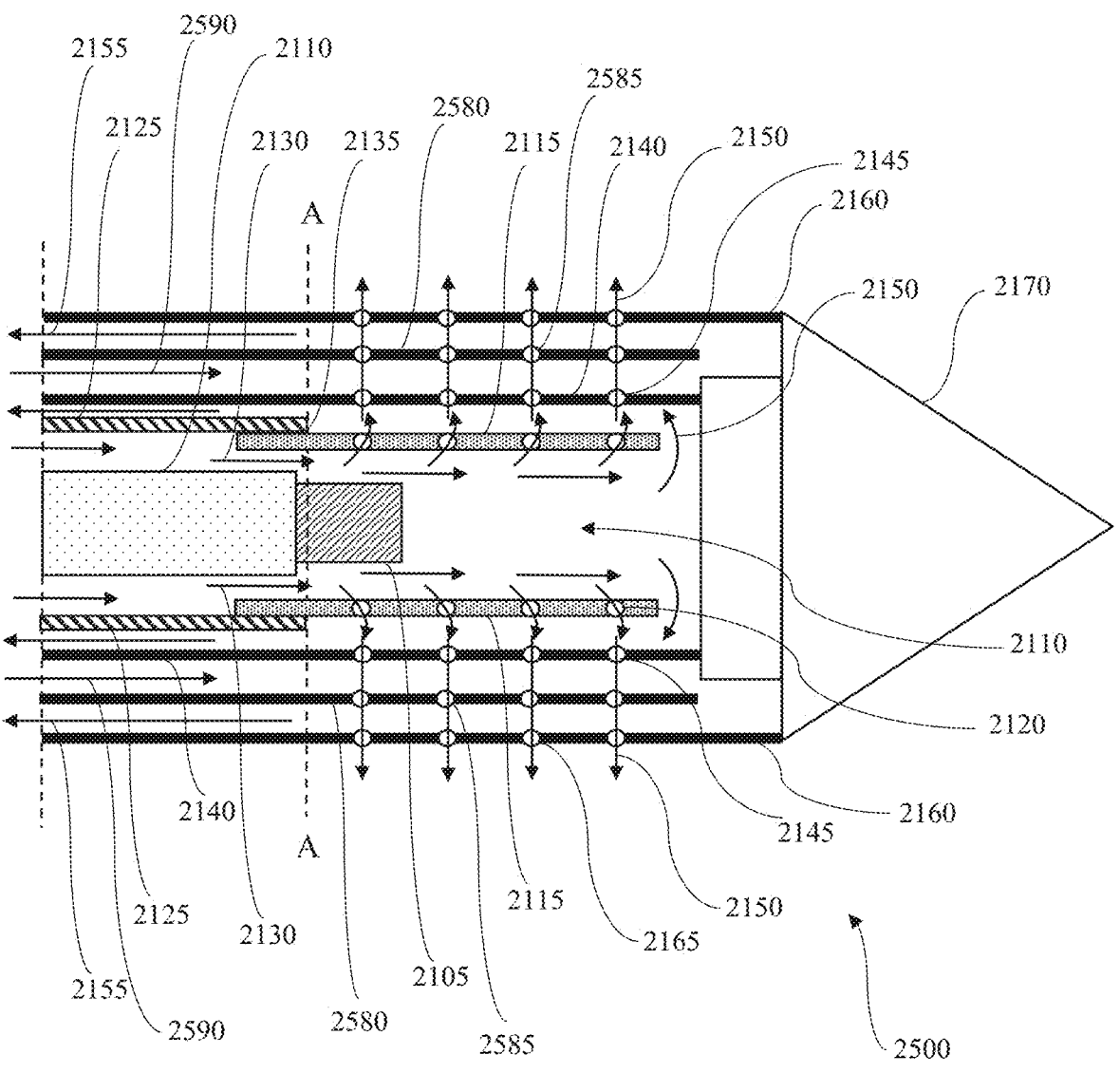
FIG. 26 illustrates a cross-sectional view of an end section (near an operational zone) of another example system with cooling fluid for interstitial laser therapy, where more than one fluid guide tube is provided and indicative fluid flows are illustrated by arrows.

FIG. 26 illustrates a cross-sectional view of an end section (near an operational zone where tissue is being removed by laser therapy) of another example system with cooling fluid 2500 for interstitial laser therapy. In system with cooling fluid 2500, more than one fluid guide tube is provided and indicative cooling fluid flows 2130, 2150, 2155 are illustrated by the arrows. First fluid guide tube 2140, having one or more apertures 2145, is provided internal to second fluid guide tube 2580 having one or more apertures 2585. Alternatively, in another example, fluid flows can be different or reversed from that illustrated, and the cooling fluid can flow into the second fluid guide tube 2580 via at least the one or more fluid second guide tube apertures 2585. A plurality of fluid guide tubes can be used, for example a single fluid guide tube, two fluid guide tubes, three fluid guide tubes, four fluid guide tubes, five fluid guide tubes, etc. Additionally, and optionally, the outer tube 2160 also can be provided with one or more apertures 2165. Different options for inlet cooling fluid flows and outlet cooling fluid flows can be utilised, for example there may be more than one inlet channel and/or more than one outlet channel. In the example illustrated, first inlet cooling fluid flow 2130 and, optionally, second inlet cooling fluid flow 2590 are utilised, with at least outlet cooling fluid flow 2155. In a preferred example, there is provided a single fluid guide tube with one or more apertures, as illustrated in FIG. 21.

Figure 27:
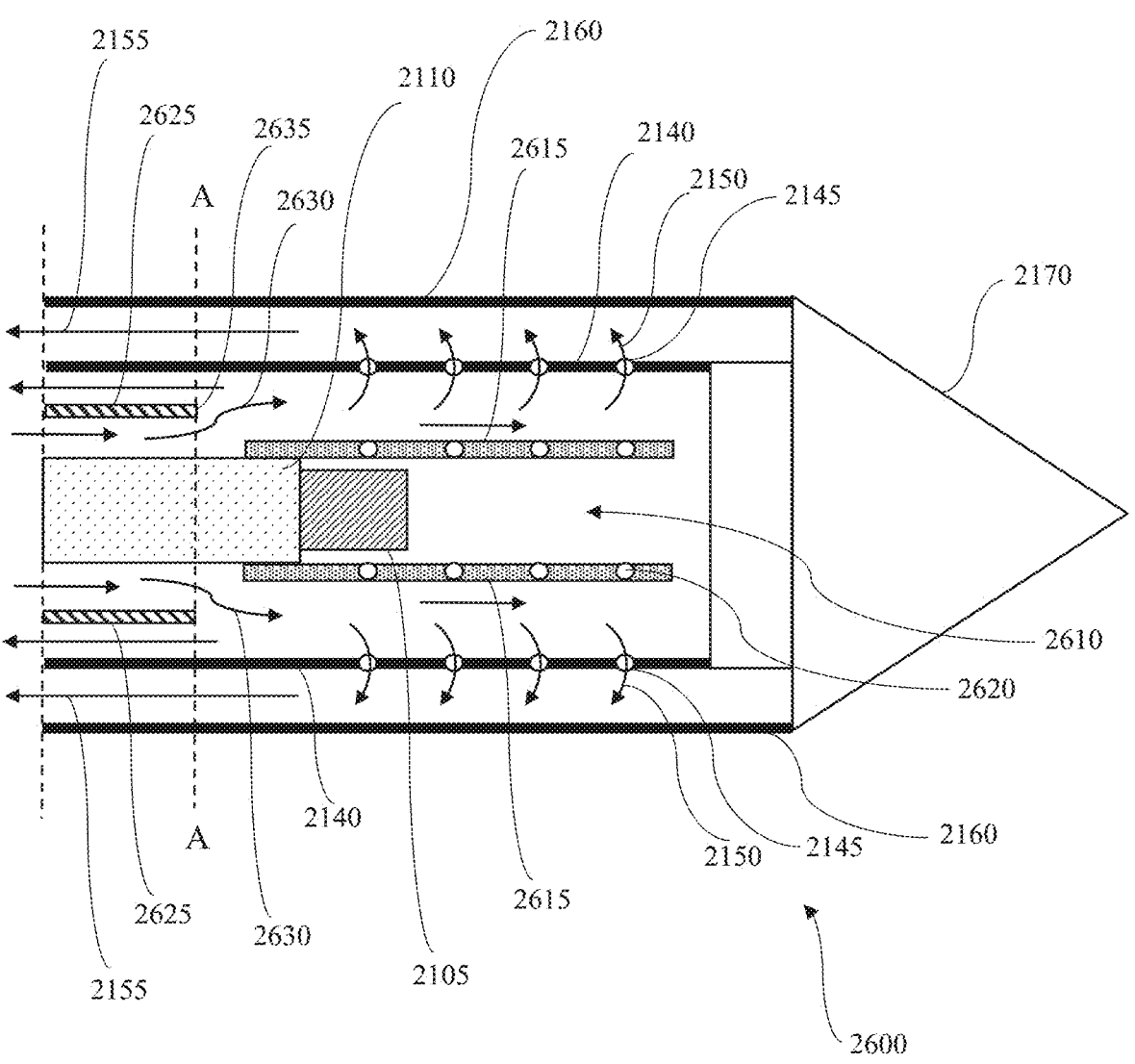
FIG. 27 illustrates a cross-sectional view of an end section (near an operational zone) of another example system provided with cooling fluid for interstitial laser therapy.

FIG. 27 illustrates a cross-sectional view of an end section (near an operational zone where tissue is being removed by laser therapy) of another example system with cooling fluid 2600 for interstitial laser therapy. Indicative cooling fluid flows are illustrated by the arrows. A device 2610 for interstitial laser therapy, similar to example devices for interstitial laser therapy as described and illustrated herein, is part of the system with cooling fluid 2600 for interstitial laser therapy. For the device 2610 for interstitial laser therapy illustrated, temperature sensors are not shown for clarity, however, previously described and illustrated example devices for interstitial laser therapy could be used. Device 2610 for interstitial laser therapy includes laser fibre 2105 (for example optical output end 112, 212, 312 of optical waveguide 110, 210, 310, or laser fibre 1550), and laser fibre jacket 2110 (for example outer layer 144, 244, 344 of optical waveguide 110, 210, 310, or laser fibre with jacket 1540, 1740). Device 2610 for interstitial laser therapy also includes optical diffuser 2615 (for example optical diffuser 130, 230, 330, 630, 730, 830, 930, 1030, 1130, 1230, 1330, 1530, 1730). Optical diffuser 2615 is preferably provided with one or more optical diffuser apertures 2620 as previously described and illustrated herein (for example one or more apertures, holes, slits, openings and/or vents 640, 740, 840, 940, 1040, 1240, 1340, 1560). The irrigation tube 2625 surrounds laser fibre jacket 2110 and directs input cooling fluid as fluid flows 2630 to flow out of distal end 2635, or tip, of irrigation tube 2625. This arrangement means cooling fluid is directed to flow outside of and cool optical diffuser 2615. As described previously, irrigation tube 2625 can be rigid, for example to assist in stiffening or supporting the length of the device for interstitial laser therapy 2610, or the irrigation tube 2625 can be semi-rigid or flexible. In one preferred example the irrigation tube 2625 is a metal tube. In this example, imaginary line A-A is again defined at the distal end 2635, or tip, of irrigation tube 2625, being perpendicular to the lengthwise axis of irrigation tube 2625 (i.e. being perpendicular to central longitudinal axis 120). The fluid guide tube 2140 is provided to surround irrigation tube 2625 and optical diffuser 2615. Fluid guide tube 2140 is provided with one or more fluid guide tube apertures 2145. In this example, there is no overlap in longitudinal extent between irrigation tube 2625 and optical diffuser 2615, which directs fluid flows 2630 to be outside of optical diffuser 2615. That is, irrigation tube 2625 is not longitudinally coextensive with optical diffuser 2615. The distal end of optical diffuser near trocar 2170 may be open or closed. If open, cooling fluid may enter inside of the optical diffuser 2615 via the open end.

Figure 28:
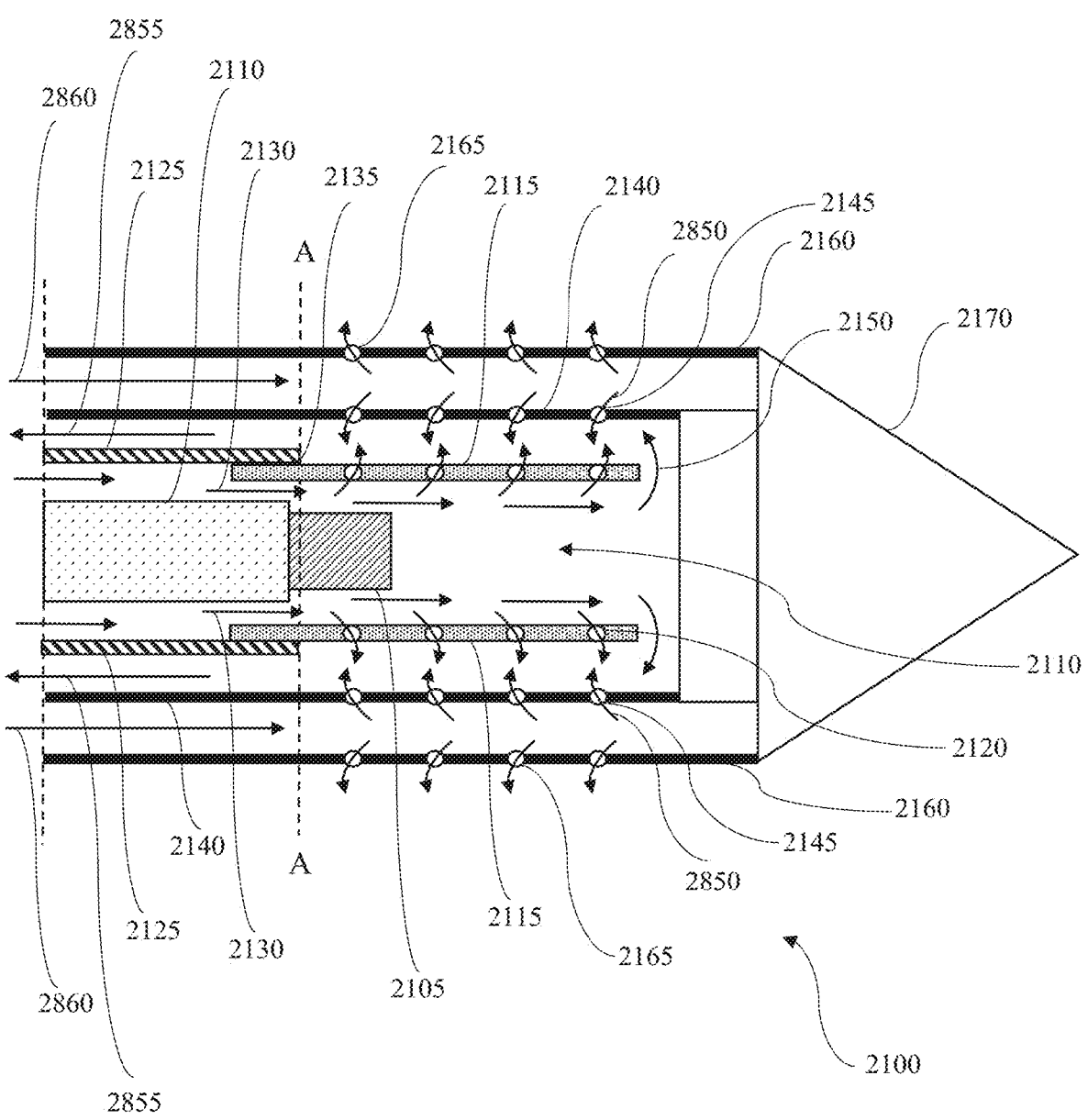
FIG. 28 illustrates a cross-sectional view of an end section (near an operational zone) of the example system provided with cooling fluid for interstitial laser therapy of FIG. 21, but instead making use of different fluid flows.

FIG. 28 illustrates a cross-sectional view of an end section (near an operational zone) of the example system provided with cooling fluid 2100 for interstitial laser therapy, as illustrated in FIG. 21. However, in the example of FIG. 28 different cooling fluid flow directions are utilised. Input fluid flows 2130, 2860 can be used to direct cooling fluid to the operational zone, that is in and/or about optical diffuser 2115. Cooling fluid can be removed from the operational zone, and away from optical diffuser 2115 after cooling optical diffuser 2115 and nearby areas, along return fluid flows 2855. Cooling fluid can flow through one or more fluid guide tube apertures 2145, in the illustrated example to flow into fluid guide tube 2140, as indicated by fluid flows 2850. Different fluid flow pathways are possible to those illustrated, and it should be realised that any of the flow directions can be reversed, for some or all fluid flow directions. In various examples as shown in the figures, the optical diffuser can be positioned over at least part of the irrigation tube, the optical diffuser can be positioned internal to at least part of the irrigation tube, and/or the optical diffuser can be fixed to at least part of the irrigation tube.

Figure 29:
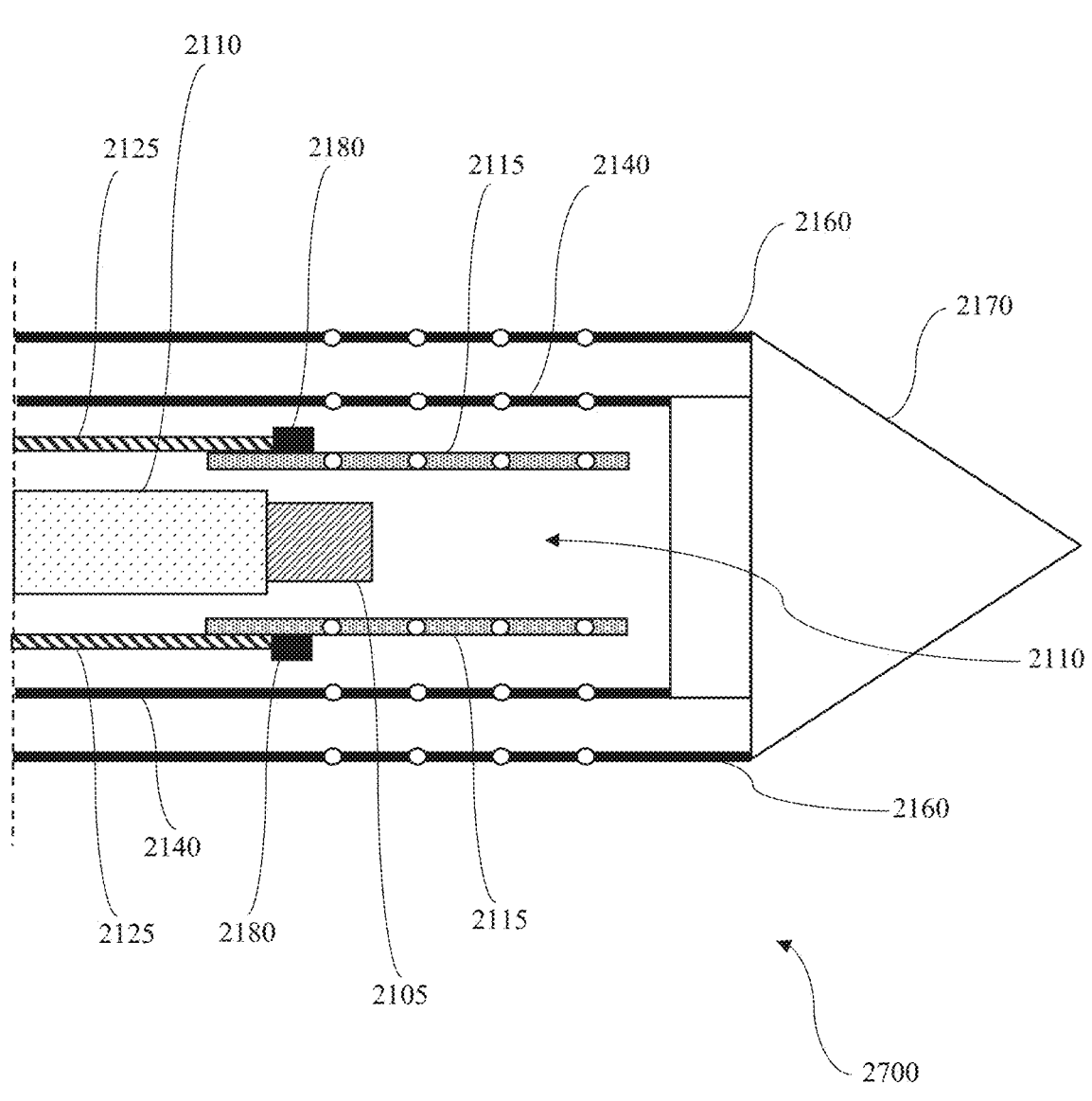
FIG. 29 illustrates a cross-sectional view of an end section (near an operational zone where tissue is being removed by laser therapy) of another example system for interstitial laser therapy provided with an annular ring as a thermal mass.

FIG. 29 illustrates a cross-sectional view of an end section (near an operational zone where tissue is being removed by laser therapy) of another example system 2700 for interstitial laser therapy. Additionally to previously described temperature sensor positions for various example embodiments, a temperature sensor can be provided by a thermocouple junction thermally connected to a component of the system 2700 which provides a thermal mass. A thermocouple junction can be provided by thermally bonding part of a thermocouple to a thermal mass (for example trocar 2170) and can be used to measure the temperature of the thermal mass (for example trocar 2170). Trocar 2170 can be utilised as a thermal mass at one end of the ablation zone and another second thermal mass can be thermally bonded to part of another thermocouple to provide a second thermocouple junction for a temperature measurement of the second thermal mass, preferably positioned at or near the other end of the ablation zone. For example, trocar 2170 can provide a first thermal mass and annular ring 2180 can provide a second thermal mass. In a preferred example, the annular ring is an annular metal ring. The annular ring could be made of other materials or composites providing a thermal mass, for example a metal alloy, a metal compound, graphite, carbon, diamond, etc.

A thermocouple junction is thus provided at trocar 2170, and a second thermocouple junction is thus provided at annular ring 2180, preferably though not necessarily being made of metal, a metal alloy, a metal compound, or graphene. Thus, in one embodiment trocar 2170 forms part of a thermocouple. In another embodiment, annular ring 2180, i.e. annular metal ring 2180, forms part of a second thermocouple. Annular ring 2180 can be positioned at various locations, but it is preferred to longitudinally position annular ring 2180 at an end of ablation zone opposite to the other end of the ablation zone near trocar 2170. For example, as illustrated, annular ring 2180 can be longitudinally positioned at or near a distal end of optical diffuser 2115, or longitudinally positioned at or near a distal end 2135 of irrigation tube 2125. Annular ring 2180 can be positioned external to optical diffuser 2115 and/or external to irrigation tube 2125. Alternatively, annular ring 2180 could be positioned internal to optical diffuser 2115 and/or internal to irrigation tube 2125. The measured temperature of trocar 2170 (i.e. first thermal mass) and the measured temperature of annular ring 2180 (i.e. second thermal mass) can be used to provide an estimator of the uniformity of the ablation zone. Use of thermal mass based measures of temperature can improve estimators of the efficacy of the ablation and coincidentally provide improved feedback parameters for control of laser power and/or control of cooling fluid flow, for example by control of a driving pump.

Figure 30:
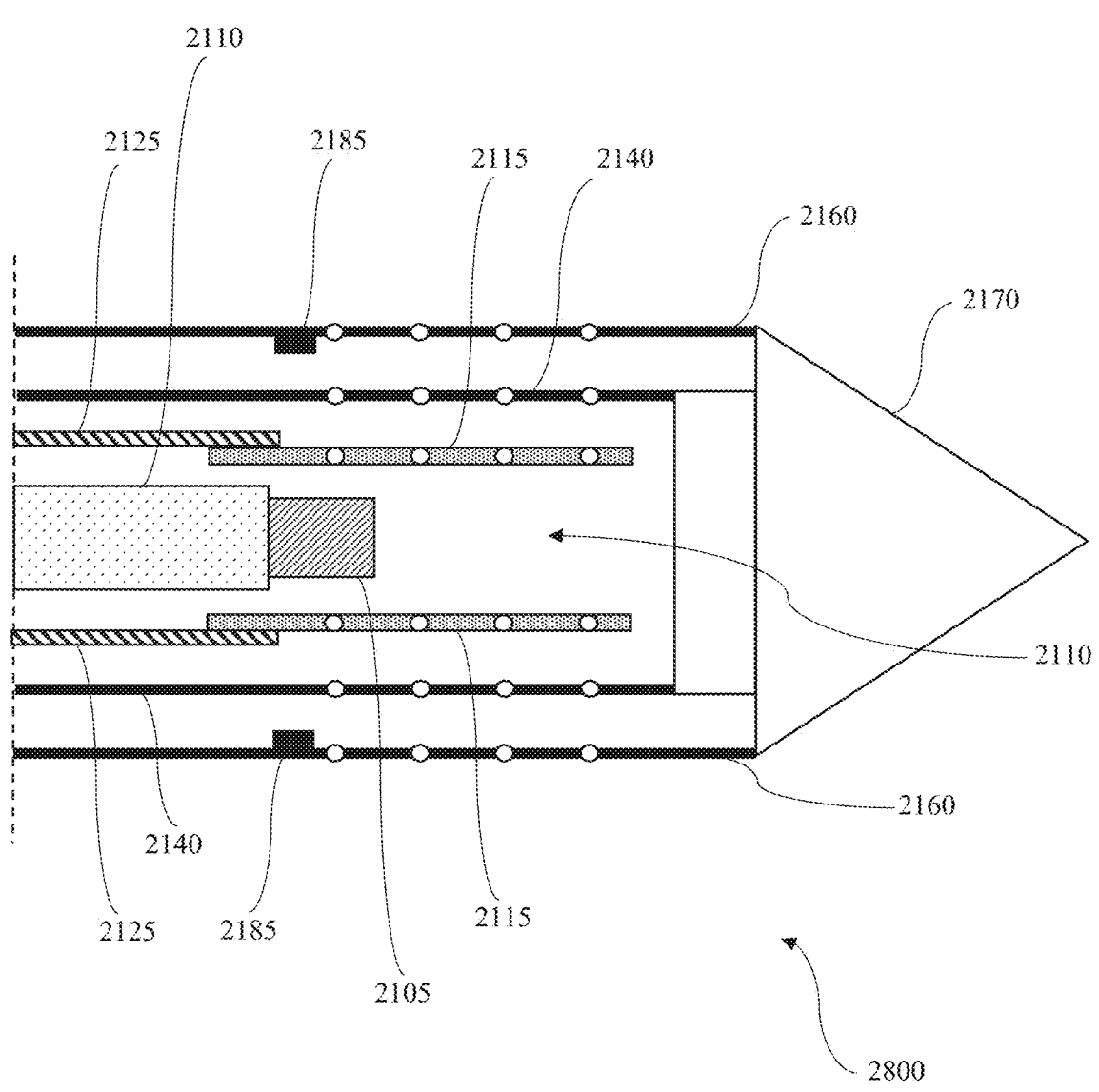
FIG. 30 illustrates a cross-sectional view of an end section (near an operational zone where tissue is being removed by laser therapy) of another example system for interstitial laser therapy provided with an annular ring as a thermal mass.

FIG. 30 illustrates a cross-sectional view of an end section (near an operational zone where tissue is being removed by laser therapy) of another example system 2800 for interstitial laser therapy. As in the previous example illustrated in FIG. 29, trocar 2170 can be utilised as a thermal mass at one end of the ablation zone and another second thermal mass can be thermally bonded to part of another thermocouple to provide a second thermocouple junction for a temperature measurement of the second thermal mass, preferably longitudinally positioned at or near the other end of the ablation zone. For example, trocar 2170 can provide a first thermal mass and annular ring 2185 can provide a second thermal mass, preferably though not necessarily being made of metal, a metal alloy, a metal compound, or graphene. In the example illustrated in FIG. 30, annular ring 2185, i.e. annular metal ring 2185, is positioned on or embedded in outer tube 2160. The longitudinal position of annular ring 2185 can be varied, although is preferably longitudinally positioned at an end of ablation zone opposite to trocar end 2170 of the ablation zone, for example at or near the cross-sectional location of distal end of irrigation tube 2125. In further examples, one or more ring-type thermocouple can be physically positioned on the outside of outer tube 2160. A ring-type thermocouple is similar to a ring electrode or an ablation ring. A ring-type thermocouple positioned on the outside of, or embedded within, outer tube 2160 provides direct temperature readings of surrounding tissue. As previously discussed, trocar 2170 itself can also be a thermocouple. Thus, in one embodiment trocar 2170 forms part of a thermocouple. In other embodiments, annular ring 2180, 2185 forms part of a second thermocouple, the annular ring 2180, 2185 being longitudinally positioned at or near a distal end of optical diffuser 2115 or at or near a distal end 2135 of irrigation tube 2125. In another embodiment, annular ring 2180 is positioned external to optical diffuser 2115. In another embodiment, annular ring 2185 is positioned external to or embedded within outer tube 2160.

Figure 31:
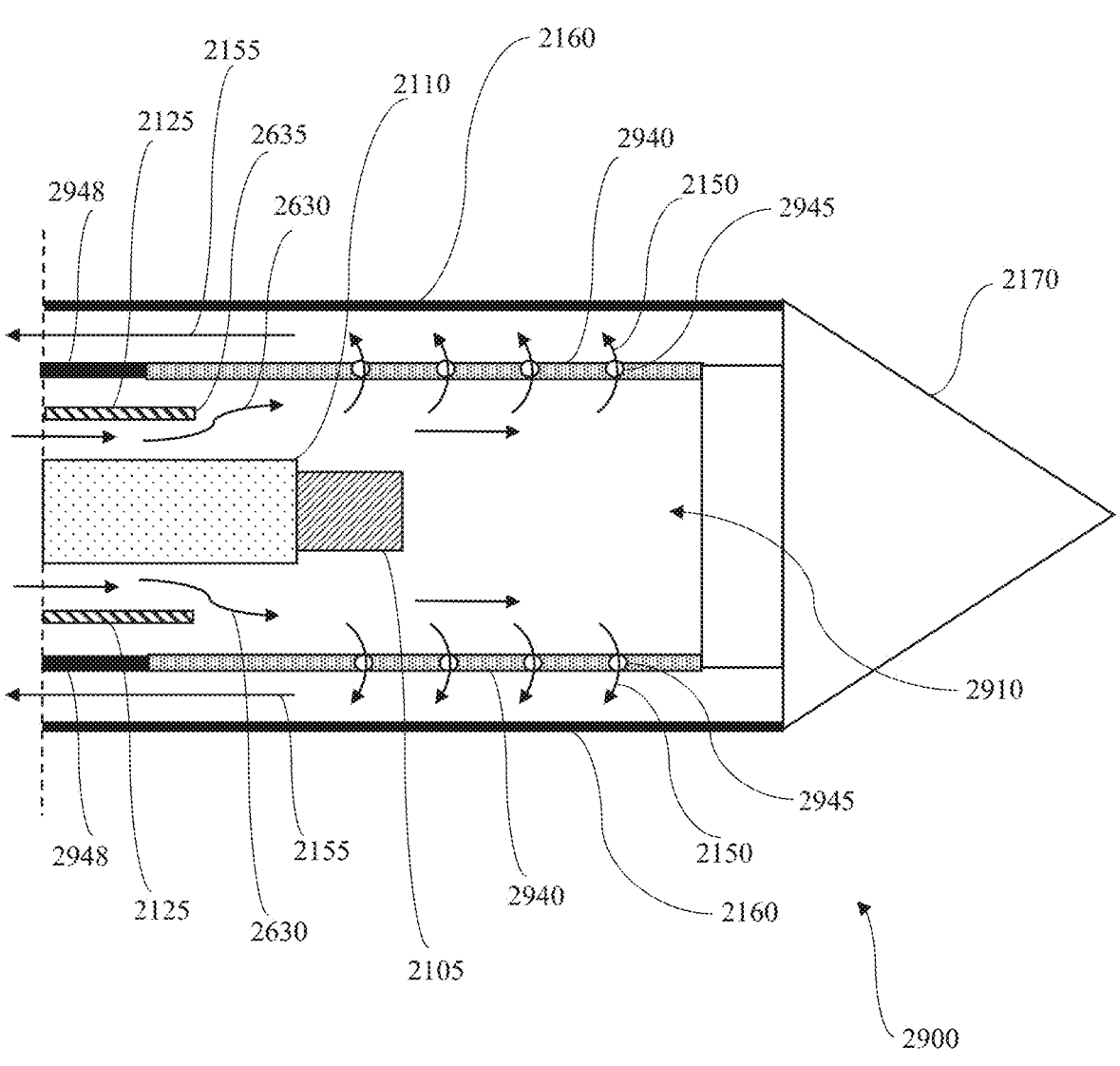
FIG. 31 illustrates a cross-sectional view of an end section (near an operational zone where tissue is being removed by laser therapy) of another example system with cooling fluid for interstitial laser therapy.

FIG. 31 illustrates a cross-sectional view of an end section (near an operational zone where tissue is being removed by laser therapy) of another example system with cooling fluid 2900 for interstitial laser therapy. In this example embodiment, an optical diffuser 2940 is not positioned on the laser waveguide, e.g. not positioned on laser fibre jacket 2110. The optical diffuser and the fluid guide tube are combined, or are the same component, and optical diffuser 2940 also acts as a fluid guide tube. Optical diffuser 2940 can be made of the same or similar materials as previous examples, for example a heat resistant material which also acts as an optical diffusing material. Optical diffuser 2940 can be positioned in a location the same as or similar to where the fluid guide tube was positioned in other examples. Indicative cooling fluid flows are illustrated by the arrows. A device 2910 for interstitial laser therapy is part of the system with cooling fluid 2900 for interstitial laser therapy. Temperature sensors are not shown for clarity. Device 2910 for interstitial laser therapy includes laser fibre 2105 (for example optical output end 112, 212, 312 of optical waveguide 110, 210, 310, or laser fibre 1550), and laser fibre jacket 2110 (for example outer layer 144, 244, 344 of optical waveguide 110, 210, 310, or laser fibre with jacket 1540, 1740). Device 2910 for interstitial laser therapy also includes optical diffuser 2940 (for example optical diffuser 130, 230, 330, 630, 730, 830, 930, 1030, 1130, 1230, 1330, 1530, 1730).

Optical diffuser 2940 is provided with one or more optical diffuser apertures 2945 as previously described and illustrated herein (for example one or more apertures, holes, slits, openings and/or vents 640, 740, 840, 940, 1040, 1240, 1340, 1560). The irrigation tube 2125 surrounds laser fibre jacket 2110 and directs input cooling fluid as fluid flows 2630 to flow out of distal end 2635, or tip, of irrigation tube 2125. This arrangement means cooling fluid is directed to flow inside of and cool optical diffuser 2940. Irrigation tube 2125 can be rigid, for example to assist in stiffening or supporting the length of the device for interstitial laser therapy 2910, or irrigation tube 2125 can be semi-rigid or flexible. In one example irrigation tube 2125 is a metal tube. Optical diffuser 2940, which also acts as a fluid guide tube, is provided external to, and may surround, irrigation tube 2125. Optical diffuser 2940 is provided with one or more optical diffuser apertures 2945 that also act as fluid guide apertures to direct or release cooling fluid. In various examples, there can be, or may not be, overlap in longitudinal extent between irrigation tube 2125 and optical diffuser 2940. In the example illustrated, irrigation tube 2125 is longitudinally coextensive with optical diffuser 2940. The distal end of optical diffuser 2945 near trocar 2170 may be open or closed. If open, cooling fluid may exit optical diffuser 2945 via the open end. Optical diffuser 2940 can be a single material along its entire length, or as illustrated, could be formed of different materials along its longitudinal extent. For example, optical diffuser 2940 could be joined to tube 2948, where optical diffuser 2940 is made of a material allowing diffusion of laser light, as previously described, and tube 2948 could be made of a different material, for example a rigid, semi-rigid or flexible metal tube. In one example, optical diffuser 2940 could be mechanically fitted around, and optionally sealed to, tube 2948, or vice versa. At least part of optical diffuser 2940 is composed of a light-transmissive material to allow electromagnetic radiation scattered within optical diffuser 2940 to radiate into tissue being treated.

Figure 32:
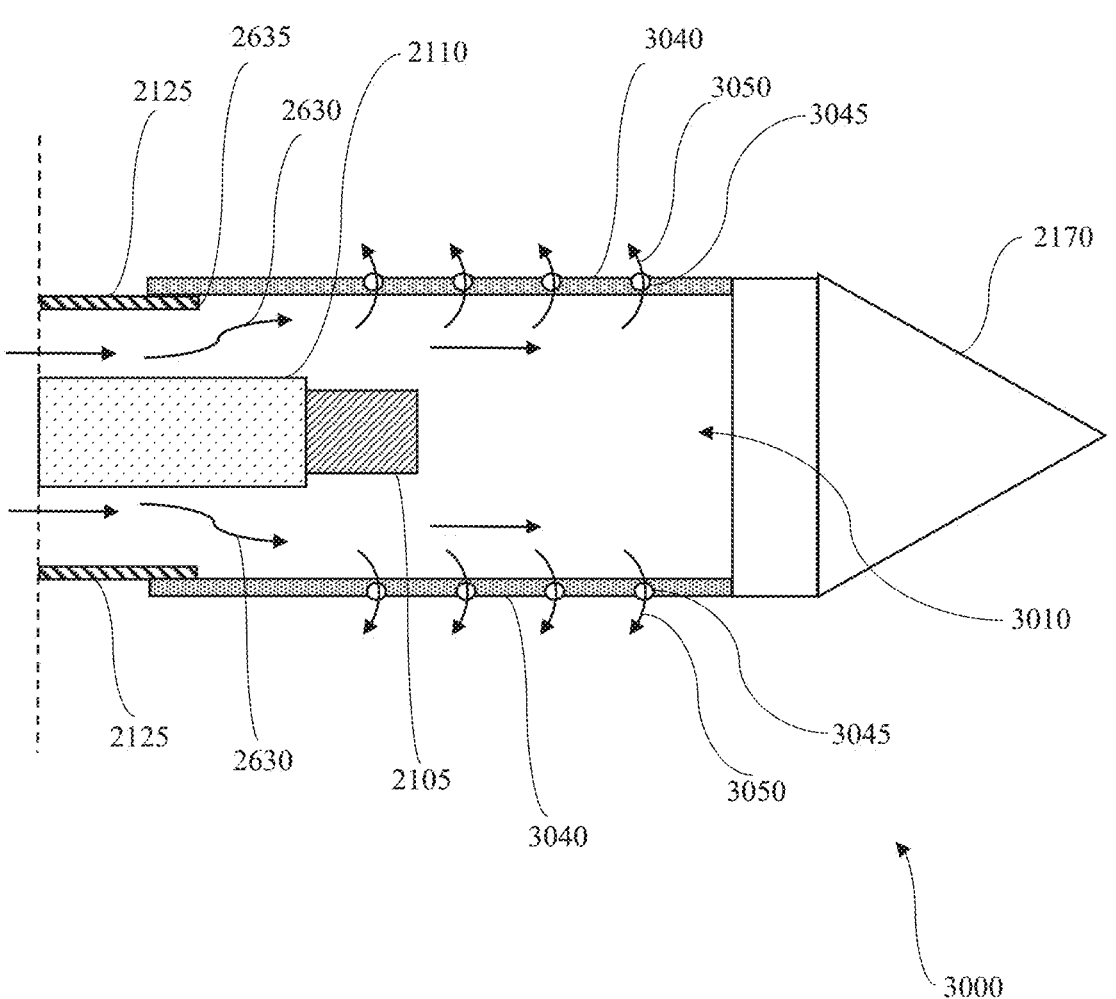
FIG. 32 illustrates a cross-sectional view of an end section (near an operational zone where tissue is being removed by laser therapy) of another example system with cooling fluid for interstitial laser therapy.

FIG. 32 illustrates a cross-sectional view of an end section (near an operational zone where tissue is being removed by laser therapy) of another example system with cooling fluid 3000 for interstitial laser therapy. In this example embodiment, optical diffuser 3040 is attached to irrigation tube 2125. Optical diffuser 3040 can be positioned external to irrigation tube 2125, as illustrated, or can be positioned internal to irrigation tube 2125. Optical diffuser 3040 can be attached to irrigation tube 2125 by mechanical abutment and/or joining with an adhesive to provide fluid-tight sealing. Optical diffuser 3040 also acts as a fluid guide tube and as an outer tube. Optical diffuser 3040 can be made of the same or similar materials as previous examples, for example a heat resistant material which also acts as an optical diffusing material. Thus, is this example there is not any dedicated and separate fluid guide tube and outer tube in addition to an optical diffuser.

In the example illustrated in FIG. 32, irrigation of cooling fluid 2630 is directly into the tissue surrounding optical diffuser 3040 as fluid/vapour 3050, and cooling fluid 2630 and fluid/vapour 3050 have a cooling effect on optical diffuser 3040 and/or laser fibre 2105. The cooling fluid 2630 can be vaporised so that gas and/or liquid can be released as fluid/vapour 3050 through one or more optical diffuser apertures 3045. When the cooling fluid 2630 used is water, this can provide a steam treatment effect to the surrounding tissue. In one example, the steam (i.e. 3050) can be super-heated steam which can kill tissue. The steam, being vapour, can transfer heat rapidly and effectively for an improved cooling effect. Indicative cooling fluid flows are illustrated by the arrows. A device 3010 for interstitial laser therapy is part of the system with cooling fluid 3000 for interstitial laser therapy. Temperature sensors are not shown for clarity. Device 3010 for interstitial laser therapy includes laser fibre 2105 (for example optical output end 112, 212, 312 of optical waveguide 110, 210, 310, or laser fibre 1550), and laser fibre jacket 2110 (for example outer layer 144, 244, 344 of optical waveguide 110, 210, 310, or laser fibre with jacket 1540, 1740). Device 3010 for interstitial laser therapy also includes optical diffuser 3040 (for example optical diffuser 130, 230, 330, 630, 730, 830, 930, 1030, 1130, 1230, 1330, 1530, 1730).

Optical diffuser 3040 is provided with one or more optical diffuser apertures 3045 as previously described and illustrated herein (for example one or more apertures, holes, slits, openings and/or vents 640, 740, 840, 940, 1040, 1240, 1340, 1560). The irrigation tube 2125 surrounds laser fibre jacket 2110 and directs input cooling fluid as fluid flows 2630 to flow out of distal end 2635, or tip, of irrigation tube 2125. This arrangement means cooling fluid is directed to flow inside of and cool optical diffuser 3040. Irrigation tube 2125 can be rigid, for example to assist in stiffening or supporting the length of the device for interstitial laser therapy 3010, or irrigation tube 2125 can be semi-rigid or flexible. In one example irrigation tube 2125 is a metal tube. Optical diffuser 3040 is provided with one or more optical diffuser apertures 3045 that also act as fluid guide apertures to direct or release cooling fluid and/or vapour, e.g. as steam. In various examples, there can be, or may not be, overlap in longitudinal extent between irrigation tube 2125 and optical diffuser 3040. For example, a joining tube could be positioned between irrigation tube 2125 and optical diffuser 3040 so that they do not overlap, if desired, but are mechanically fixed to each other. In the example illustrated, irrigation tube 2125 is longitudinally coextensive with optical diffuser 3040. The distal end of optical diffuser 3045 near trocar 2170 may be open or closed. If open, cooling fluid may exit optical diffuser 3045 via the open end.

Optical diffuser 3040 can be a single material along its entire length, or could be formed of different materials along its longitudinal extent. For example, optical diffuser 3040 and irrigation tube 2125 could be integrally formed as a single tube, or could be formed as a single tube with different sections made of different materials to thereby provide an optical diffuser section and an irrigation tube section. Optical diffuser 3040 is made of a material allowing diffusion of laser light, as previously described, and irrigation tube 2125 could be made of a different material, for example a rigid, semi-rigid or flexible metal tube. In one example, optical diffuser 3040 could be mechanically fitted around, and optionally sealed to, irrigation tube 2125, or vice versa. At least part of optical diffuser 3040 is composed of a light-transmissive material to allow electromagnetic radiation scattered within optical diffuser 3040 to radiate into tissue being treated.

Vibration Device (or Agitation Device)

In the previous examples describing various devices and systems for interstitial laser therapy, liquid cooling prevents the laser energy from causing the laser fibre (e.g. the optical waveguide) to disintegrate. A problem concerns the laser energy dissipated as heat that then needs to be mobilised or transferred. A problem for effective heat transfer is that the cooling fluid, which in one example is preferably water, changes state from liquid to gas, for example from liquid water to water vapor (in this case steam). This can result in parts or components of the system for interstitial laser therapy deforming, such as deformation of the optical diffuser, the fluid guide tube, or the outer tube (i.e. the cannula or the introducer) if the laser energy dissipated as heat outperforms the cooling ability of the cooling fluid.

The presence of the holes, slits, openings, and/or vents, i.e. apertures, in the optical diffuser enable the cooling fluid to remove the gas/steam bubbles in a controlled fashion. The removal of the heat is a fine balance of still allowing a suitable level of laser energy to be delivered for ablating tissue by not over-cooling or under-cooling using the cooling fluid.

The inventor has realised that during laser activation, gradual gas bubbles, or steam in the case of water as a cooling fluid, in an outflow tube for the cooling fluid, i.e. in the return fluid flows, are associated with detrimental over-heating of parts of the system for interstitial laser therapy, until such time as the gas bubbles (or steam) are released in the outflow tube. Additionally, during laser activation and use of the system, the presence of gas bubbles (or steam) have been observed using a microscope to be fixed or trapped at the distal end of the system. The inventor has realised that it is desirable to assist the release and transfer of gas bubbles (or steam) to the outflow tube and out of the system for interstitial laser therapy.

Vibrating or agitating at least part of the system for interstitial laser therapy releases and assists in the transfer of gas bubbles (or steam). By applying constant vibration or agitation, during use of the system, the temperature at or near a treatment site is observed to stabilise. This effect of producing a constant or near constant temperature during operation of the system for interstitial laser therapy is desirable for controlled tissue ablation.

Vibration or activation of at least part of the laser therapy system with a vibration device or an agitation device (i.e. a vibrator or an agitator), during laser activation also enhances the movement of gaseous products from the distal end of the laser therapy system. This further stabilises the liquid cooling mechanisms, operational temperature and enhances controlled tissue ablation. When gas bubbles (or steam) are removed from the laser therapy system, this results in more efficient cooling of the system and therefore allows more efficient use of laser energy for tissue ablation. The result is more efficient and quicker tissue ablation with a lower risk of deformation of parts of the laser therapy system.

The vibration device (or the agitation device) provides a mechanical force or stimulus that moves or physically vibrates part(s) of the laser therapy system, for example:
  the irrigation tube 2125, 2625,
  the optical diffuser 130, 230, 330, 630, 730, 830, 930, 1030, 1130, 1230, 1330, 1530, 1730, 2115, 2415, 2615, 2940, 3040,
  the fluid guide tube 2140, 2400, 2580, and/or
  the outer tube 1780, 2160 (e.g. the cannula or the introducer 1780).
In one example, one vibration device can be used to vibrate more than one component, for example to vibrate: (i) the irrigation tube and the optical diffuser; (ii) the irrigation tube and the fluid guide tube; (iii) the irrigation tube and the outer tube; (iv) the irrigation tube and the fluid guide tube and the outer tube. In other examples, more than one vibration device can be provided, each vibration device used to vibrate one of the irrigation tube, the fluid guide tube and the outer tube.

The applied vibrations can be applied at one frequency (i.e. a single frequency), applied at multiple frequencies, or applied at a variable frequency, that enhance the release and transfer of gas bubbles (or steam) to an outflow tube and out of the system for interstitial laser therapy. Use of one frequency, multiple frequencies, or variable frequencies depends on the component(s) and resonance characteristics. The applied vibration frequency can be different for different components of the laser therapy system. When more than one vibration device is used, the applied vibration frequency can be different for each of the vibration devices. The whole laser system could be vibrated or agitated, or only one or more parts of the laser system could be vibrated or agitated, for example only along an irrigation tube, a fluid guide tube or an outer tube. The frequency of the vibration device or the agitation device can be adjusted to provide maximal extraction of gas bubbles (or steam), for example by monitoring for a stable measured temperature.

Use of vibration/agitation has an added benefit to the clinical utility of a cannula. Cutaneous vibration is able to reduce both clinical and experimental pain, an effect called vibratory analgesia. The traditional explanation for this phenomenon is that it is mediated by lateral inhibition at the segmental (spinal cord) level, in pain-coding cells with center-surround receptive fields. Vibration has been used for cutaneous analgesia in clinical medicine.

Thus, when the vibration device is used to vibrate the outer tube 2160 (i.e. the cannula/introducer) there are multiple functions, including:

i. Immediate analgesia—when the body is being breached normally requiring local analgesia, ii. Prolonged analgesia—with the persistent vibration, iii. Agitation of the cannula—evacuation of gas bubbles at the therapy end of the closed system, and/or iv. Ability to have sensors at the end or any point of the cannula measure critical values, such as temperatures, intra cavity pressure, fluid flow etc.

The vibration device (or the agitation device) can be made from any device that causes vibration, such as a micromotor, a button or coin motor, or a piezo motor. These can include, x-y axis coin vibration motors, z-axis linear resonant actuators, rectangular linear vibration motors, eccentric rotating mass vibration motors, a piezoelectric plate vibrator, amongst other types. The vibration device can be embedded in, or directly or indirectly attached onto a component of the laser therapy system, for example: the irrigation tube 2125, 2625; the optical diffuser 130, 230, 330, 630, 730, 830, 930, 1030, 1130, 1230, 1330, 1530, 1730, 2115, 2415, 2615, 2940, 3040; the fluid guide tube 2140, 2400, 2580; and/or the outer tube 1780, 2160 (e.g. the cannula or the introducer 1780). Preferably, the vibration device is embedded in or directly or indirectly attached to the outer tube 1780, 2160 (e.g. the cannula or the introducer 1780). Attachment can be by any suitable means, for example using an adhesive, by plastic or metal welding, or by mechanical attachment such as using a bracket or clamp.

The vibration device is provided with a battery power source or is electrically connected to a remote power source. Alternatively, the vibration device can be a self-energy generating device that generates power to drive the vibration device. An example type of motor that can be used includes piezo-ceramics mounted on a vibration plate.

Figure 33:
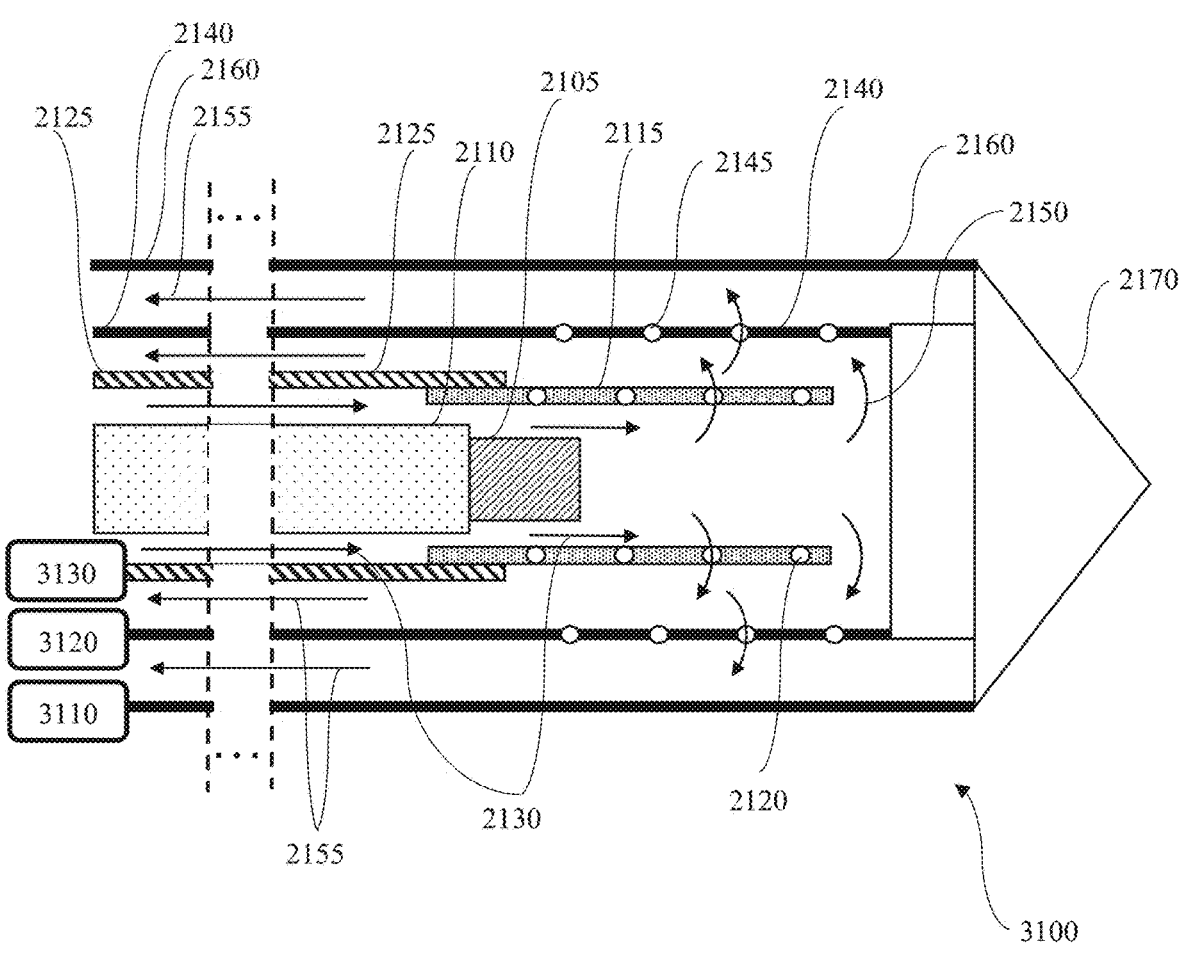
FIG. 33 illustrates a cross-sectional view of another example system with a vibration device(s) and cooling fluid for interstitial laser therapy, of indeterminate length showing an end section (near an operational zone where tissue is being removed by laser therapy) and another section for positioning of the vibration device(s).

FIG. 33 illustrates a cross-sectional view of an example system 3100 with a vibration device 3110, 3120, 3130 and cooling fluid for interstitial laser therapy, of indeterminate length showing an end section (near an operational zone where tissue is being removed by laser therapy) and another section for positioning of the vibration device 3110, 3120, 3130. The system 3100 is provided by way of example only, the vibration device 3110, 3120, 3130 can be used with any of the previously described example systems or devices, for example the systems or devices shown in any of FIGS. 1 to 32.

In FIG. 33, outer tube 2160 (i.e. a cannula or an introducer) is solid and does not have one or more apertures and so constrains and directs the flow of cooling fluid to be along return fluid flows 2155. In use the flow of cooling fluid 2130 out of irrigation tube 2125 acts to reduce temperatures in the system arising due to laser energy dissipation as heat. A laser ablation zone is the zone or region where laser power is sufficient to ablate tissue or cells. Irrigation tube 2125 may have a dual purpose, firstly in supporting laser fibre jacket 2110 so as to assist in safety and ease of insertion of laser fibre 2105 and optical diffuser 2115 into fluid guide tube 2140 (and outer tube 2160, for example the cannula/introducer provided with trocar 2170). Secondly, irrigation tube 2125 provides a cooling fluid flow channel for inflow of cooling fluid 2130 to be directed to optical diffuser 2115 and/or the region surrounding optical diffuser 2115. The flow of cooling fluid 2130, which exits irrigation tube 2125 at distal end 2135 of irrigation tube 2125, ameliorates, or prevents, the laser ablation zone from extending rearwards along the longitudinal length of outer tube 2160 away from trocar 2170. The limitation of the laser ablation zone to a region forward of the distal end, or tip, of irrigation tube 2125 provides for greatly improved accuracy of ablation of tissue in surgical use. The extent of and/or control of the ablation zone, leading to control of ablation, including for example the rate of ablation, can be controlled by different means. In a fixed laser power system, control of cooling fluid flow (i.e. coolant flow), in combination with monitoring of temperature allows an operator to control the extent and/or rate of ablation. In a fixed cooling fluid flow (i.e. coolant flow) system, control of laser power, in combination with monitoring of temperature also allows an operator to control the extent and/or rate of ablation.

The irrigation tube 2125 is positioned over or around at least part of the optical waveguide, and irrigation tube 2125 surrounds at least part of laser fibre jacket 2110 and directs input cooling fluid, that is input into irrigation tube 2125, as fluid flows 2130 to flow out of distal end 2135, or tip, of irrigation tube 2125. In the example illustrated in FIG. 33, irrigation tube 2125 is positioned over or around, i.e. surrounds, and can be sealed to or abut, an end part of optical diffuser 2115. This arrangement means cooling fluid is directed to flow towards and within, about, or around optical diffuser 2115, and in the example illustrated cooling fluid is directed to flow inside of and cool optical diffuser 2115. Cooling fluid is able to flow out of one or more optical diffuser apertures 2120, which are optional and may or may not be provided as part of optical diffuser 2115. Cooling fluid is also able to flow out of one or more apertures 2145 in fluid guide tube 2140. Preferably, one or more optical diffuser apertures 2120 are provided as part of optical diffuser 2115. Cooling fluid can also, in the example embodiment illustrated, flow out of an end of optical diffuser 2115 as illustrated by fluid flows 2150. Cooling fluid can be removed from the operational zone, and away from optical diffuser 2115 after cooling optical diffuser 2115 and nearby areas, along return fluid flows 2155. In the example illustrated, outer tube 2160 does not have one or more apertures and constrains and directs the flow of cooling fluid to be along return fluid flows 2155. Away from the operational zone, fluid flow channels for return fluid flows 2155 is provided by the external surface of fluid guide tube 2140 and the internal surface of outer tube 2160, and by the external surface of irrigation tube 2125 and the internal surface of fluid guide tube 2140.

One or more vibration devices 3110, 3120, 3130 (or agitation devices) provide a mechanical force or stimulus that moves or vibrates one or more parts of the laser therapy system 3100. For example, vibration device 3110 can be physically associated with, or attached to, the outer tube 2160 (e.g. the cannula or the introducer). Alternatively or additionally, vibration device 3120 can be physically associated with, or attached to, the fluid guide tube 2140. Alternatively or additionally, vibration device 3130 can be physically associated with, or attached to, the irrigation tube 2125, and by consequence physically connected with the optical diffuser 2115. The vibration device 3110, 3120, 3130 (or devices if more than one vibration device is used) can be associated with or attached to the outer tube 2160, the fluid guide tube 2140 and/or the irrigation tube 2125 at any convenient location, which is preferably away from the operational zone, i.e. the laser ablation zone, for example at or near a fluid inlet port or a fluid outlet port for the cooling fluid (preferably water).

Referring to FIG. 33 by way of example only, there is thus provided a system 3100 for interstitial laser therapy comprising an optical waveguide 2105 having an optical output end, an optical diffuser 2115 positioned over the optical output end of the optical waveguide 2105, an irrigation tube 2125, in use positioned over at least part of the optical waveguide 2105. The irrigation tube 2125 able to direct a cooling fluid 2130 to flow out of an end of the irrigation tube 2125. An outer tube 2160 is provided that in use is positioned over at least part of the irrigation tube 2125 and over the optical diffuser 2115, and a vibration device 3110, 3120, 3130.

In one example, the vibration device is used to vibrate the irrigation tube. In one example, the vibration device is used to vibrate the optical diffuser by vibrating the irrigation tube being attached to the optical diffuser. In one example, the vibration device is used to vibrate the outer tube. In another example, there is further provided a fluid guide tube, in use positioned over at least part of the optical diffuser and over at least part of the irrigation tube, and wherein in use the outer tube is positioned over at least part of the fluid guide tube. In one example, the vibration device is used to vibrate the fluid guide tube. In one example, the vibration device is used to vibrate: (i) the irrigation tube and the optical diffuser; (ii) the irrigation tube and the fluid guide tube; (iii) the irrigation tube and the outer tube; or (iv) the irrigation tube and the fluid guide tube and the outer tube.

In one example, there is more than one vibration device, each vibration device used to vibrate one of the irrigation tube and the outer tube. Optionally, the vibration device is a button or coin motor, or a piezo motor. Optionally, the vibration device is a piezoelectric plate vibrator. In one example, the vibration device is attached to the irrigation tube and/or the outer tube. Preferably, the vibration device is positioned away from a laser ablation zone. Optionally, the vibration device is positioned at or near a fluid inlet port or a fluid outlet port for the cooling fluid. Preferably, in use the vibration produced by the vibration device releases gas bubbles. Preferably, the cooling fluid is water and the gas bubbles are steam.

In one example, the optical diffuser is provided with one or more optical diffuser apertures. Preferably, the one or more optical diffuser apertures allow gases generated during use to escape out from an inside region of the optical diffuser. In one example, the cooling fluid is directed to flow inside of the optical diffuser, and wherein the cooling fluid flows out of the optical diffuser partially via at least the one or more optical diffuser apertures. Optionally, the fluid guide tube is provided with one or more fluid guide tube apertures. Preferably, the outer tube includes or is attached to a trocar.

It is known that vibration/agitation has been used prior to placement of a needle or sharp trocar placement in medicine. A vibrational pen/tool is used to "numb" the adjacent area where the needle is to be placed. Once the needle is then placed/introduced, the vibrational use of the separate vibrational pen/tool is complete. A tool (e.g. a cannula) that remains in place and continues to vibrate and modulate pain is not known. Such a vibrational device can be used to provide ongoing algesia when left inside the patient. The vibrational device could also be used without local analgesia, as the vibrational device will have analgesic effects, negating the need to pre anaesthetise with local analgesia. The ongoing vibration of the vibrational device will have a lasting analgesic benefit, especially with more prolonged procedures, where traditionally local sedation is used.

The vibration device (i.e. vibrator) or agitation device (i.e. agitator) can be part of a cannula (in-built) or can be provided as a separate vibration device to be attached to any form of cannula, or other device, that needs to be inserted into a body, body cavity or through the skin. A sensor can be placed on the tip of the cannula, such as a temperature or pressure sensor.

Optional embodiments may also be said to broadly include the parts, elements, steps and/or features referred to or indicated herein, individually or in any combination of two or more of the parts, elements, steps and/or features, and wherein specific integers are mentioned which have known equivalents in the art to which the invention relates, such known equivalents are deemed to be incorporated herein as if individually set forth. Although a preferred embodiment has been described in detail, it should be understood that many modifications, changes, substitutions or alterations will be apparent to those skilled in the art without departing from the scope of the present invention.

The invention claimed is:

1. A system for interstitial laser therapy comprising:
an optical waveguide having an optical output end;
an optical diffuser positioned over the optical output end of the optical waveguide;
an irrigation tube, in use positioned over at least part of the optical waveguide, the irrigation tube able to direct a cooling fluid to flow out of an end of the irrigation tube;
an outer tube, in use positioned over at least part of the irrigation tube and over the optical diffuser; and
a vibration device.

2. The system of claim 1, wherein the vibration device is used to vibrate the irrigation tube.

3. The system of claim 1, wherein the vibration device is used to vibrate the optical diffuser by vibrating the irrigation tube being attached to the optical diffuser.

4. The system of claim 1, wherein the vibration device is used to vibrate the outer tube.

5. The system of claim 1, further comprising a fluid guide tube, in use positioned over at least part of the optical diffuser and over at least part of the irrigation tube, and wherein in use the outer tube is positioned over at least part of the fluid guide tube.

6. The system of claim 5, wherein the vibration device is used to vibrate the fluid guide tube.

7. The system of claim 5, wherein the vibration device is used to vibrate:

(i) the irrigation tube and the optical diffuser;

(ii) the irrigation tube and the fluid guide tube;

(iii) the irrigation tube and the outer tube; or (iv) the irrigation tube and the fluid guide tube and the outer tube.

8. The system of claim 5, wherein the fluid guide tube is provided with one or more fluid guide tube apertures.

9. The system of claim 1, including more than one vibration device, each vibration device used to vibrate one of the irrigation tube and the outer tube.

10. The system of claim 1, wherein the vibration device is a button or coin motor, or a piezo motor.

11. The system of claim 1, wherein the vibration device is a piezoelectric plate vibrator.

12. The system of claim 1, wherein the vibration device is attached to the irrigation tube and/or the outer tube.

13. The system of claim 1, wherein the vibration device is positioned away from a laser ablation zone.

14. The system of claim 1, wherein the vibration device is positioned at or near a fluid inlet port or a fluid outlet port for the cooling fluid.

15. The system of claim 1, wherein in use, the vibration produced by the vibration device releases gas bubbles.

16. The system of claim 15, wherein the cooling fluid is water and the gas bubbles are steam.

17. The system of claim 1, wherein the optical diffuser is provided with one or more optical diffuser apertures.

18. The system of claim 17, wherein the one or more optical diffuser apertures allow gases generated during use to escape out from an inside region of the optical diffuser.

19. The system of claim 18, wherein the cooling fluid is directed to flow inside of the optical diffuser, and wherein the cooling fluid flows out of the optical diffuser partially via at least the one or more optical diffuser apertures.

20. The system of claim 1, wherein the outer tube includes or is attached to a trocar.

21. The system of claim 1, wherein the outer tube is a cannula and a liquid or a gas is directed to flow within the cannula.

22. The system of claim 21, wherein the cannula does not have one or more apertures and directs the flow of the liquid or the gas about the optical waveguide.

23. The system of claim 21, wherein the cannula is provided with one or more apertures along its length and the liquid is a cooling fluid that is pumped into or out of the cannula.

24. The system of claim 21, wherein the irrigation tube is not present.

* * * * *